United States Patent
Wang et al.

(10) Patent No.: US 9,290,499 B2
(45) Date of Patent: Mar. 22, 2016

(54) PYRAZOLOPYRIMIDINE COMPOUNDS FOR THE TREATMENT OF CANCER

(75) Inventors: Xiaodong Wang, Chapel Hill, NC (US); Jing Liu, Carrboro, NC (US); Chao Yang, Franklin Park, NJ (US); Weihe Zhaug, Chapel Hill, NC (US); Stephen Frye, Chapel Hill, NC (US); Dmitri Kireev, Chapel Hill, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 72 days.

(21) Appl. No.: 13/641,729

(22) PCT Filed: May 12, 2011

(86) PCT No.: PCT/US2011/036215
§ 371 (c)(1),
(2), (4) Date: Nov. 9, 2012

(87) PCT Pub. No.: WO2011/146313
PCT Pub. Date: Nov. 24, 2011

(65) Prior Publication Data
US 2013/0059836 A1     Mar. 7, 2013

Related U.S. Application Data

(60) Provisional application No. 61/346,241, filed on May 19, 2010, provisional application No. 61/374,729, filed on Aug. 18, 2010.

(51) Int. Cl.
| C07D 487/04 | (2006.01) |
| A61K 31/519 | (2006.01) |
| A61K 31/5377 | (2006.01) |
| A61K 31/551 | (2006.01) |
| A61P 35/00 | (2006.01) |
| A61P 35/02 | (2006.01) |

(52) U.S. Cl.
CPC .................................... C07D 487/04 (2013.01)

(58) Field of Classification Search
CPC ........................... C07D 487/04; A61K 31/519
USPC ........................................ 544/262; 514/262.1
See application file for complete search history.

(56) References Cited

U.S. PATENT DOCUMENTS

| 7,589,086 B2 | 9/2009 | Bondavalli et al. |
| 7,897,607 B2 | 3/2011 | Gyorkos et al. |
| 7,956,060 B2 | 6/2011 | Arai et al. |
| 7,998,978 B2 | 8/2011 | Huang et al. |
| 8,324,225 B2 | 12/2012 | Brain et al. |
| 8,362,023 B2 | 1/2013 | Liu et al. |
| 8,513,242 B2 | 8/2013 | Chiang et al. |
| 2006/0025383 A1 | 2/2006 | Wishart et al. |
| 2007/0078140 A1 | 4/2007 | Borzilleri et al. |
| 2007/0275984 A1 | 11/2007 | Imogai et al. |
| 2012/0035194 A1 | 2/2012 | Huang et al. |
| 2012/0207763 A1 | 8/2012 | Brain et al. |
| 2013/0072382 A1 | 3/2013 | Trullinger et al. |
| 2013/0102587 A1 | 4/2013 | Evans et al. |
| 2013/0137708 A1 | 5/2013 | Garske et al. |
| 2013/0150368 A1 | 6/2013 | Ashcraft et al. |

FOREIGN PATENT DOCUMENTS

| WO | WO 03/029209 A2 | 4/2003 |
| WO | WO 2005/009443 A1 | 2/2005 |
| WO | WO 2005/028434 A2 | 3/2005 |
| WO | WO 2006/035067 A2 | 4/2006 |
| WO | WO 2007/041379 A1 | 4/2007 |
| WO | WO 2007/044426 A2 | 4/2007 |
| WO | WO 2007/075554 A2 | 7/2007 |
| WO | WO 2007/113254 A1 | 10/2007 |
| WO | WO 2007/134828 A1 | 11/2007 |
| WO | WO 2009/032694 A1 | 3/2009 |
| WO | WO 2011/103441 A1 | 8/2010 |
| WO | WO 2010/129802 A1 | 11/2010 |
| WO | WO 2011/065800 A2 | 6/2011 |
| WO | WO 2011-090760 A1 | 7/2011 |
| WO | WO 2011/146313 A1 | 11/2011 |
| WO | WO 2012/053606 A1 | 4/2012 |
| WO | WO 2013/032591 A1 | 3/2013 |

(Continued)

OTHER PUBLICATIONS

Aly E-S A et al. Heteroannelations with o-amino aldehyde and o-amino cyano of some pyrazole derivatives. Afinidad, Barcelona, ES, vol. 61., No. 514, Jan. 1, 2004, pp. 510-515.

Extended European Search Report, EP 11783985.2, mailed Oct. 15, 2013.

Cavasotto CN et al. In silico identification of novel EGFR inhibitors with antiproliferative activity against cancer cells. Bioorganic & Medicinal Chemistry Letters. 2006; 16: 1969-1974.

(Continued)

*Primary Examiner* — Susanna Moore

(74) *Attorney, Agent, or Firm* — Myers Bigel & Sibley, P.A.

(57) ABSTRACT

Compound of Formula (I): are described, along with pharmaceutically acceptable salts thereof, compositions containing the same, and methods of use thereof in the treatment of cancer.

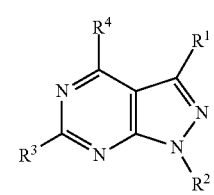

(I)

22 Claims, No Drawings

(56) References Cited

FOREIGN PATENT DOCUMENTS

WO     WO 2013/042006 A1     3/2013
WO     WO 2013/177168 A1     11/2013

OTHER PUBLICATIONS

International Search Report and Written Opinion, PCT/US2011/036215, mailed Aug. 16, 2011.
U.S. Appl. No. 14/348,805, filed Oct. 17, 2012, The University of North Carolina at Chapel Hill.
U.S. Appl. No. 14/384,789, filed Sep. 12, 2014, The University of North Carolina at Chapel Hill.
U.S. Appl. No. 14/436,356, filed Apr. 16, 2015, The University of North Carolina at Chapel Hill.
U.S. Appl. No. 14/678,905, filed Apr. 3, 2015, The University of North Carolina at Chapel Hill.
U.S. Appl. No. 14/678,830, filed Apr. 3, 2015, The University of North Carolina at Chapel Hill.
U.S. Appl. No. 14/678,678, filed Apr. 3, 2015, The University of North Carolina at Chapel Hill.
U.S. Appl. No. 14/678,879, filed Apr. 3, 2015, The University of North Carolina at Chapel Hill.
U.S. Appl. No. 14/678,898, filed Apr. 3, 2015, The University of North Carolina at Chapel Hill.
U.S. Appl. No. 14/678,540, filed Apr. 3, 2015, The University of North Carolina at Chapel Hill.
PCTUS15024381, The University of North Carolina at Chapel Hill, Apr. 3, 2015.
PCT/US15/024393, The University of North Carolina at Chapel Hill, Apr. 4, 2015.
PCT/US15/024395, The University of North Carolina at Chapel Hill, Apr. 3, 2015.
PCT/US15/024395, The University of North Carolina at Chapel Hill, Apr. 4, 2015.
PCT/US15/024328, The University of North Carolina at Chapel Hill, Apr. 3, 2015.
PCT/US15/024258, The University of North Carolina at Chapel Hill, Apr. 3, 2015.
PCT/US15/024396, The University of North Carolina at Chapel Hill, Apr. 4, 2015.
PCT/US15/024380, The University of North Carolina at Chapel Hill, Apr. 3, 2015.
PCT/US15/024301, The University of North Carolina at Chapel Hill, Apr. 3, 2015.
Cook, et al. "MerTK inhibition in tumor leukocytes decreases tumor growth and metastasis" *J Clin Invest*, 2013; 123: 3231-3242.
Earp, S. "Chemical Biology Consortium: Mer Kinase Inhibitor Studies" Presentation, *Chemical Biology Consortium*, Jan. 26, 2012.
Extended European Search Report, EP 12839069.7, mailed May 4, 2015.
Frye, S. "Academic Drug Discovery: US Perspective and Examples" Presentation, *NCI Translational Science Meeting*, Washington DC, Jul. 29, 2011.
International Search Report and Written Opinion, PCT/US2013/042033, mailed Aug. 27, 2013.
International Preliminary Report on Patentability; PCT/US2013/042033, mailed Dec. 4, 2014.
Linger et al. "Mer receptor tyrosine kinase is a therapeutic target in pre-B-cell acute lymphoblastic leukemia" *Blood*, 2013; 122(9); 1599-1609.
Liu, J. et al. "Discovery of Novel Small Molecule Mer Kinase Inhibitors for the Treatment of Pediatric Acute Lymphoblastic Leukemia" *ACS Med Chem Lett.*, Feb. 9, 2012; 3(2): 129-134.
Schlegel et al., "Mer receptor tyrosine kinase is a therapeutic target in melanoma" *J Clin Invest*, May 2013; 123(5); 2257-67.
Examination Report corresponding to European Application No. 13793925.2 dated Nov. 30, 2015.

PYRAZOLOPYRIMIDINE COMPOUNDS FOR THE TREATMENT OF CANCER

RELATED APPLICATIONS

This application is a 35 U.S.C. §371 national phase entry of PCT Application PCT/US2011/036215, filed May 12, 2011, and published in English on Nov. 24, 2011, as International Publication No. WO 2011/146313, and which claims the benefit under 35 U.S.C. §119(e) of U.S. Provisional Patent Application Ser. No. 61/374,729, filed Aug. 18, 2010, and U.S. Provisional Patent Application Ser. No. 61/346,241, filed May 19, 2010, the disclosure of each of which is incorporated herein by reference in its entirety.

STATEMENT OF FEDERAL SUPPORT

This invention was made with government support under Grant Number HHSN261200800001E awarded by the National Institutes of Health. The government has certain rights in the invention.

FIELD OF THE INVENTION

The present invention concerns compounds, compositions and methods for the treatment of cancer.

BACKGROUND OF THE INVENTION

Acute Lymphoblastic Leukemia (ALL) is the most common malignancy in children and common varieties are cured by chemotherapy in 75%-85% of the cases. Collectively the less common T cell and rare B cell subsets represent less than 2000 cases yearly and thus can be classified as a rare disease; these subsets have a poorer prognosis. Unfortunately with either subset, resistance to and relapse from therapy is a major cause of pediatric cancer death. In addition, ALL chemotherapies can cause late complications that are increasingly recognized in pediatric survivor populations. In fact, in pediatric cancer survivors, the incidence of severe late effects (neurocognitive sequelae, auditory complications, cardiovascular dysfunction, gastrointestinal/hepatic dysfunction, growth delay, secondary malignancies, and infertility) directly related to therapy is approximately 25%. A better understanding of therapeutic resistance and its reversal could not only help those who relapse but may help lower the dose of chemotherapy needed in ALL patients thus reducing long-term toxicity for future survivors.

SUMMARY OF THE INVENTION

The ectopic expression of Mer receptor tyrosine kinase (Mer) has been identified as a tumor cell survival gene product in Acute Lymphoblastic Leukemia (ALL) cells and a potential cause of ALL chemoresistance. Hence, we investigated whether the development of small molecule Mer inhibitors was possible.

A first aspect of the present invention is a compound (sometimes referred to as an "active compound" herein) of Formula I:

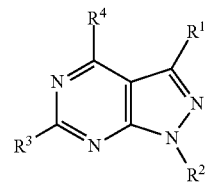

wherein:
$R^1$ is aryl;
$R^2$ is $—R^5R^6$, where $R^5$ is a covalent bond or C1 to C3 alkyl and $R^6$ is cycloalkyl, heterocycloalkyl, aryl, heteroaryl or alkyl, and wherein $R^6$ is optionally substituted from one to two times with independently selected polar groups;
$R^3$ is $—NR^7R^8$, where $R^7$ and $R^8$ are each independently selected from H, alkyl, arylalkyl; and alkoxyalkyl; and
$R^4$ is H, loweralkyl, halo, or loweralkoxy;
or a pharmaceutically acceptable salt or prodrug thereof.

A further aspect of the invention is an active compound as described herein in a pharmaceutically acceptable carrier.

A further aspect of the invention is a method of treating cancer in a subject in need thereof, comprising administering said subject an active compound as described herein in an amount effective to treat the cancer.

A further aspect of the invention is an active compound as described herein for use in treating cancer, and/or for the preparation of a medicament for the treatment of cancer.

DETAILED DESCRIPTION OF PREFERRED EMBODIMENTS

"Deuterium" as used herein alone or as part of another group, refers to a safe, non-radioactive relative of hydrogen. Any hydrogen may be replaced with deuterium to modify/improve metabolic stability, resulting in better safety, tolerability and/or efficacy.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —$NO_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$, are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl (or "t-BOC") groups, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates). The polar group can be an ionic group.

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc.

"Treat" as used herein refers to any type of treatment that imparts a benefit to a patient afflicted with a disease, including improvement in the condition of the patient (e.g., in one or more symptoms), delay in the progression of the disease, delay in onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

Active compounds of the present invention may optionally be administered in conjunction with other compounds useful in the treatment of cancer. The other compounds may optionally be administered concurrently. As used herein, the word "concurrently" means sufficiently close in time to produce a combined effect (that is, concurrently may be simultaneously, or it may be two or more events occurring within a short time period before or after each other).

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. Subjects may be of any age, including infant, juvenile, adolescent, adult, and geriatric subjects.

1. Active Compounds.

As noted above, the present invention provides active compounds of Formula I:

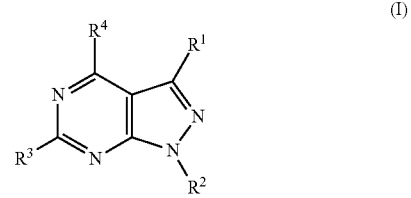

(I)

wherein:
R$^1$ is aryl;
R$^2$ is —R$^5$R$^6$, where R$^5$ is a covalent bond or C1 to C3 alkyl and R$^6$ is cycloalkyl, heterocycloalkyl, aryl, heteroaryl or alkyl, and wherein R$^6$ is optionally substituted from one to two times with independently selected polar groups;
R$^3$ is —NR$^7$R$^8$, where R$^7$ and R$^8$ are each independently selected from H, alkyl, arylalkyl; and alkoxyalkyl; and
R$^4$ is H, loweralkyl, halo, or loweralkoxy;
or a pharmaceutically acceptable salt or prodrug thereof.

In some embodiments of the foregoing, R$^1$ is phenyl or pyridyl, which phenyl or pyridyl is unsubstituted or substituted from 1 to 3 times with halo, amino, nitro, alkyl, alkoxyl, haloalkyl, cycloalkyl, heterocycloalkyl, aryl, or heteroaryl.

In some embodiments of the foregoing $R^5$ is —$CH_2$—.

In some embodiments of the foregoing, $R^8$ is C1-C8 alkyl, C3-C8 cycloalkyl, or C1-C8 alkyl aryl.

In some embodiments of the foregoing, $R^6$ is cyclohexyl.

In some embodiments of the foregoing, $R^6$ is substituted once with amino.

In some embodiments of the foregoing, $R^7$ is H.

In some embodiments of the foregoing, $R^8$ is loweralkyl.

In some embodiments of the foregoing, $R^4$ is H.

Particular examples of compounds of the present invention include but are not limited to those set forth in Tables 1-3 below.

Active compounds may be provided as pharmaceutically acceptable prodrugs, which are those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

The active compounds disclosed herein can, as noted above, be provided in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active compounds as described herein can be prepared in accordance with known procedures, or variations thereof that will be apparent to those skilled in the art.

2. Pharmaceutical Formulations.

The active compounds described above may be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), transdermal administration, and intraventricular injection (injection into a ventricle of the brain, e.g., by an implanted catheter or omman reservoir, such as in the case of morbid obesity) and although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. In some embodiments, a dosage from about 0.5 mg/kg to 5 mg/kg may be employed for intramuscular injection. In some embodiments, dosages are 1 µmol/kg to 50 µmol/kg, and more preferably 22 µmol/kg and 33 µmol/kg of the compound for intravenous or oral administration. The duration of the treatment can be once per day for a period of two to three weeks or until the condition is essentially controlled.

As noted above, the active compounds described herein are useful for the treatment of cancer. Example cancers that may be treated by the compounds and methods of the invention include, but are not limited to, myeloid leukemia, lymphoblastic leukemia, melanoma, breast, lung, colon, liver, gastric, kidney, ovarian, uterine, and brain cancer.

The present invention is explained in greater detail in the following non-limiting Examples.

EXPERIMENTAL

Preparation of Exemplary Compounds

General Structure:

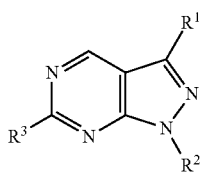

Example 1

The R[1] Position 1-((4-Aminocyclohexyl)methyl)-N-methyl-3-p-tolyl-1H-pyrazolo[3,4-d]pyrimidin-6-amine General Procedure A:

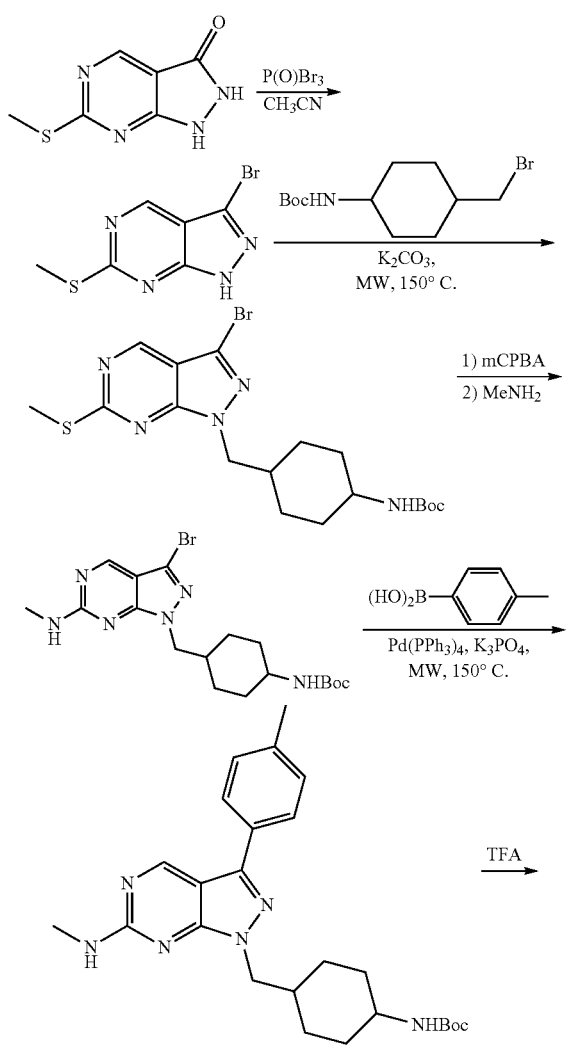

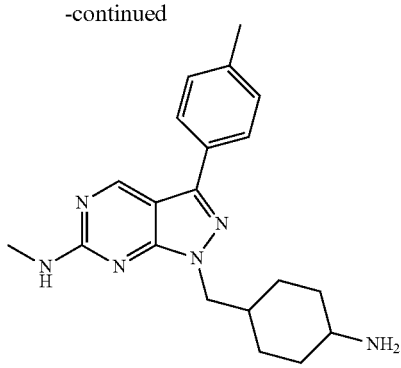

3-Bromo-6-(methylthio)-1H-pyrazolo[3,4-d]pyrimidine

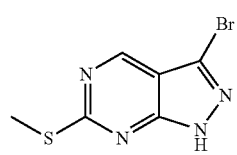

To a suspension of 6-(methylthio)-1H-pyrazolo[3,4-d]pyrimidin-3(2H)-one (0.50 g, 2.7 mmol) in $CH_3CN$ (15 mL) was added a $CH_3CN$ solution of $P(O)Br_3$ (1.57 g, 5.5 mmol) in a pressure vessel. The mixture was sonicated for 30 min before being heated to 100° C. for 16 h (overnight). After it was cooled to 0° C., $H_2O$ and aqueous ammonium hydroxide were added to basify the mixture. The mixture was stirred at 0° C. for 1 h. The aqueous layer was extracted with EtOAc (10×). The combined EtOAc layer was dried ($Na_2SO_4$), and concentrated to give 3-bromo-6-(methylthio)-1H-pyrazolo[3,4-d]pyrimidine (0.51 g, 77%) as a brown solid. $^1$H NMR (400 MHz, DMSO-d6) δ: 9.00 (s, 1H), 5.57 (s, 3H); MS m/z 245.00 $[M+H]^+$.

tert-Butyl 4-((3-bromo-6-(methylthio-1H-pyrazolo[3,4-d]pyrimidin-1-yl)methyl)cyclohexylcarbamate

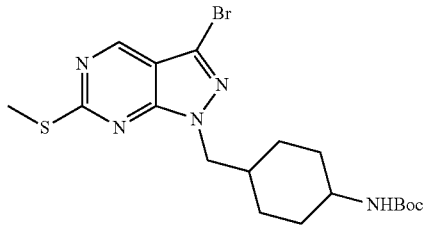 [SMILES: CSc1ncc2c(Br)nn(CC3CCC(NC(=O)OC(C)(C)C)CC3)c2n1]

A 10 mL microwave tube was charged with 3-bromo-6-(methylthio)-1H-pyrazolo[3,4-d]pyrimidine (0.3 g, 1.22 mmol), $K_2CO_3$ (0.51 g, 3.66 mmol), and DMSO (2 mL). The mixture was stirred for 20 min before 4-(bromomethyl)cyclohexylcarbamate (0.45 g, 1.53 mmol) and THF (4 mL) was added. The resulting mixture was heated at 150° C. for 10 minutes in microwave. The reaction mixture was poured into water and extracted with $Et_2O$ (3×). The combined ether layer was dried ($Na_2SO_4$) and concentrated. The crude mixture was purified by Isco to provide tert-butyl 4-((3-bromo-6-(methylthio)-1H-pyrazolo[3,4-d]pyrimidin-1-yl)methyl)cyclohexylcarbamate (0.46 g, 83%) as a white solid. MS m/z 478.10 $[M+Na]^+$.

tert-Butyl 4-((3-bromo-6-(methylamino)-1H-pyrazolo[3,4-d]pyrimidin-1-yl)methyl cyclohexylcarbamate

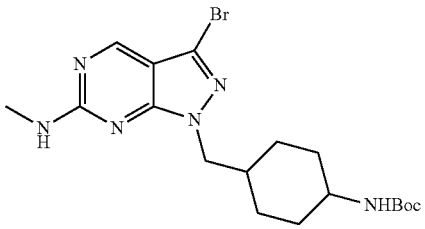 [SMILES: CNc1ncc2c(Br)nn(CC3CCC(NC(=O)OC(C)(C)C)CC3)c2n1]

To a solution of tert-butyl 4-((3-bromo-6-(methylthio)-1H-pyrazolo[3,4-d]pyrimidin-1-yl)methyl)cyclohexylcarbamate (0.91 g, 2.0 mmol) in $CH_2Cl_2$ (30 mL) was added meta-Chloroperoxybenzoic acid (1.34 g, 77%, 6 mmol) at room temperature. The color of the solution changed to light purple from colorless. After 2 h, the reaction was diluted with EtOAc. The organic solution was then washed with 1 N NaOH (3×), dried ($NaSO_4$), and concentrated. The resulting residue was dissolved in THF (10 mL) before a 2.0 M methylamine solution in THF (10 mL, 20 mmol) was added at room temperature. The resulting solution was heated at 60° C. for 2 h. After removal of the solvent, it was purified by Isco to provide tert-butyl 4-((3-bromo-6-(methylamino)-1H-pyrazolo[3,4-d]pyrimidin-1-yl)methyl)cyclohexylcarbamate (0.75 g, 85%) as a white solid. MS m/z 439.2 $[M+H]^+$.

tert-Butyl 4-((6-(methylamino)-3-p-tolyl-1H-pyrazolo[3,4-d]pyrimidin-1-ylmethyl)cyclohexylcarbamate

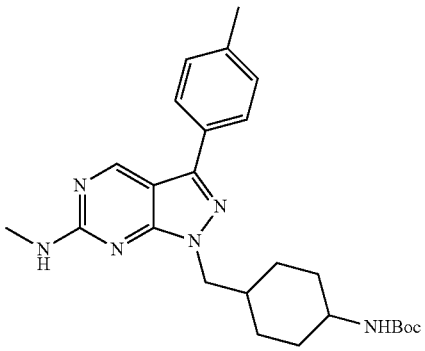 [SMILES: CNc1ncc2c(-c3ccc(C)cc3)nn(CC3CCC(NC(=O)OC(C)(C)C)CC3)c2n1]

A 30 mL microwave tube was charged with tert-butyl 4-((3-bromo-6-(methylamino)-1H-pyrazolo[3,4-d]pyrimidin-1-yl)methyl)cyclohexylcarbamate (0.070 g, 0.16 mmol), p-tolylboronic acid (0.065 g, 0.48 mmol), potassium phosphonate (0.10 g, 0.48 mmol), tetrakis(triphenylphosphine) palladium (0.018 g, 0.016 mmol), dioxane (2 mL) and water (0.5 mL). After stirring for 5 min, the reaction was heat at 150° C. for 10 min in microwave. The reaction was diluted with EtOAc and washed with water. The aqueous layer was extracted with EtOAc (3×). The combined organic layers were dried ($Na_2SO_4$), concentrated, and purified by Isco to provide tert-butyl 4-((6-(methylamino)-3-p-tolyl-1H-pyrazolo[3,4-d]pyrimidin-1-yl)methyl)cyclohexylcarbamate (0.064 g, 89%) as a white solid.

1-((4-Aminocyclohexyl)methyl)-N-methyl-3-p-tolyl-1H-pyrazolo[3,4-d]pyrimidin-6-amine

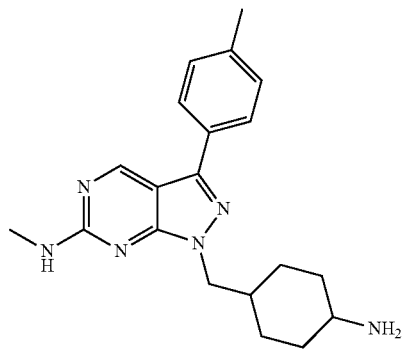 [SMILES: CNc1ncc2c(-c3ccc(C)cc3)nn(CC3CCC(N)CC3)c2n1]

To a solution of tert-butyl 4-((6-(methylamino)-3-p-tolyl-1H-pyrazolo[3,4-d]pyrimidin-1-yl)methyl)cyclohexylcarbamate (0.064 g, 0.14 mmol) in $CH_2Cl_2$ (2 mL) was added trifluoroacetic acid (0.6 mL) at ambient temperature. After stirring for 2 h, the solvent was evaporated. The residue was purified by preparative HPLC to provide 1-((4-aminocyclohexyl)methyl)-N-methyl-3-p-tolyl-1H-pyrazolo[3,4-d]pyrimidin-6-amine (UNC00000478A) as a yellow solid (TFA salt) (0.063 g, 95%). MS m/z 351.3 $[M+H]^+$.

Table 1 describes compounds prepared following procedures described in Example 1 (General Procedure A), using appropriate reagents. (Note: Mer IC50: ++++ means <10 nM; +++ means between 10-100 nM, ++ means between 100 nM-1 µM; + means between 1-30 µM; − means inactive.)

TABLE 1

| | Structure | Compound_ID | dr cis:trans | Mer $IC_{50}$ | Physical Data MS m/z (M + 1) or/and $^1$H NMR (400 MHz, $CD_3OD$) |
|---|---|---|---|---|---|
| 1 | (structure shown) | UNC00000353A | 1.7:1 | +++ | MS m/z 355.20 (M + 1). |

TABLE 1-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 2 | (4-fluorophenyl pyrazolopyrimidine with N-methylamine and aminocyclohexylmethyl) | UNC00000354A | 1.3:1 | +++ | MS m/z 355.20 (M + 1). |
| 3 | (2-fluorophenyl pyrazolopyrimidine with N-methylamine and aminocyclohexylmethyl) | UNC00000391A | 1.5:1 | ++ | MS m/z 355.20 (M + 1). |
| 4 | (4-chlorophenyl pyrazolopyrimidine with N-methylamine and aminocyclohexylmethyl) | UNC00000488A | 2:1 | +++ | MS m/z 371.20 (M + 1). |
| 5 | (3-methoxyphenyl pyrazolopyrimidine with N-methylamine and aminocyclohexylmethyl) | UNC00000355A | 1.7:1 | ++ | MS m/z 367.20 (M + 1). |

TABLE 1-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 6 | (structure with OCH$_3$ para-substituted phenyl) | UNC00000356A | 1.8:1 | +++ | MS m/z 367.20 (M + 1). |
| 7 | (structure with H$_3$CO ortho-substituted phenyl) | UNC00000392A | 1.8:1 | + | MS m/z 367.20 (M + 1). |
| 8 | (structure with CF$_3$ para-substituted phenyl) | UNC00000486A | 2:1 | ++ | MS m/z 405.20 (M + 1). |
| 9 | (structure with COOMe para-substituted phenyl) | UNC00000481A | 1:1 | +++ | MS m/z 395.20 (M + 1). |

TABLE 1-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 10 | 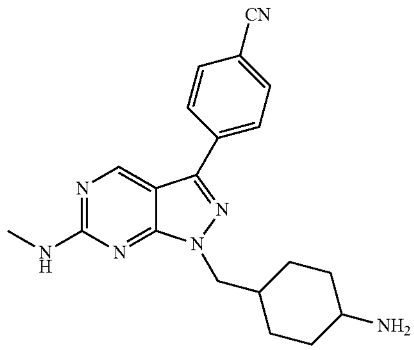 [SMILES: CNc1ncc2c(-c3ccc(C#N)cc3)nn(CC3CCC(N)CC3)c2n1] | UNC00000482A | 2:1 | ++ | MS m/z 362.20 (M + 1). |
| 11 | 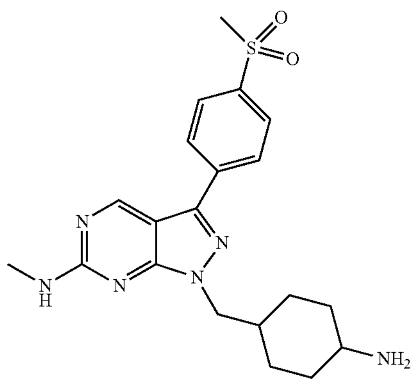 [SMILES: CNc1ncc2c(-c3ccc(S(C)(=O)=O)cc3)nn(CC3CCC(N)CC3)c2n1] | UNC00000492A | 2:1 | +++ | MS m/z 415.20 (M + 1). |
| 12 | 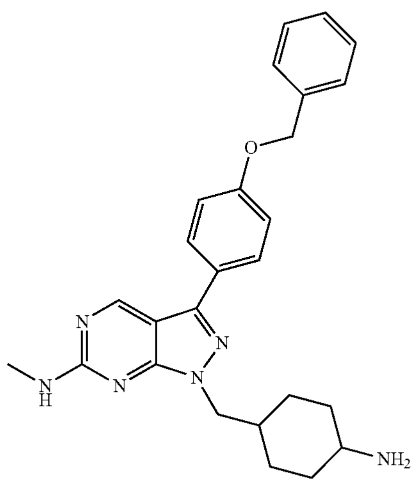 [SMILES: CNc1ncc2c(-c3ccc(OCc4ccccc4)cc3)nn(CC3CCC(N)CC3)c2n1] | UNC00000487A | 2:1 | +++ | MS m/z 443.30 (M + 1). |
| 13 | 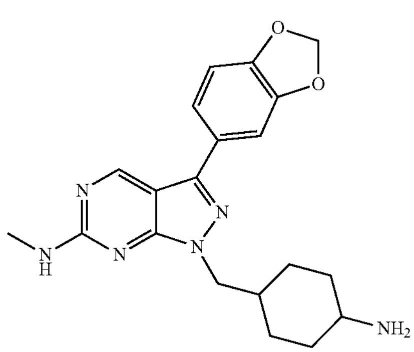 [SMILES: CNc1ncc2c(-c3ccc4c(c3)OCO4)nn(CC3CCC(N)CC3)c2n1] | UNC00000394A | 2.1:1 | ++ | MS m/z 381.20 (M + 1). |

TABLE 1-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 14 | 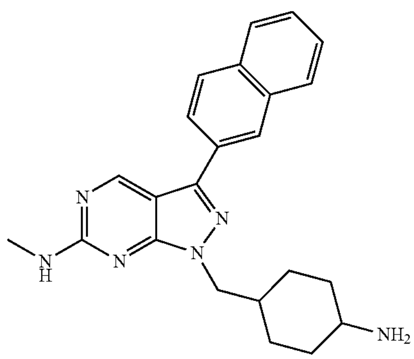 [SMILES: CNc1ncc2c(-c3ccc4ccccc4c3)nn(CC3CCC(N)CC3)c2n1] | UNC00000397A | 1.9:1 | ++ | MS m/z 387.30 (M + 1). |
| 15 | 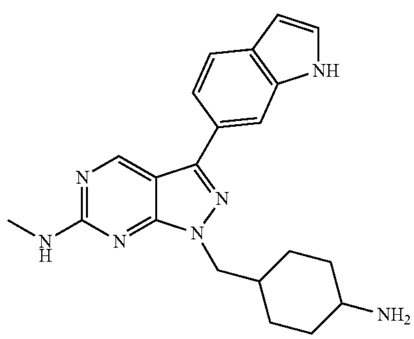 | UNC00000484A | 2:1 | ++ | MS m/z 3769.30 (M + 1). |
| 16 | 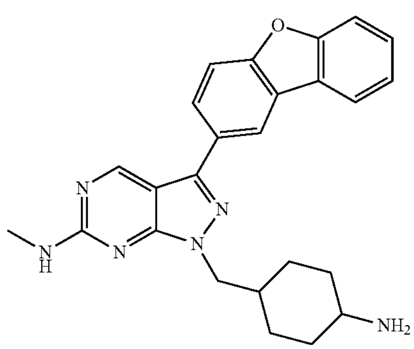 [SMILES: CNc1ncc2c(-c3ccc4oc5ccccc5c4c3)nn(CC3CCC(N)CC3)c2n1] | UNC00000485A | 2:1 | ++ | MS m/z 427.20 (M + 1). |
| 17 | 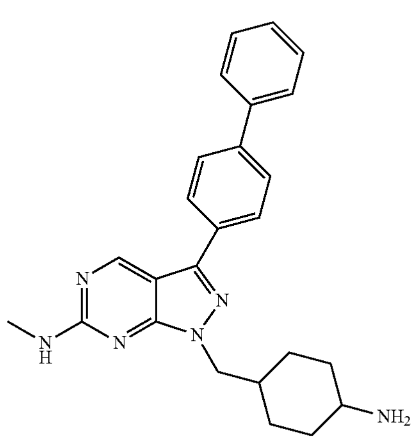 [SMILES: CNc1ncc2c(-c3ccc(-c4ccccc4)cc3)nn(CC3CCC(N)CC3)c2n1] | UNC00000393A | 1.7:1 | +++ | MS m/z 413.30 (M + 1). |

TABLE 1-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 18 | 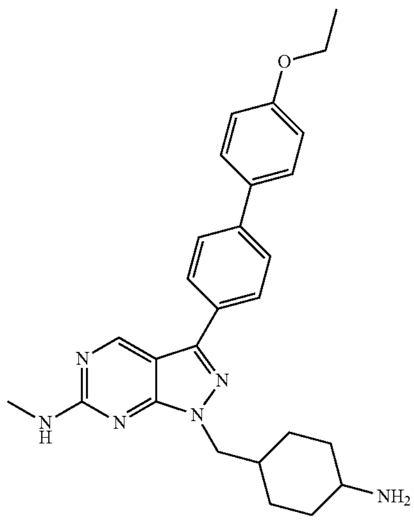 [SMILES: CCOc1ccc(-c2ccc(-c3nn(CC4CCC(N)CC4)c4nc(NC)ncc34)cc2)cc1] | UNC00000483A | 2:1 | +++ | MS m/z 457.30 (M + 1). |
| 19 | 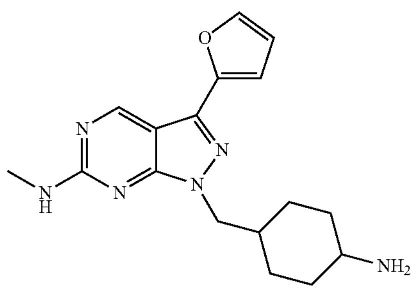 [SMILES: CNc1ncc2c(-c3ccco3)nn(CC3CCC(N)CC3)c2n1] | UNC00000395A | 2:1 | ++ | MS m/z 327.20 (M + 1). |
| 20 | 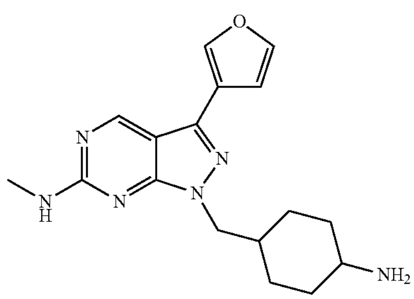 | UNC00000396A | 1.6:1 | ++ | MS m/z 327.20 (M + 1). |
| 21 | 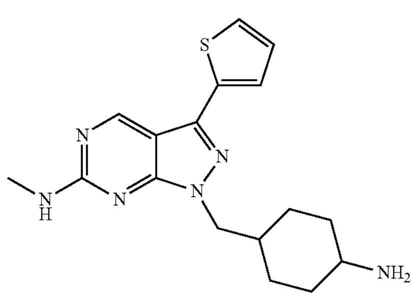 | UNC00000398A | 1.7:1 | ++ | MS m/z 343.20 (M + 1). |

TABLE 1-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 22 | 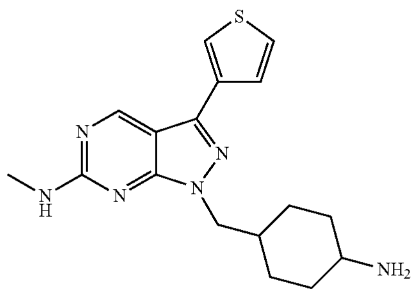 [SMILES: CNc1ncc2c(-c3ccsc3)nn(CC3CCC(N)CC3)c2n1] | UNC00000399A | 0.9:1 | +++ | MS m/z 343.20 (M + 1). |
| 23 | 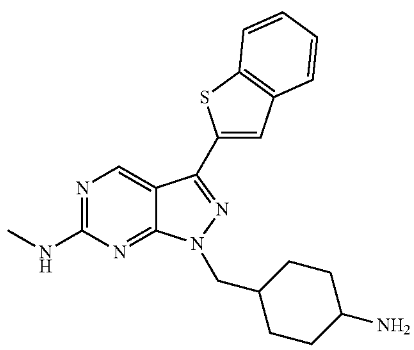 [SMILES: CNc1ncc2c(-c3cc4ccccc4s3)nn(CC3CCC(N)CC3)c2n1] | UNC00000491A | 2:1 | ++ | MS m/z 393.20 (M + 1). |
| 24 | 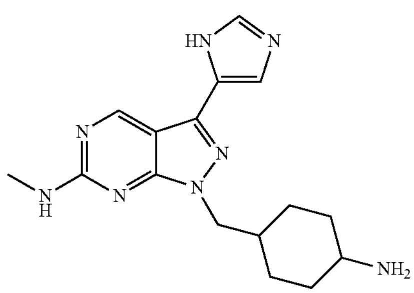 [SMILES: CNc1ncc2c(-c3cnc[nH]3)nn(CC3CCC(N)CC3)c2n1] | UNC00000480A | 2.5:1 | ++ | MS m/z 327.20 (M + 1). |
| 25 | 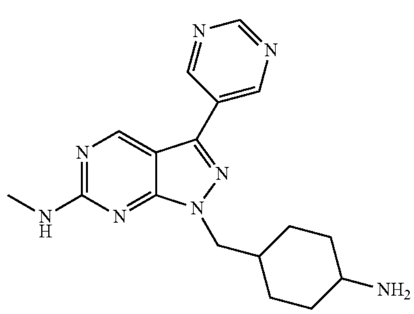 [SMILES: CNc1ncc2c(-c3cncnc3)nn(CC3CCC(N)CC3)c2n1] | UNC00000400A | 1:0 | + | MS m/z 339.20 (M + 1). |

TABLE 1-continued

| | Structure | Compound _ID | dr cis: trans | Mer IC$_{50}$ | Physical Data MS m/z (M + 1) or/and $^1$H NMR (400 MHz, CD$_3$OD) |
|---|---|---|---|---|---|
| 26 | 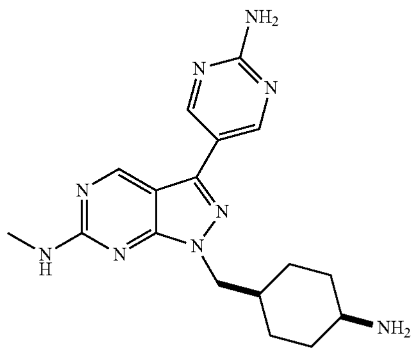 | UNC0000 0410A | 1:0 | + | MS m/z 354.30 (M + 1). |
| 27 | 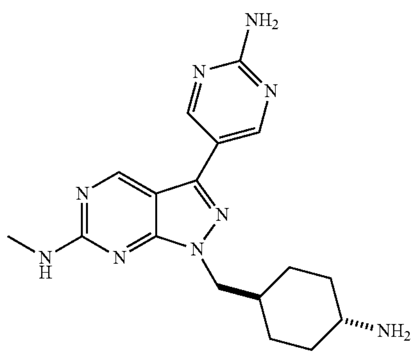 | UNC0000 0411A | 0:1 | ++ | MS m/z 354.30 (M + 1). |
| 28 | 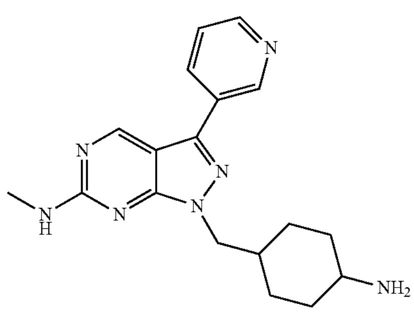 [SMILES: CNc1ncc2c(-c3cccnc3)nn(CC3CCC(N)CC3)c2n1] | UNC0000 0490A | 2:1 | ++ | MS m/z 338.20 (M + 1). |
| 29 | 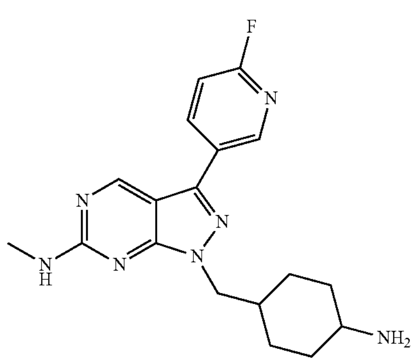 [SMILES: CNc1ncc2c(-c3ccc(F)nc3)nn(CC3CCC(N)CC3)c2n1] | UNC0000 0479A | 2:1 | ++ | MS m/z 356.30 (M + 1). |

TABLE 1-continued
| Structure | Compound_ID | dr cis:trans | Mer IC$_{50}$ | Physical Data MS m/z (M + 1) or/and $^1$H NMR (400 MHz, CD$_3$OD) |
|---|---|---|---|---|
| 30 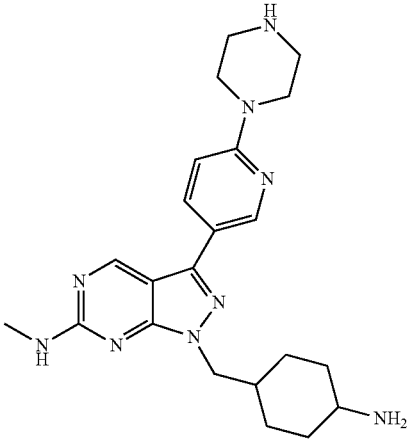 [SMILES: CNc1ncc2c(-c3ccc(N4CCNCC4)nc3)nn(CC3CCC(N)CC3)c2n1] | UNC00000489A | 2:1 | +++ | MS m/z 422.30 (M + 1). |
| 31 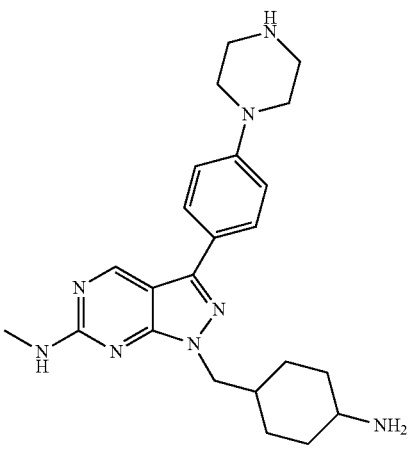 | UNC00000563A | 1.7:1 | +++ | MS m/z 421.30 (M + 1). |
| 32 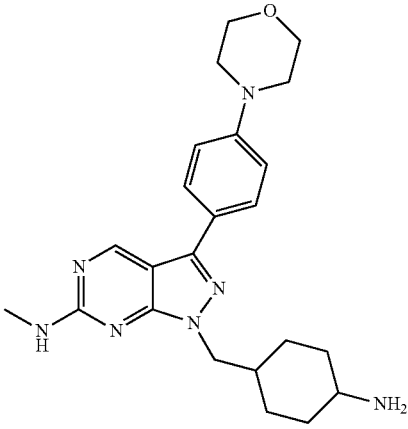 [SMILES: CNc1ncc2c(-c3ccc(N4CCOCC4)cc3)nn(CC3CCC(N)CC3)c2n1] | UNC00000564A | 1.6:1 | +++ | MS m/z 422.30 (M + 1). |

| Structure | Compound_ID | dr cis:trans | Mer IC₅₀ | Physical Data MS m/z (M + 1) or/and ¹H NMR (400 MHz, CD₃OD) |
|---|---|---|---|---|
| 33 | UNC00000569A | 0:1 | ++++ | ¹H NMR (400 MHz, CD₃OD) δ 9.08 (s, 1H), 8.02-7.92 (m, 2H), 7.33-7.20 (m, 2H), 4.22 (m, 2H), 3.51 (t, J = 7.1 Hz, 2H), 3.13-3.00 (m, 1H), 2.15-1.98 (m, 3H), 1.85 (d, J = 12.2 Hz, 2H), 1.74-1.62 (m, 2H), 1.55-1.20 (m, 6H), 1.00 (t, J = 7.4 Hz, 3H); MS m/z 397.30 (M + 1). |
| 34 | UNC00000570A | 0:1 | ++++ | ¹H NMR (400 MHz, CD₃OD) δ 9.16 (s, 1H), 8.76 (d, J = 2.3 Hz, 1H), 8.23 (dd, J = 2.4, 9.0 Hz, 1H), 7.11 (d, J = 9.0 Hz, 1H), 4.02-3.90 (m, 4H), 3.54 (t, J = 7.1 Hz, 2H), 3.40-3.34 (m, 4H), 3.13-3.02 (m, 1H), 2.15-2.01 (m, 3H), 1.87 (d, J = 11.7 Hz, 2H), 1.75-1.65 (m, 2H), 1.55-1.20 (m, 6H), 1.01 (t, J = 7.4 Hz, 3H); MS m/z 464.30 (M + 1). |
| 35 | UNC583A | 0:1 | ++++ | ¹HNMR (400 MHz, CD₃OD) δ 9.14 (s, 1H), 7.90 (d, J = 8.7 Hz, 2H), 7.17 (d, J = 8.8 Hz, 2H), 4.22 (d, J = 6.8 Hz, 2H), 3.60-3.50 (m, 6H), 3.44-3.37 (m, 4H), 3.15-3.07 (m, 1H), 2.14-2.01 (m, 3H), 1.87 (d, J = 11.9 Hz, 2H), 1.75-1.62 (m, 2H), 1.54-1.20 (m, 6H), 1.01 (t, J = 7.4 Hz, 3H); MS m/z 463.35 (M + 1). |

TABLE 1-continued

| Structure | Compound ID | dr cis: trans | Mer IC$_{50}$ | Physical Data MS m/z (M + 1) or/and $^1$H NMR (400 MHz, CD$_3$OD) |
|---|---|---|---|---|
| 36 | UNC582A | 0:1 | ++++ | $^1$H NMR (400 MHz, CD$_3$OD) δ 9.12-9.07 (m, 1H), 7.85 (d, J = 8.8 Hz, 2H), 7.10 (d, J = 8.8 Hz, 2H), 4.21 (d, J = 6.8 Hz, 2H), 3.90-3.81 (m, 4H), 3.53 (t, J = 6.5 Hz, 2H), 3.29-3.23 (m, 4H), 3.12-3.02 (m, 1H), 2.06 (d, J = 11.5 Hz, 3H), 1.86 (d, J = 12.1 Hz, 2H), 1.75-1.64 (m, 2H), 1.54-1.21 (m, 6H), 1.01 (t, J = 7.3 Hz, 3H); MS m/z 464.40 (M + 1). |
| 37 | UNC00000548A | 2:1 | + | MS m/z 351.30 (M + 1). |
| 38 | UNC580A | 0:1 | ++++ | $^1$H NMR (400 MHz, CD$_3$OD) δ 9.06 (s, 1H), 8.01-7.93 (m, 2H), 7.31-7.20 (m, 6H), 7.20-7.13 (m, 1H), 4.17 (d, J = 6.8 Hz, 2H), 3.51 (t, J = 7.1 Hz, 2H), 3.09-2.95 (m, 1H), 2.75 (t, J = 7.5 Hz, 2H), 2.09-1.96 (m, 5H), 1.81 (d, J = 12.4 Hz, 2H), 1.44-1.15 (m, 4H); MS m/z 459.30 (M + 1). |
| 39 | UNC586A | 0:1 | ++++ | $^1$HNMR (400 MHz, CD$_3$OD) δ 9.14 (s, 1H), 8.76 (d, J = 2.2 Hz, 1H), 8.22 (dd, J = 9.0, 2.4 Hz, 1H), 7.31-7.21 (m, 4H), 7.21-7.15 (m, 1H), 7.10 (d, J = 9.0 Hz, 1H), 4.18 (d, J = 6.7 Hz, 2H), 3.99-3.91 (m, 4H), 3.55 (t, J = 7.1 Hz, 2H), 3.41-3.33 (m, 4H), 3.09-2.98 (m, 1H), 2.76 (t, J = 7.5 Hz, 2H), 2.11-1.97 (m, 5H), 1.82 (d, J = 11.7 Hz, 2H), 1.38 (dd, J = 23.7, 11.0 Hz, 2H), 1.23 (dd, J = 25.0, 11.1 Hz, 2H); MS m/z 526.40 (M + 1). |

TABLE 1-continued

| Structure | Compound ID | dr cis:trans | Mer IC$_{50}$ | Physical Data MS m/z (M + 1) or/and $^1$H NMR (400 MHz, CD$_3$OD) |
|---|---|---|---|---|
| 40 | UNC607A | 0:1 | ++++ | $^1$H NMR (400 MHz, CD$_3$OD) δ 9.08 (s, 1H), 7.89 (d, J = 8.9 Hz, 2H), 7.31-7.21 (m, 4H), 7.21-7.14 (m, 3H), 4.17 (d, J = 6.8 Hz, 2H), 3.59-3.50 (m, 6H), 3.44-3.37 (m, 4H), 3.09-2.97 (m, 1H), 2.76 (t, J =7.5 Hz,2H), 2.11-1.95 (m, 5H), 1.82 (d, J = 11.9 Hz, 2H), 1.37 (dd, J = 23.8, 11.5 Hz, 2H), 1.23 (dd, J = 24.7, 11.3 Hz, 2H); MS m/z 525.45 (M + 1). |
| 41 | UNC608A | 0:1 | ++++ | $^1$H NMR (400 MHz, CD$_3$OD) δ 9,04 (s, 1H), 7.84 (d, J = 8.9 Hz, 2H), 7.33-7.21 (m, 4H), 7.21-7.15 (m, 1H), 7.10 (d, J = 8.9 Hz, 2H), 4.16 (d, J = 6.8 Hz, 2H), 3.89-3.82 (m, 4H), 3.52 (t, J = 7.1 Hz, 2H), 3.28-3.22 (m, 4H), 3.08-2.97 (m, 1H), 2.75 (t, J = 7.5 Hz, 2H), 2.10-1.96 (m, 5H), 1.81 (d, J = 12.2 Hz, 2H), 1.37 (dd, J = 24.7, 12.3 Hz, 2H), 1.23 (dd, J = 25.1, 11.0 Hz, 2H); MS m/z 526.40 (M + 1). |
| 42 | UNC595A | 1:0 | +++ | $^1$H NMR (400 MHz, CD$_3$OD) δ 9.09 (s, 1H), 8.76 (d, J = 1.9 Hz, 1H), 8.20 (dd, J = 8.9, 2.4 Hz, 1H), 7.08 (d, J = 9.0 Hz, 1H), 4.23 (d, J = 7.1 Hz, 2H), 4.03-3.90 (m, 4H), 3.88 (bs, 1H), 3.58-3.47 (m, 2H), 3.43-3.33 (m, 4H), 2.22-1.95 (m, 2H), 1.81-1.65 (m, 4H), 1.61-1.37 (m, 7H) 1.05-0.93 (m, 3H); MS m/z 465.40 (M + 1). |

TABLE 1-continued

| Structure | Compound _ID | dr cis: trans | Mer IC$_{50}$ | Physical Data MS m/z (M + 1) or/and $^1$H NMR (400 MHz, CD$_3$OD) |
|---|---|---|---|---|
| 43 | UNC593A | 1:0 | ++++ | $^1$H NMR (400 MHz, CD$_3$OD) δ 9.08 (s, 1H), 7.89 (d, J = 8.9 Hz, 2H), 7.16 (d, J = 8.9 Hz, 2H), 4.22 (d, J = 7.1 Hz, 2H), 3.88 (bs, 1H), 3.62-3.47 (m, 6H), 3.44-3.35 (m, 4H), 2,14 (bs, 1H), 1.81-1.65 (m, 4H), 1.62-1.35 (m, 8H), 1.01 (t, J = 7.4 Hz, 3H); MS m/z 464.40 (M + 1). |
| 44 | UNC594A | 1:0 | +++ | $^1$H NMR (400 MHz, CD$_3$OD) δ 9.05 (s, 1H), 7.84 (d, J = 8.8 Hz, 2H), 7.09 (d, J = 8.8 Hz, 2H), 4.21 (d, J = 7.1 Hz, 2H), 3.91 3.83 (m, 5H), 3.52 (t, J = 7.1 Hz, 2H), 3.28-3.18 (m, 4H), 2.14 (s, 1H), 1.81-1.64 (m, 4H), 1.63-1.36 (m, 8H), 1.00 (t, J = 7.4 Hz, 3H); MS m/z 465.40 (M + 1). |
| 45 | UNC602A | 0:1 | +++ | $^1$H NMR (400 MHz, CD$_3$OD) δ 8.98 (s, 1H), 8.00-7.89 (m, 2H), 7.23 (dd, J = 12.2, 5.4 Hz, 2H), 4.15 (d, J = 7,0 Hz, 2H), 3.51-3.44 (m, 3H), 2.07-1.89 (m, 3H), 1.75-1.60 (m, 4H), 1.51-1.41 (m, 2H), 1.30-1.09 (m, 4H), 0.99 (t, J = 7.4 Hz, 3H); MS m/z 398.30 (M + 1). |

TABLE 1-continued

| Structure | Compound ID | dr cis: trans | Mer IC$_{50}$ | Physical Data MS m/z (M + 1) or/and $^1$H NMR (400 MHz, CD$_3$OD) |
|---|---|---|---|---|
| 46 | UNC603A | 0:1 | ++++ | $^1$H NMR (400 MHz, CD$_3$OD) δ 9.05 (s, 1H), 7.88 (d, J = 8.8 Hz, 2H), 7.16 (d, J = 8.9 Hz, 2H), 4.16 (d, J = 7.0 Hz, 2H), 3.65-3.43 (m, 7H), 3.43-3.35 (m, 4H), 2.08-1.85 (m, 3H), 1.78-1.60 (m, 4H), 1.46 (dq, J = 14.5, 7.4 Hz, 2H), 1.32-1.06 (m, 4H), 0.99 (t, J = 7.4 Hz, 3H); MS m/z 464.30 (M + 1). |
| 47 | UNC600A | N/A | +++ | $^1$H NMR (400 MHz, CD$_3$OD) δ 9.04 (s, 1H), 8.03-7.90 (m, 2H), 7.32-7.18 (m, 2H), 4.30 (d, J = 6.6 Hz, 2H), 3.49 (t, J = 7.1 Hz, 2H), (m, 2H), 2.98 (td, J = 12.8, 2.6 Hz, 2H), 2.45-2.34 (, 1H), 1.93 (d, J = 12.7 Hz, 2H), 1.73-1.51 (m, 4H), 1.45 (dq, J = 14.4, 7.3 Hz, 2H), 0.99 (t, J = 7.4 Hz, 3H); MS m/z 383.30 (M + 1). |
| 48 | UNC606A | N/A | +++ | $^1$H NMR (400 MHz, CD$_3$OD) δ 9.11 (s, 1H), 8,75 (d, J = 2.1 Hz, 1H), 8.20 (dd, J = 9.0, 2.4 Hz, 1H), 7.08 (d, J = 9.0 Hz, 1H), 4.30 (d, J = 6.7 Hz, 2H), 3.99-3.90 (m, 4H), 3.52 (t, J = 7.1 Hz, 2H), 3.46-3.38 (m, 2H), 3.38-3.32 (m, 4H), 3.07-2.91 (m, 2H), 2.47-2.34 (m, 1H), 1.94 (d, J = 12.6 Hz, 2H), 1.68 (dt, J = 14.6, 7.2 Hz, 2H), 1.57 (dd, J = 19.4, 8.0 Hz, 2H), 1.46 (dq, J = 14.5, 7.3 Hz, 2H), 0.99 (t, J = 7.4 Hz, 3H); MS m/z 450.40 (M + 1). |

TABLE 1-continued

| Structure | Compound_ID | dr cis:trans | Mer IC$_{50}$ | Physical Data MS m/z (M + 1) or/and $^1$H NMR (400 MHz, CD$_3$OD) |
|---|---|---|---|---|
| 49 | UNC601A | N/A | ++++ | $^1$H NMR (400 MHz, CD$_3$OD) δ 9.05 (s, 1H), 7.88 (d, J = 8.9 Hz, 2H), 7.16 (d, J = 8.9 Hz, 2H), 4.29 (d, J = 6.7 Hz, 2H), 3.59-3.46 (m, 6H), 3.45-3.37 (m, 6H), 3.04-2.94 (m, 2H), 2.45-2.31 (m, 1H), 1.93 (d, J = 12.4 Hz, 2H), 1.73-1.53 (m, 4H) 1.46 (dq, J = 14.4, 7.3 Hz, 2H), 0.99 (t, J = 7.4 Hz, 3H); MS m/z 449.40 (M + 1). |
| 50 | UNC596A | 1:0 | − | $^1$H NMR (400 MHz, CD$_3$OD) δ 8.88 (s, 1H), 7.93-7.81 (m, 2H), 7.35-7.27 (m, 2H), 7.25-7.11 (m, 5H), 5.41 (bs, 1H), 4.20 (d, J = 7.3 Hz, 2H), 3.97 (s, 1H), 3.61-3.46 (m, 2H), 2.83-2.67 (m, 2H), 2.14 (bs, 1H), 2.07-1.95 (m, 2H), 1.83-1.38 (m, 9H); MS m/z 460.30 (M + 1), |
| 51 | UNC599A | 1:0 | +++ | $^1$H NMR (400 MHz, CD$_3$OD) δ 9.07 (s, 1H), 8.74 (d, J = 2.1 Hz, 1H), 8.19 (dd, J = 8.9, 2.4 Hz, 1H), 7.30-7.20 (m, 4H), 7.18-7.12 (m, 1H), 7.07 (d, J = 9.0 Hz, 1H), 4.19 (d, J = 7.1 Hz, 2H), 3.98-3.90 (m, 4H), 3.88 (s, 1H), 3.53 (t, J = 1.1 Hz, 2H), 3.40-3.32 (m, 4H), 2.74 (t, J = 7.5 Hz, 2H), 2.11 (bs, 1H), 2.07-1.95 (m, 2H), 1.81-1.71 (m, 2H), 1.62-1.38 (m, 6H); MS m/z 527.40 (M + 1). |

TABLE 1-continued

| Structure | Compound_ID | dr cis:trans | Mer IC$_{50}$ | Physical Data MS m/z (M + 1) or/and $^1$H NMR (400 MHz, CD$_3$OD) |
|---|---|---|---|---|
| 52 | UNC597A | 1:0 | +++ | $^1$H NMR (400 MHz, CD$_3$OD) δ 9.04 (s, 1H), 7.88 (d, J = 8.9 Hz, 2H), 7.30-7.18 (m, 4H), 7.19-7.13 (m, 3H), 4.18 (d, J = 7.1 Hz, 2H), 3.87 (bs, 1H), 3.58-3.50 (m, 6H), 3.45-3.35 (m, 4H), 2.74 (t, J = 7.6 Hz, 2H), 2.11 (bs, 1H), 2.06-1.95 (m, 2H), 1.81-1.70 (m, 2H), 1.62-1.35 (m, 6H); MS m/z 526.40 (M + 1). |
| 53 | UNC598A | 1:0 | ++ | $^1$H NMR (400 MHz, CD$_3$OD) δ 9.01 (s, 1H), 7.83 (d, J = 8.9 Hz, 2H), 7.34-7.20 (m, 4H), 7.16 (t, J = 6.9 Hz, 1H), 7.08 (d, J = 8.9 Hz, 2H), 4.17 (d, J = 7.1 Hz, 2H), 3.91-3.83 (m, 5H), 3.51 (t, J = 7.2 Hz, 2H), 3.28-3.19 (m, 4H), 2.74 (t, J = 7.6 Hz, 2H), 2.11 (bs, 1H), 2.07-1.95 (m, 2H), 1.81-1.71 (m, 2H), 1.63-1.36 (m, 6H); MS m/z 526.30 (M + 1). |
| 54 | UNC604A | 0:1 | +++ | $^1$H NMR (400 MHz, CD$_3$OD) δ 8.87 (s, 1H), 7.90-7.83 (m, 2H), 7.33-7.26 (m, 2H), 7.25-7.15 (m, 5H), 4.14 (d, J = 7.1 Hz, 2H), 3.63-3.45 (m, 3H), 2.76 (t, J = 8.0 Hz, 2H), 2.08-1.93 (m, 5H), 1.72 (d, J = 12.7 Hz, 2H), 1.20 (tt, J = 23.8, 11.9 Hz, 4H); MS m/z 460.30 (M + 1). |

TABLE 1-continued

| Structure | Compound_ID | dr cis:trans | Mer IC$_{50}$ | Physical Data MS m/z (M + 1) or/and $^1$H NMR (400 MHz, CD$_3$OD) |
|---|---|---|---|---|
| 55 | UNC605A | 0:1 | ++++ | $^1$H NMR (400 MHz, CD$_3$OD) δ 9.05 (s, 1H), 7.87 (d, J = 8.8 Hz, 2H), 7.30-7.20 (m, 4H), 7.21-7.12 (m, 3H), 4.12 (d, J = 6.8 Hz, 2H), 3.60-3.44 (m, 7H), 3.43-3.34 (m, 4H), 2.73 (t, J = 7.5 Hz, 2H), 2.01 (dt, J = 14.7, 7.4 Hz, 2H), 1.98-1.85 (m, 3H), 1.68 (d, J = 12.7 Hz, 2H), 1.17 (tt, J = 23.9, 11.8 Hz, 4H); MS m/z 526.40 (M + 1). |
| 56 | UNC1056A | 1:0 | +++ | $^1$H NMR (400 MHz, CD$_3$OD) δ 9.07 (s, 1H), 7.83 (d, J = 8.8 Hz, 2H), 7.08 (d, J = 8.8 Hz, 2H), 4.69-4.56 (m, 1H), 3.91-3.82 (m, 4H), 3.78 (dd, J = 13.3, 6.2 Hz, 2H), 3.76-3.66 (m, 1H), 3.29-3.20 (m, 4H), 2.70-2.54 (m, 2H), 2.29-1.99 (m, 6H), 1.60-1.45 (m, 2H); MS m/z 491.3 (M + 1). |
| 57 | UNC1057A | 0:1 | +++ | $^1$H NMR (400 MHz, CD$_3$OD) δ 9.08 (s, 1H), 7.87 (d, J = 8.9 Hz, 2H), 7.10 (d, J = 8.8 Hz, 2H), 4.75-4.63 (m, 1H), 4.08-4.01 (m, 1H), 3.92-3.83 (m, 4H), 3.83-3.75 (m, 2H), 3.30-3.22 (m, 4H), 2.70-2.47 (m, 4H), 2.07-1.96 (m, 2H), 1.87-1.71 (m, 4H)); MS m/z 491.2 (M + 1). |

TABLE 1-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 58 | 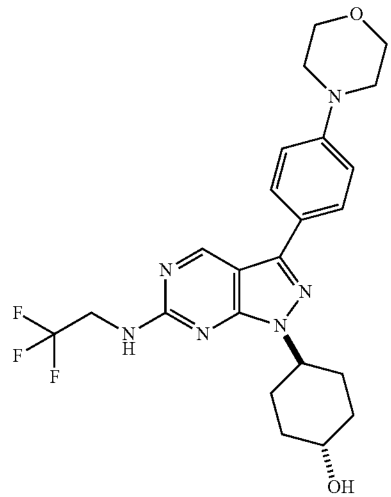 | UNC1067A | 0:1 | +++ | $^1$H NMR (400 MHz, CD$_3$OD) δ 9.06 (s, 1H), 7.87 (d, J = 8.8 Hz, 2H), 7.12 (d, J = 8,7 Hz, 2H), 4.76-4.65 (m, 1H), 4.35-4.21 (m, 2H), 3.92-3.82 (m, 4H), 3.77 (tt, J = 11.0, 4.3 Hz, 1H), 3.31-3.20 (m, 4H), 2.30-2.20 (m, 1H), 2.17-1,89 (m, 5H), 1.60-1.45 (m, 1H), 1.41-1.28 (m, 1H); MS m/z 477.0 (M + 1). |
| 59 | 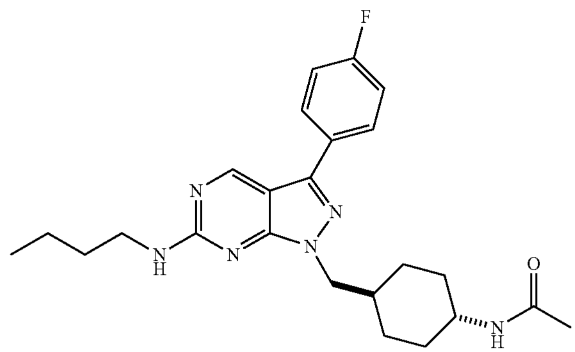 [SMILES: CCCCNc1ncc2c(-c3ccc(F)cc3)nn(C[C@H]3CC[C@H](NC(C)=O)CC3)c2n1] | UNC782A | 0:1 | ++ | $^1$H NMR (400 MHz, CD$_3$OD) δ 8.89 (s, 1H), 7.90-7.81 (m, 2H), 7.18 (t, J = 8.7 Hz, 2H), 4.14 (d, J = 7.0 Hz, 2H), 3.67-3.55 (m, 1H), 3.46 (t, J = 7.1 Hz, 2H), 2.04-1.85 (m, 6H), 1.71 (d, J = 11.4 Hz, 2H), 1.64 (dt, J = 14.8, 7.4 Hz, 2H), 1.43 (dq, J = 14.4, 7.3 Hz, 2H), 1.27-1.09 (m, 4H), 0.96 (t, J = 7.4 Hz, 3H); MS m/z 439.3 (M + 1). |
| 60 | 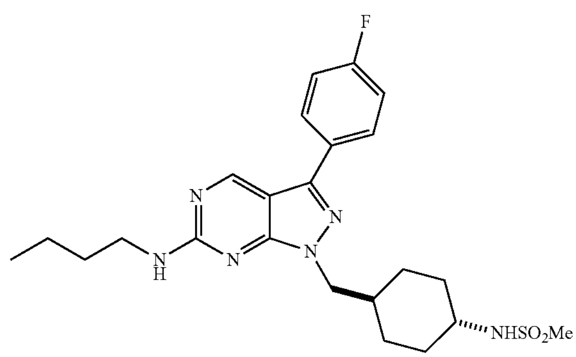 | UNC783A | 0:1 | ++ | $^1$H NMR (400 MHz, CDCl$_3$ + CD$_3$OD) δ 8.98 (s, 1H), 7.94-7.84 (m, 2H), 7.25-7.15 (m, 2H), 4.16 (d, J = 6.9 Hz, 2H), 3.49 (t, J = 7.1 Hz, 2H), 3.22-3.11 (m, 1H), 2.91 (s, 3H), 2.01 (m, 3H), 1.75 (d, J = 11.9 Hz, 2H), 1.66 (dt, J = 14.8, 7.4 Hz, 2H), 1.44 (dq, J = 14.5, 7.3 Hz, 2H), 1.34-1.14 (m, 4H), 0.97 (t, J = 7.4 Hz, 3H); MS m/z 475.3 (M + 1). |
| 61 | 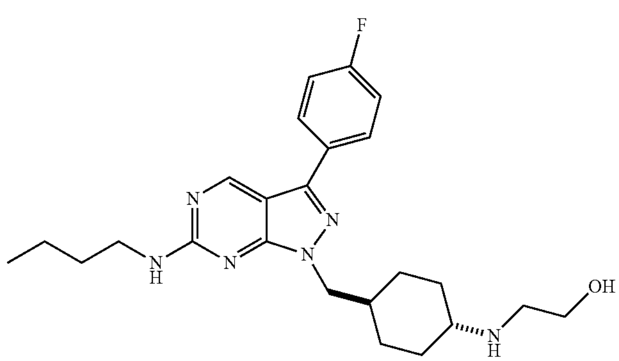 [SMILES: CCCCNc1ncc2c(-c3ccc(F)cc3)nn(C[C@H]3CC[C@H](NCCO)CC3)c2n1] | UNC888A | 0:1 | +++ | $^1$H NMR (400 MHz, CD$_3$OD) δ 9.10 (s, 1H), 7.97 (dd, J = 8.7, 5.3 Hz, 2H), 7.26 (t, J = 8.7 Hz, 2H), 4.22 (d, J = 6.8 Hz, 2H), 3.82-3.74 (m, 2H), 3.51 (t, J = 7.1 Hz, 2H), 3.17-3.05 (m, 3H), 2.17 (d, J = 10.8 Hz, 2H), 2.13-2.02 (m, 1H), 1.88 (d, J = 12.3 Hz, 2H), 1.68 (dt, J = 14.8, 7.3 Hz, 2H), 1.54-1.36 (m, 4H), 1.35-1.20 (m, 2H), 1.00 (t, J = 7.4 Hz, 3H); MS m/z 441.3 (M + 1). |

TABLE 1-continued

| Structure | Compound_ID | dr cis:trans | Mer IC$_{50}$ | Physical Data MS m/z (M + 1) or/and $^1$H NMR (400 MHz, CD$_3$OD) |
|---|---|---|---|---|
| 62 | UNC886A | 0:1 | +++ | $^1$H NMR (400 MHz, CD$_3$OD) δ 9.05 (s, 1H), 7.83 (d, J = 8.7 Hz, 2H), 7.08 (d, J = 8.7 Hz, 2H), 4.20 (d, J = 6.8 Hz, 2H), 3.93-3.80 (m, 4H), 3.58 (t, J = 7.0 Hz, 2H), 3.28-3.19 (m, 4H), 3.11-2.99 (m, 1H), 2.38-2.21 (m, 2H), 2.05 (d, J = 8.8 Hz, 3H), 1.96 (dt, J = 14.6, 7.2 Hz, 2H), 1.83 (d, J = 12.1 Hz, 2H), 1.47-1.17 (m, 4H); MS m/z 518.3 (M + 1). |
| 63 | UNC887A | 0:1 | +++ | $^1$H NMR (400 MHz, CD$_3$OD) δ 9.00 (s, 1H), 7.82 (d, J = 8.8 Hz, 2H), 7.29-7.18 (m, 2H), 7.08 (d, J = 8.8 Hz, 2H), 7.03-6.95 (m, 2H), 4.14 (d, J = 6.8 Hz, 2H), 3.91-3.79 (m, 4H), 3.49 (t, J = 7.1 Hz, 2H), 3.28-3.18 (m, 4H), 3.10-2.94 (m, 1H), 2.73 (t, J = 7.5 Hz, 2H), 2.00 (dt, J = 14.5, 7.9 Hz, 5H), 1.80 (d, J = 12.2 Hz, 2H), 1.37 (dd, J = 23.5, 11.0 Hz, 2H), 1.21 (dd, J = 25.2, 11.1 Hz, 2H); MS m/z 544.4 (M + 1). |

Example 2

The R$^2$ Position 1-((trans-4-Aminocyclohexyl)methyl)-N-methyl-3-phenyl-1H-pyrazolo[3,4-d]pyrimidin-6-amine General Procedure B:

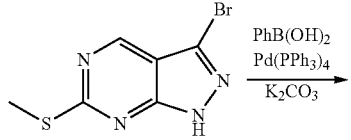

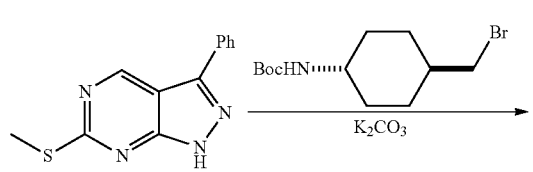

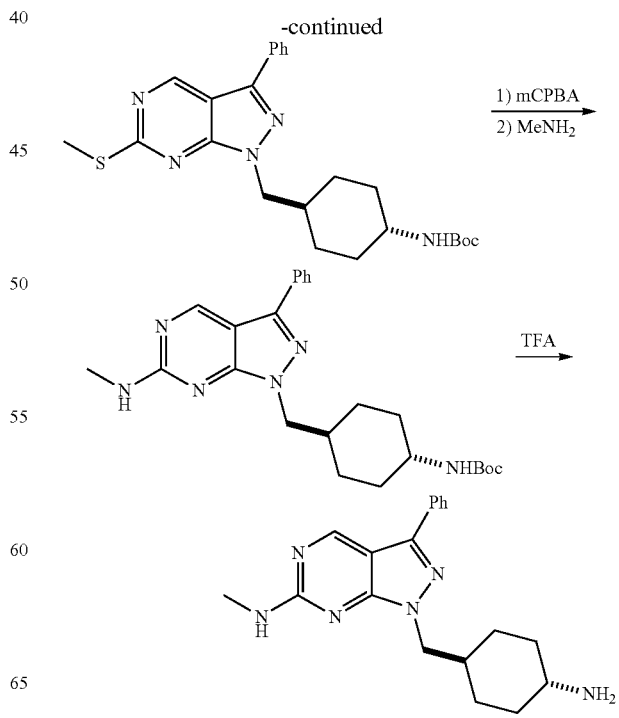

6-(Methylthio)-3-phenyl-1H-pyrazolo[3,4-d]pyrimidine

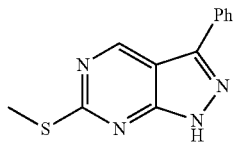 [SMILES: CSc1ncc2c(-c3ccccc3)n[nH]c2n1]

A microwave tube was charged with 3-bromo-6-(methylthio)-1H-pyrazolo[3,4-d]pyrimidine (1.0 g, 4.0 mmol), phenylboronic acid (1.5 g, 12 mmol), potassium phosphonate (2.5 g, 12 mmol), tetrakis(triphenylphosphine)palladium (0.35 g, 0.30 mmol), dioxane (16 mL) and water (4 mL). The mixture was heated in microwave at 150° C. for 20 min. The reaction mixture was poured into water. The aqueous layer was extracted with EtOAc (10×). The combined organic layer was dried ($Na_2SO_4$), concentrated, and purified to provide 6-(methylthio)-3-phenyl-1H-pyrazolo[3,4-d]pyrimidine (0.85 g, 87%) as a white solid. MS m/z 243.1 $[M+H]^+$.

tert-Butyl trans-4-((6-(methylthio)-3-phenyl-1H-pyrazolo[3,4-d]pyrimidin-1-yl)methyl)cyclohexylcarbamate

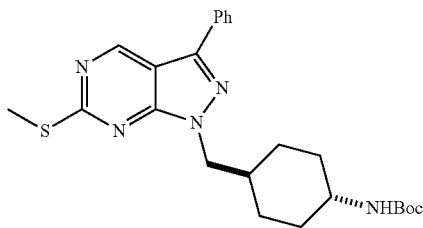

To a suspension of trans-4-aminocyclohexanecarboxylic acid (5.0 g, 35 mmol) in methanol (50 mL) was added thionyl chloride (2.9 mL, 40 mmol) dropwisely at 0° C. The white suspension was dissolved. After being stirred at room temperature for 4.5 h, the solution was concentrated and white solid was obtained. Methylene chloride was added and then evaporated twice to remove trace amount of thionyl chloride. A suspension of the solid in methylene chloride (60 mL) was added triethyl amine (5.4 mL, 38 mmol). A clear solution was obtained. The solution was cooled to 0° C. and Boc anhydride (8.83 mL, 38 mmol) was added slowly. The reaction mixture was stirred at room temperature for 5 h, then poured into an aqueous sodium bicarbonate solution. The mixture was extracted with methylene chloride (3×), dried ($Na_2SO_4$), and concentrated. The crude mixture was purified by Isco to give trans-methyl 4-(tert-butoxycarbonylamino)cyclohexane carboxylate (9.0 g, 100%) as a white solid, $^1H$ NMR (400 MHz, $CDCl_3$) δ 4.37 (s, 1H), 3.66 (s, 3H), 3.44 (d, J=27.3 Hz, 1H), 2.22 (tt, J=12.1, 3.4 Hz, 1H), 2.03 (dd, J=24.0, 13.2 Hz, 4H), 1.56-1.47 (m, 2H), 1.45 (d, J=12.2 Hz, 9H), 1.10 (qd, J=12.7, 3.1 Hz, 2H). $^{13}C$ NMR (100 MHz, $CDCl_3$) δ 175.8, 155.1, 79.2, 77.3, 77.0, 76.7, 51.6, 49.0, 42.4, 32.5, 28.4, 27.8.

A solution of trans-methyl 4-(tert-butoxycarbonylamino) cyclohexanecarboxylate (9.0 g, 35 mmol) in THF (70 mL) was added slowly a 2.0 M solution of $LiAH_4$ in THF (20 mL, mmol) at −78° C. The reaction was warmed slowly to room temperature (over 4 h), and quenched by dropwise addition of water (5 mL), followed by addition of NaOH (5 mL) and $Na_2SO_4$. The mixture was stirred for 20 min and filtered. The filtrate was dried ($Na_2SO_4$), and concentrated. The crude mixture was purified by Isco to provide tert-butyl trans-4-(hydroxymethyl)cyclohexylcarbamate (5.5 g, 69%) as a white solid.

A solution of tert-butyl trans-4-(hydroxymethyl)cyclohexylcarbamate (5.5 g, 24 mmol) and carbon tetrabromide (9.9 g, 30 mmol) in methylene chloride (120 mL) was added triphenylphosphine (7.5 g, 29 mmol) in three portions at 0° C. The solution was stirred at room temperature for 4 h. After evaporation of solvent, a mixture of EtOAc and hexanes (1:1) was added. The resulting white solid was filtered off. The filtrate was concentrated and purified by Isco to provide tert-butyl trans-4-(bromomethyl)cyclohexyl carbamate (6.5 g, 93%) as a white solid. $^1H$ NMR (400 MHz, $CD_3OD$) δ 3.31 (d, J=6.4 Hz, 2H), 3.25 (dd, J=15.0, 6.9 Hz, 1H), 1.91 (d, J=9.6 Hz, 4H), 1.64-1.50 (m, 1H), 1.42 (s, 9H), 1.28-1.05 (m, 4H); $^{13}C$ NMR (100 MHz, $CD_3OD$) δ 157.8, 79.8, 50.8, 40.7, 40.3, 33.4, 31.4, 28.8.

A microwave tube was charged with 6-(methylthio)-3-phenyl-1H-pyrazolo[3,4-d]pyrimidine (0.073 g, 0.30 mmol), potassium carbonate (0.14 g, 0.90 mmol), and DMSO (1 mL). The resulting mixture was stirred for 20 min, then was added a solution of tert-butyl trans-4-(bromomethyl)cyclohexylcarbamate (0.10 g, 0.36 mmol) in THF (2 mL). The resulting mixture was heated at 150° C. for 10 min in microwave. The reaction mixture was poured into water and extracted with $Et_2O$ (3×). The combined ether layer was dried ($Na_2SO_4$) and concentrated. The crude mixture was purified by Isco to provide tert-butyl trans-4-((6-(methylthio)-3-phenyl-1H-pyrazolo[3,4-d]pyrimidin-1-yl)methyl)cyclohexylcarbamate (0.12 g, 88%) as a white solid. $^1H$ NMR (400 MHz, $CDCl_3$) δ 9.11 (s, 1H), 7.90 (d, J=7.2 Hz, 2H), 7.55-7.44 (t, J=6.8 Hz, 2H), 7.41 (t, J=7.3 Hz, 1H), 4.37 (bs, 1H), 4.27 (d, J=7.1 Hz, 2H), 3.37 (bs, 1H), 2.61 (s, 3H), 2.09-1.89 (m, 3H), 1.67 (d, J=12.1 Hz, 2H), 1.39 (s, 9H), 1.19 (dd, J=24.4, 10.8 Hz, 2H), 1.04 (ddd, J=25.4, 12.7, 2.9 Hz, 2H); $^{13}C$ NMR (100 MHz, $CDCl_3$) δ 170.1, 155.3, 154.8, 152.3, 144.3, 132.2, 129.2, 127.1, 109.3, 79.3, 52.5, 49.7, 37.7, 32.9, 29.6, 28.5, 12.5; MS m/z 454.2 $[M+H]^+$.

tert-Butyl trans-4-((6-(methylamino)-3-phenyl-1H-pyrazolo[3,4-d]pyrimidin-1-yl)methyl)cyclohexylcarbamate

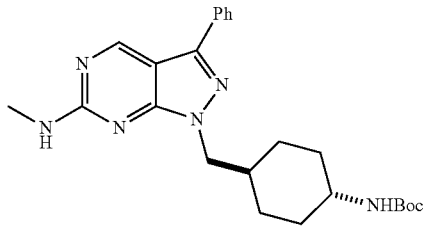

To a solution of tert-butyl trans-4-((6-(methylthio)-3-phenyl-1H-pyrazolo[3,4-d]pyrimidin-1-yl)methyl)cyclohexylcarbamate (0.14 g, 0.3 mmol) in methylene chloride (5 mL) was added meta-chloroperoxybenzoic acid (0.20 g, 0.9 mmol) at room temperature. After stirring at room temperature for 2 h, the light purple solution was quenched with a 1.0 N aqueous solution of NaOH. The aqueous layer was extracted with EtOAc (3×). The organic layers were combined, dried ($Na_2SO_4$), and concentrated. The residue was dissolved in THF (1.5 mL), followed by the addition of a 2.0 M methylamine solution in THF (1.5 mL, 3.0 mmol). The resulting solution was heated at 60° C. for 2 h, cooled to room temperature, and concentrated. The crude mixture was purified by Isco to provide tert-butyl trans-4-((6-(methylamino)-3-phenyl-1H-pyrazolo[3,4-d]pyrimidin-1-yl)methyl)cyclohexyl carbamate (0.10 g, 76%) as a white solid.

1-((trans-4-Aminocyclohexyl)methyl)-N-methyl-3-phenyl-1H-pyrazolo[3,4-d]pyrimidin-6-amine

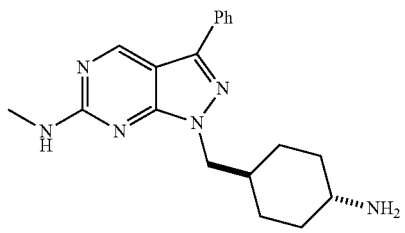

To a solution of tert-butyl trans-4-((6-(methylamino)-3-phenyl-1H-pyrazolo[3,4-d]pyrimidin-1-yl)methyl)cyclohexylcarbamate (0.082 g, 0.19 mmol) in methylene chloride (3 mL) was added trifluoroacidic acid (0.60 mL). The reaction mixture was stirred at room temperature for 2 h, concentrated and basified by a 7.0 M aqueous solution of ammonia to pH 12. After evaporation, the residue was purified by Isco to provide 1-((trans-4-aminocyclohexyl)methyl)-N-methyl-3-phenyl-1H-pyrazolo[3,4-d]pyrimidin-6-amine (UNC00000545A) (0.051 g, 80%) as a white solid. $^1$H NMR (400 MHz, CD$_3$OD) δ 8.94 (s, 1H), 7.94-7.83 (m, 2H), 7.55-7.44 (m, 2H), 7.44-7.36 (m, 1H), 4.16 (d, J=7.5 Hz, 2H), 3.06-2.91 (m, 1H), 2.99 (s, 3H), 2.13-1.93 (m, 3H), 1.78 (d, J=12.7 Hz, 2H), 1.45-1.14 (m, 4H); $^{13}$C NMR (100 MHz, CD$_3$OD) δ 162.87, 157.72, 154.93, 145.73, 133.64, 130.01, 129.95, 127.97, 52.28, 51.32, 49.64, 49.43, 49.21, 49.00, 48.79, 48.57, 48.36, 38.38, 31.91, 29.71, 28.52; MS m/z 337.3 [M+H]$^+$.

Table 2 describes compounds prepared following procedures described in Example 2 (General Procedure B), using appropriate reagents.

TABLE 2

| | Structure | Compound_ID | dr cis: trans | Mer IC$_{50}$ | Physical Data MS m/z (M + 1) or/and $^1$H NMR (400 MHz, CD$_3$OD) |
|---|---|---|---|---|---|
| 1 | 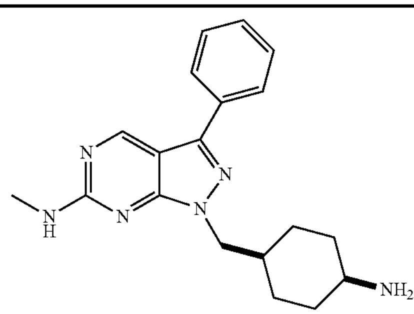 | UNC 00000544A | 1:0 | ++ | $^1$H NMR (400 MHz, CD$_3$OD) δ 8.94 (s, 1H), 7.87 (d, J = 6.8 Hz, 2H), 7.48 (dd, J = 7.4, Hz, 2H), 7.41 (t, J = 7.3 Hz, 1H), 4.30 (d, J = 7.6 Hz, 2H), 3.06 (dt, J = 11.7, 5.9 Hz, 1H), 3.00 (s, 3H), 2.36-2.24 (m, 1H), 1.76-1.71 (m, 4H), 1.64-1.45 (m, 4H); MS m/z 337.30 (M + 1). |
| 2 | 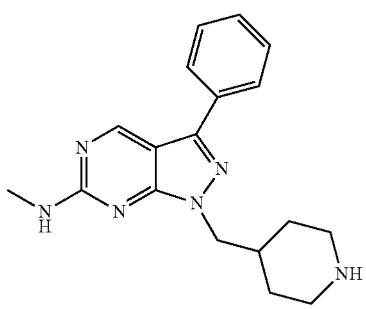 [SMILES: CNc1ncc2c(-c3ccccc3)nn(CC3CCNCC3)c2n1] | UNC 00000171A | N/A | ++ | $^1$HNMR (300 MHz, CD$_3$OD) δ 8.98 (s, 1H), 7.92 (d, J = 8.2 Hz, 2H), 7.62-7.33 (m, 3H), 4.31 (d, J = 6.8 Hz, 2H), 3.39 (d, J = 13.1 Hz, 2H), 3.00 (s, 3H), 3.05-2.88 (m, 2H), 2.38 (bs, 1H), 1.91 (d, J = 12.2 Hz, 2H), 1.58 (dd, J = 23.0, 12.0 Hz, 2H); MS m/z 323.20 (M + 1). |
| 3 | 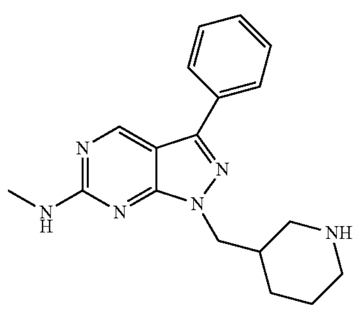 [SMILES: CNc1ncc2c(-c3ccccc3)nn(CC3CCCNC3)c2n1] | UNC 00000263A | N/A | ++ | $^1$H NMR (400 MHz, CD$_3$OD) δ 9.06 (s, 1H), 7.92 (d, J = 7.3 Hz, 2H), 7.56-7.40 (m, 3H), 4.47-4.21 (m, 2H), 3.35 (t, J = 12.4 Hz, 2H), 3.04 (s, 3H), 2.89 (dd, J = 22.3, 10.2 Hz, 2H), 2.50 (bs, 1H), 1.95 (dd, J = 21.6, 8.5 Hz, 2H), 1.83-1.65 (m, 1H), 1.52-1.33 (m, 1H); MS m/z 323.30 (M + 1). |

TABLE 2-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 4 | 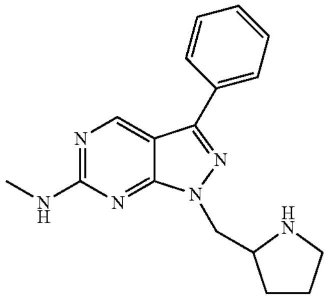 [SMILES: CNc1ncc2c(-c3ccccc3)nn(CC3CCCN3)c2n1] | UNC 00000264A | N/A | + | $^1$H NMR (400 MHz, CD$_3$OD) δ 9.05 (s, 1H), 7.97 (d, J = 12, 2H), 7.57-7.35 (m, 3H), 4.77 (dd, J = 15.0, 3.7 Hz, 1H), 4.56 (dd, J = 15.0, 8.4 Hz, 1H), 4.18-4.08 (m, 1H), 3.47-3.32 (m, 2H), 3.02 (s, 3H), 2.38-2.30 (m, 1H), 2.17-1.99 (m, 2H), 1.99-1.86 (m, 1H); MS m/z 309.20 (M + 1). |
| 5 | 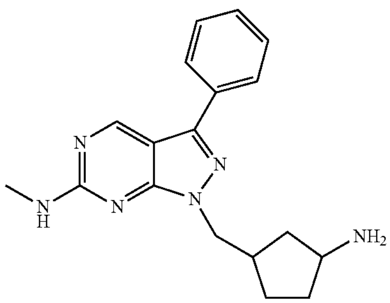 [SMILES: CNc1ncc2c(-c3ccccc3)nn(CC3CCC(N)C3)c2n1] | UNC 00000462A | 1:0 | ++ | MS m/z 323.20 (M + 1). |
| 6 | 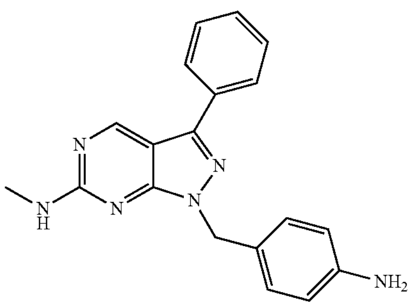 [SMILES: CNc1ncc2c(-c3ccccc3)nn(Cc3ccc(N)cc3)c2n1] | UNC 00000414A | N/A | ++ | $^1$H NMR (400 MHz, CD$_3$OD) δ 9.10 (s, 1H), 7.88 (d, J = 8.0 Hz, 2H), 7.60-7.52 (d, 2H), 7.52-7.39 (m, 3H), 7.33 (dt, J = 19.3, 9.7 Hz, 2H), 5.58 (s, 2H), 3.05 (s, 3H); MS m/z 331.20 (M + 1). |
| 7 | 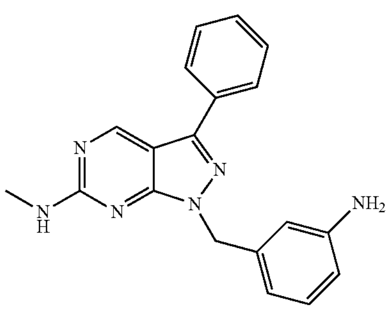 [SMILES: CNc1ncc2c(-c3ccccc3)nn(Cc3cccc(N)c3)c2n1] | UNC 00000415A | N/A | ++ | $^1$H NMR (400 MHz, CD$_3$OD) δ 9.09 (s, 1H), 7.98-7.88 (m, 2H), 7.56-7.40 (m, 5H), 7.31 (s, 1H), 7.29-7.22 (m, 1H), 5.60 (s, 2H), 3.04 (s, 3H); MS m/z 331.20 (M + 1). |
| 8 | 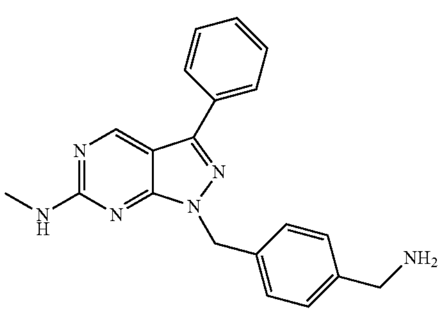 [SMILES: CNc1ncc2c(-c3ccccc3)nn(Cc3ccc(CN)cc3)c2n1] | UNC 00000581A | N/A | ++ | $^1$H NMR (400 MHz, CD$_3$OD) δ 9.12 (s, 1H), 7.90 (d, J = 7.3 Hz, 2H), 7.54-7.37 (m, 7H), 5.55 (s, 2H), 4.09 (s, 2H), 3.07 (s, 3H); MS m/z 345.20 (M + 1). |

TABLE 2-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 9 | 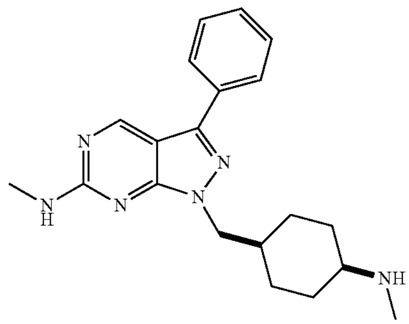 | UNC 00000514A | 2.2:1 | ++ | MS m/z 351.30 (M + 1). |
| 10 | 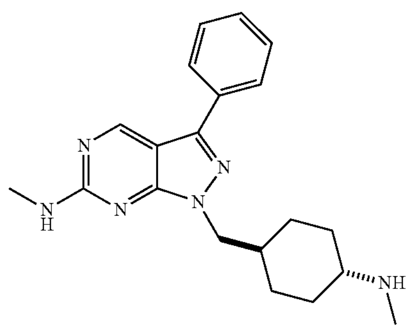 | UNC 00000515A | 0:1 | ++ | $^1$H NMR (400 MHz, CD$_3$OD) δ 8.93 (s, 1H), 7.88 (d, J = 7.9 Hz, 2H), 7.47 (t, J = 7.6 Hz, 2H), 7.40 (t, J = 7.0 Hz, 1H), 4.18 (d, J = 6.9 Hz, 2H), 3.04-2.90 (m, 1H), 2.98 (s, 3H), 2.64 (s, 3H), 2.14-2.04 (m, 3H), 1.82 (d, J = 12.2 Hz, 2H), 1.44-1.11 (m, 5H); MS m/z 351.30 (M + 1). |
| 11 | 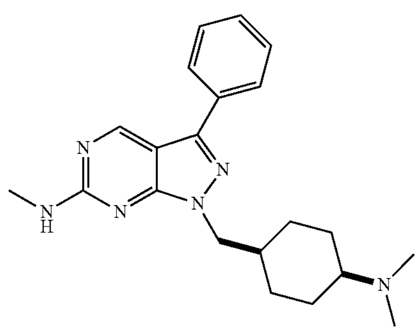 | UNC 00000516A | 1:0 | ++ | $^1$H NMR (400 MHz, CD$_3$OD) δ 9.17 (s, 1H), 7.95 (d, J = 7.8 Hz, 2H), 7.60-7.43 (m, 3H), 4.26 (d, J = 6.8 Hz, 2H), 3.20 (t, J = 12.1 Hz, 1H), 3.07 (d, J = 5.9 Hz, 3H), 2.82 (s, 6H), 2.10 (d, J = 11.9 Hz, 3H), 1.94 (d, J = 13.1 Hz, 2H), 1.53 (dd, J = 24.8, 12.7 Hz, 2H), 1.32 (dd, J = 23.2, 12.0 Hz, 2H); MS m/z 365.30 (M + 1). |
| 12 | 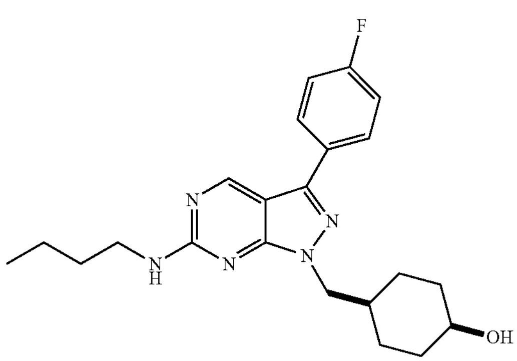 [SMILES: CCCCNc1ncc2c(-c3ccc(F)cc3)nn(C[C@H]3CC[C@@H](O)CC3)c2n1] | UNC 00000568A | 1:0 | +++ | $^1$H NMR (400 MHz, CD$_3$OD) δ 8.92 (s, 1H), 8.00-7.85 (m, 2H), 7.22 (t, J = 8.8 Hz, 2H), 4.19 (d, J = 7.2 Hz, 2H), 3.85 (s, 1H), 3.45 (t, J = 7.1 Hz, 2H), 2.20-2.10 (m, 1H), 1.82-1.71 (m, 2H), 1.70-1.60 (m, 2H), 1.59-1.32 (m, 8H), 0.98 (t, J = 7.4 Hz, 3H); MS m/z 398.30 (M + 1). |

TABLE 2-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 13 | 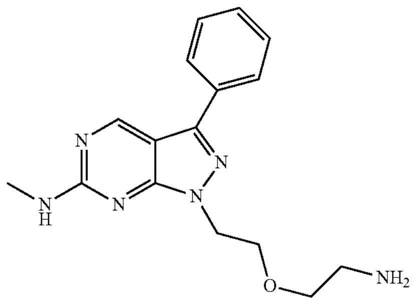 | UNC 00000556A | N/A | + | $^1$H NMR (400 MHz, CD$_3$OD) δ 9.14-9.11 (m, 1H), 7.99-7.91 (m, 2H), 7.58-7.46 (m, 3H), 4.58 (t, J = 5.4 Hz, 2H), 4.07 (t, J = 5.4 Hz, 2H), 3.78-3.71 (m, 2H), 3.12-3.04 (m, 5H); MS m/z 313.20 (M + 1). |
| 14 | 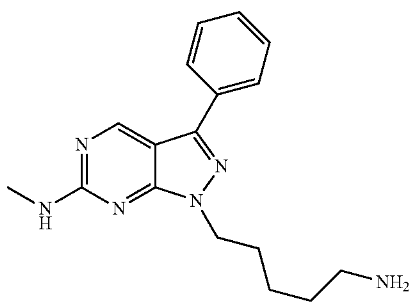 [SMILES: CNc1ncc2c(-c3ccccc3)nn(CCCCCN)c2n1] | UNC 00000547A | N/A | ++ | $^1$H NMR (400 MHz, CD$_3$OD) δ 9.15 (s, 1H), 7.96 (d, J = 7.2 Hz, 2H), 7.58-7.46 (m, 3H), 4.40 (t, J = 6.8 Hz, 2H), 3.08 (s, 3H), 2.92 (t, J = 7.6 Hz, 2H), 2.09-1.99 (m, 2H), 1.79-1.69 (m, 2H), 1.54-1.42 (m, 2H); MS m/z 311.20 (M + 1). |
| 15 | 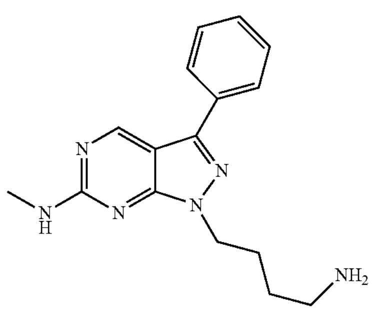 [SMILES: CNc1ncc2c(-c3ccccc3)nn(CCCCN)c2n1] | UNC 00000585A | N/A | ++ | $^1$H NMR (400 MHz, CD$_3$OD) δ 9.17 (s, 1H), 7.98-7.92 (m, 2H), 7.56-7.46 (m, 3H), 4.43 (t, J = 6.6 Hz, 2H), 3.08 (s, 3H), 3.01 (t, J = 7.7 Hz, 2H), 2.12-2.02 (m, 2H), 1.77-1.66 (m, 2H); MS m/z 297.20 (M + 1). |
| 16 | 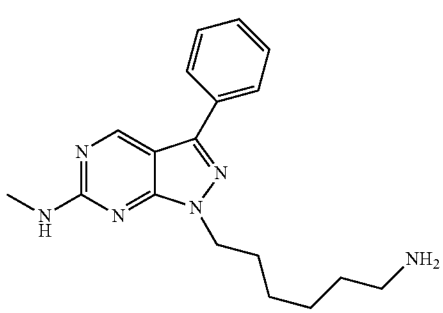 [SMILES: CNc1ncc2c(-c3ccccc3)nn(CCCCCCN)c2n1] | UNC 00000584A | N/A | ++ | $^1$H NMR (400 MHz, CD$_3$OD) δ 9.15 (s, 1H), 7.94 (dd, J = 1.4, 8.1 Hz, 2H), 7.56-7.46 (m, 3H), 4.37 (t, J = 6.9 Hz, 2H), 3.08 (s, 3H), 2.90 (t, J = 7.6 Hz, 2H), 2.06-1.95 (m, 2H), 1.69-1.60 (m, 2H), 1.53-1.38 (m, 4H); MS m/z 325.30 (M + 1), |

TABLE 2-continued

| Structure | Compound_ID | dr cis: trans | Mer IC$_{50}$ | Physical Data MS m/z (M + 1) or/and $^1$H NMR (400 MHz, CD$_3$OD) |
|---|---|---|---|---|
| 17 | UNC 00000571A | N/A | ++ | $^1$H NMR (400 MHz, CD$_3$OD) $^1$HNMR(400 MHz, cd$_3$od) δ 9.08 (s, 1H), 7.94 (d, J = 7.1 Hz, 2H), 7.57-7.43 (m, 3H), 4.45 (t, J = 6.7 Hz, 2H), 3.42-3.34 (m, 2H), 3.04 (s, 3H), 2.97-2.86 (m, 2H), 2.13 (d, J = 14.3 Hz, 2H), 1.98 (q, J = 6.7 Hz, 2H), 1.66-1.54 (m, 1H), 154-1.38 (m, 2H); MS m/z 337.20 (M + 1). |

Example 3

The R$^3$ Position tert-Butyl-4-((3-bromo-6-(methylthio)-1H-pyrazolo[3,4-d]pyrimidin-1-yl)methyl)cyclohexylcarbamate General Procedure C:

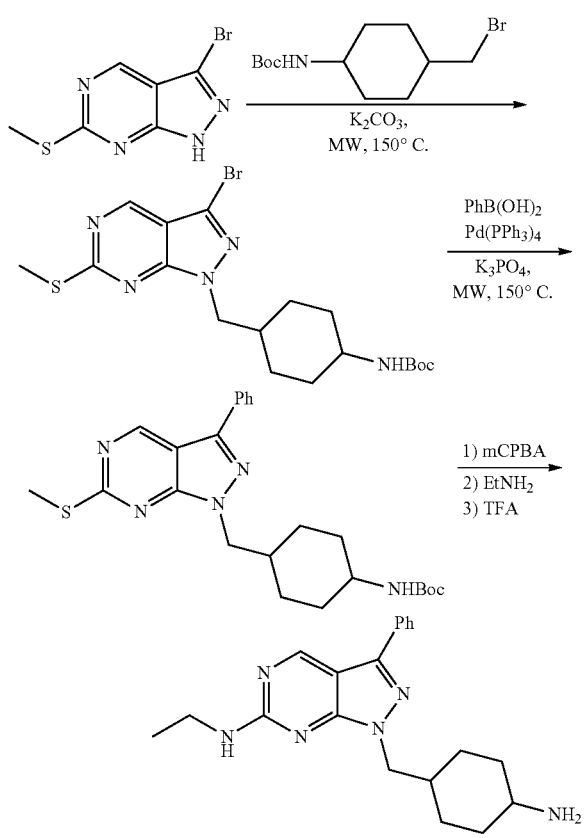

tert-Butyl-4-((3-bromo-6-(methylthio)-1H-pyrazolo[3,4-d]pyrimidin-1-yl)methyl)cyclohexylcarbamate

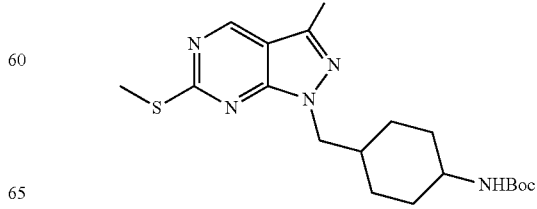

A 10 mL microwave tube was charged with 3-bromo-6-(methylthio)-1H-pyrazolo[3,4-d]pyrimidine (0.2 g, 0.8 mmol), potassium carbonate (0.34 g, 2.4 mmol), and DMSO (1.5 mL). The resulting mixture was stirred for 20 min, then tert-butyl trans-4-(bromomethyl)cyclohexylcarbamate (0.29 g, 1.0 mmol) and THF (3 mL) were added. The resulting mixture was heated at 150° C. for 10 min in microwave. The reaction mixture was poured into water and extracted with Et$_2$O (3×). The combined ether layers were dried (Na$_2$SO$_4$), concentrated, and purified by Isco to give tert-Butyl-4-((3-bromo-6-(methylthio)-1H-pyrazolo[3,4-d]pyrimidin-1-yl)methyl)cyclohexyl carbamate (0.31 g, 85%) as a white solid. MS m/z 478.1 [M+Na]$^+$.

tert-Butyl-4-((6-(methylthio)-3-phenyl-1H-pyrazolo[3,4-d]pyrimidin-1-yl)methyl)cyclohexylcarbamate A microwave tube was charged with tert-butyl trans-4-((3-bromo-6-(methylthio)-1H-pyrazolo[3,4-d]pyrimidin-1-yl)methyl)cyclohexylcarbamate (0.046 g, 0.1 mmol), phenylboronic acid (0.037 g, 0.3 mmol), potassium phosphonate (0.063 g, 0.3 mmol), tetrakis(triphenylphosphine)palladium (0.012 g, 0.01 mmol), dioxane (2 mL) and water (0.5 mL). The mixture was heated in microwave at 150° C. for 10 min. The reaction mixture was poured into water. The aqueous layer was extracted with Et₂O (3×). The combined organic layers were dried (Na₂SO₄), concentrated, and purified by Isco to give tert-Butyl-4-((6-(methylthio)-3-phenyl-1H-pyrazolo[3,4-d]pyrimidin-1-yl)methyl)cyclohexylcarbamate (0.040 g, 88%) as a white solid. MS m/z 454.3 [M+H]⁺.

tert-butyl 4-((6-(methylamino)-3-phenyl-1H-pyrazolo[3,4-d]pyrimidin-1-yl)methyl)cyclohexylcarbamate

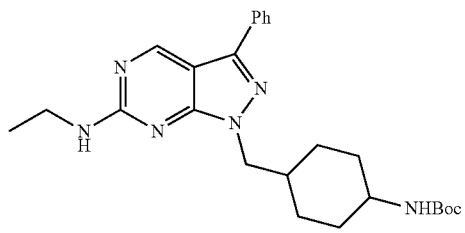 [SMILES: CCNc1ncc2c(-c3ccccc3)nn(CC3CCC(NC(=O)OC(C)(C)C)CC3)c2n1]

To a solution of tert-Butyl-4-((6-(methylthio)-3-phenyl-1H-pyrazolo[3,4-d]pyrimidin-1-yl)methyl)cyclohexylcarbamate (0.14 g, 0.3 mmol) in methylene chloride (5 mL) was added meta-chloroperoxybenzoic acid (0.20 g, 0.9 mmol) at room temperature. After stirring at room temperature for 2 h, the light purple solution was quenched with a 1.0 N aqueous solution of NaOH. The aqueous layer was extracted with EtOAc (3×). The organic layers were combined, dried (Na₂SO₄), and concentrated. The residue was dissolved in THF (1 mL), followed by the addition of ethylamine (1.5 mL, 2.0 M in THF, 3 mmol). The resulting solution was heated at 60° C. for 2 h, cooled to room temperature, and concentrated. The crude mixture was purified by Isco to provide tert-butyl 4-((6-(methylamino)-3-phenyl-1H-pyrazolo[3,4-d]pyrimidin-1-yl)methyl)cyclohexylcarbamate (0.085 g, 81%) as a white solid.

1-((4-Aminocyclohexyl)methyl-N-ethyl-3-phenyl-1H-pyrazolo[3,4-d]pyrimidin-6-amine

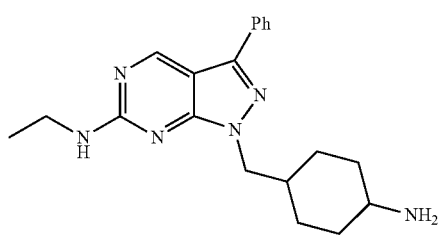 [SMILES: CCNc1ncc2c(-c3ccccc3)nn(CC3CCC(N)CC3)c2n1]

To a solution of tert-butyl-4-((6-(methylthio)-3-phenyl-1H-pyrazolo[3,4-d]pyrimidin-1-yl)methyl)cyclohexylcarbamate (0.045 g, 0.1 mmol) in methylene chloride (3 mL) was added trifluoroacetic acid (0.60 mL). The reaction mixture was stirred at room temperature for 2 h, concentrated and basified by a 7.0 M aqueous solution of ammonia to pH 12. After evaporation, the residue was purified by preparative HPLC to provide 1-((4-aminocyclohexyl)methyl)-N-methyl-3-phenyl-1H-pyrazolo[3,4-d]pyrimidin-6-amine (UNC00000323A) (0.038 g, 82%) as a yellow solid (TFA salt). MS m/z 351.3 [M+H]⁺.

Table 3 describes compounds prepared following procedures described in Example 3 (General Procedure C), using appropriate reagents.

TABLE 3

| Structure | Compound_ID | dr cis:trans | Mer IC₅₀ | Physical Data MS m/z (M + 1) or/and ¹H NMR (400 MHz, CD₃OD) |
|---|---|---|---|---|
| 1 | UNC 00000349A | 1.3:1 | + | MS m/z 351.30 (M + 1). |

TABLE 3-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 2 | 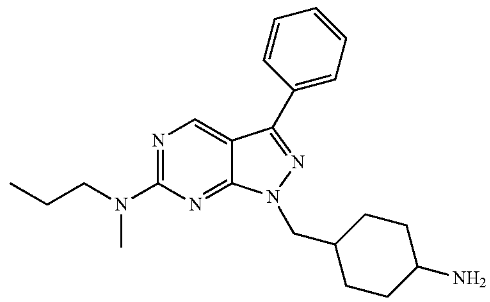 [SMILES: CCCN(C)c1ncc2c(-c3ccccc3)nn(CC3CCC(N)CC3)c2n1] | UNC 00000350A | 1.5:1 | + | MS m/z 379.30 (M + 1). |
| 3 | 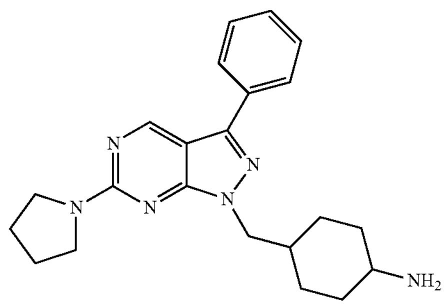 [SMILES: NC1CCC(Cn2nc(-c3ccccc3)c3cnc(N4CCCC4)nc32)CC1] | UNC 00000351A | 1.6:1 | + | MS m/z 377.30 (M + 1). |
| 4 | 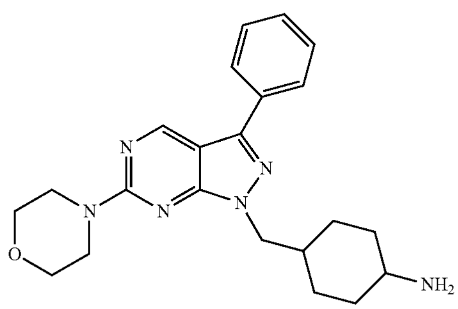 [SMILES: NC1CCC(Cn2nc(-c3ccccc3)c3cnc(N4CCOCC4)nc32)CC1] | UNC 00000352A | 1.7:1 | + | MS m/z 393.30 (M + 1). |
| 5 | 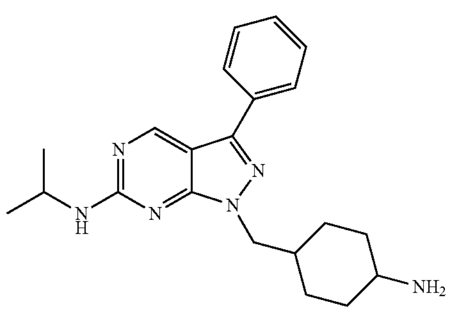 [SMILES: CC(C)Nc1ncc2c(-c3ccccc3)nn(CC3CCC(N)CC3)c2n1] | UNC 00000346A | 1.7:1 | +++ | MS m/z 365.30 (M + 1). |
| 6 | 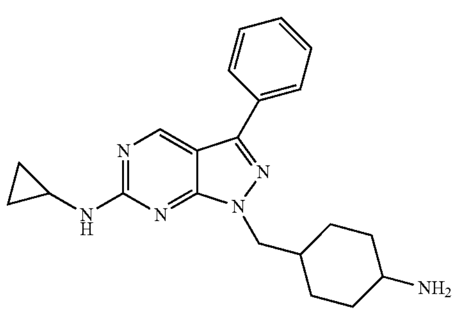 [SMILES: NC1CCC(Cn2nc(-c3ccccc3)c3cnc(NC4CC4)nc32)CC1] | UNC 00000466A | 1.7:1 | ++ | MS m/z 363.30 (M + 1). |

TABLE 3-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 7 | 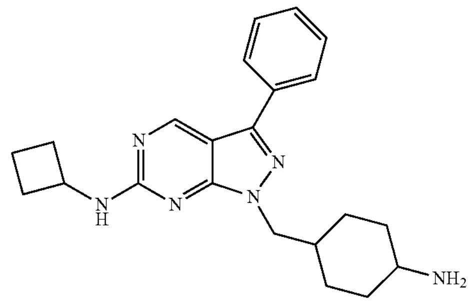 [SMILES: NC1CCC(Cn2nc(-c3ccccc3)c3cnc(NC4CCC4)nc32)CC1] | UNC 00000465A | 1.8:1 | +++ | MS m/z 377.30 (M + 1). |
| 8 | 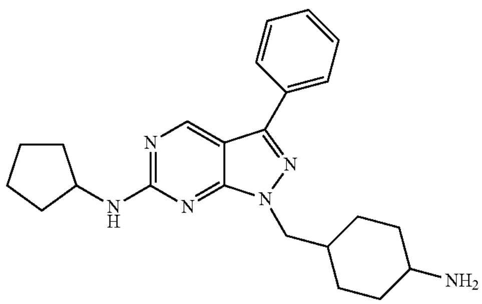 [SMILES: NC1CCC(Cn2nc(-c3ccccc3)c3cnc(NC4CCCC4)nc32)CC1] | UNC 00000347A | 1.7:1 | +++ | MS m/z 391.30 (M + 1). |
| 9 | 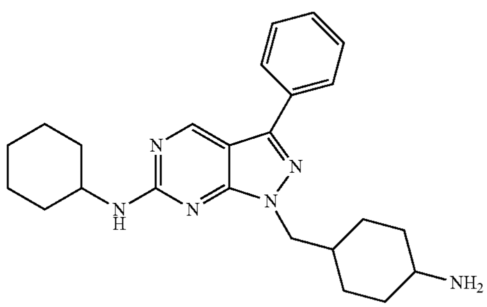 [SMILES: NC1CCC(Cn2nc(-c3ccccc3)c3cnc(NC4CCCCC4)nc32)CC1] | UNC 00000348A | 1.8:1 | ++ | MS m/z 405.30 (M + 1). |
| 10 | 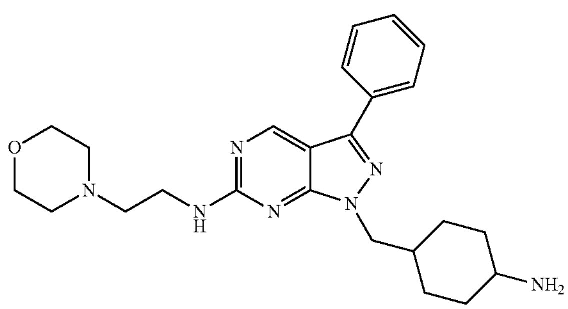 [SMILES: NC1CCC(Cn2nc(-c3ccccc3)c3cnc(NCCN4CCOCC4)nc32)CC1] | UNC 00000345A | 1.6:1 | + | MS m/z 436.30 (M + 1). |
| 11 | 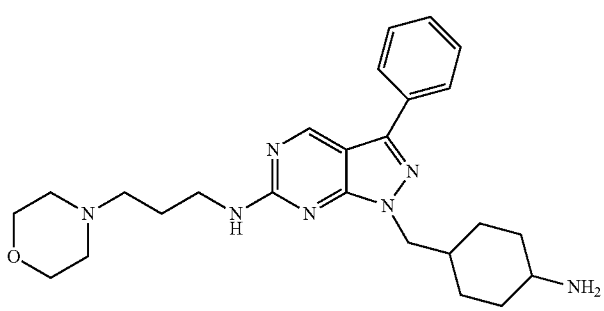 [SMILES: NC1CCC(Cn2nc(-c3ccccc3)c3cnc(NCCCN4CCOCC4)nc32)CC1] | UNC 00000470A | 1.8:1 | + | MS m/z 450.3 (M + 1). |

TABLE 3-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 12 | 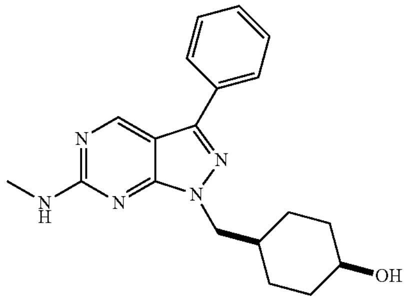 [SMILES: CNc1ncc2c(-c3ccccc3)nn(C[C@H]3CC[C@@H](O)CC3)c2n1] | UNC 00000261A | 1:0 | ++ | $^1$H NMR (400 MHz, CD$_3$OD) δ 9.00 (s, 1H), 7.91 (d, J = 7.7 Hz, 2H), 7.50 (t, J = 7.4 Hz, 2H), 7.46-7.38 (m, 1H), 4.23 (d, J = 7.2 Hz, 2H), 3.86 (s, 1H), 3.02 (s, 3H), 2.15 (bs, 1H), 1.84-1.66 (m, 2H), 1.75-1.45 (m, 6H); MS m/z 338.20 (M + 1). |
| 13 | 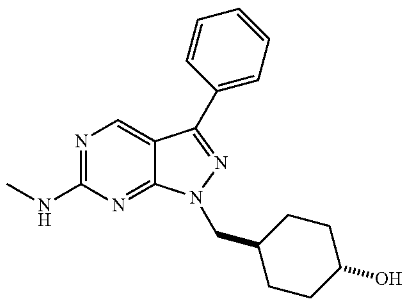 [SMILES: CNc1ncc2c(-c3ccccc3)nn(C[C@H]3CC[C@H](O)CC3)c2n1] | UNC 00000262A | 0:1 | ++ | $^1$H NMR (400 MHz, CD$_3$OD) δ 9.08 (s, 1H), 7.94 (d, J = 7.4 Hz, 2H), 7.56-7.45 (m, 3H), 4.20 (d, J = 7.0 Hz, 2H), 3.49 (bs, 1H), 3.05 (s, 3H), 2.10-1.87 (m, 3H), 1.72 (d, J = 11.1 Hz, 2H), 1.32-1.09 (m, 4H); MS m/z 338.20 (M + 1). |
| 14 | 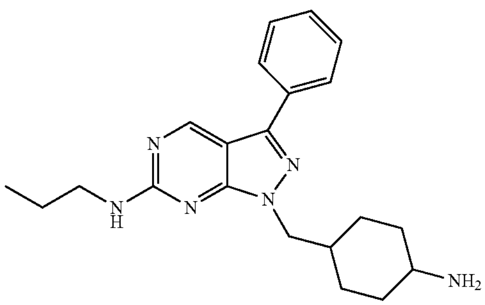 [SMILES: CCCNc1ncc2c(-c3ccccc3)nn(CC3CCC(N)CC3)c2n1] | UNC 00000343A | 1.7:1 | +++ | MS m/z 365.30 (M + 1). |
| 15 | 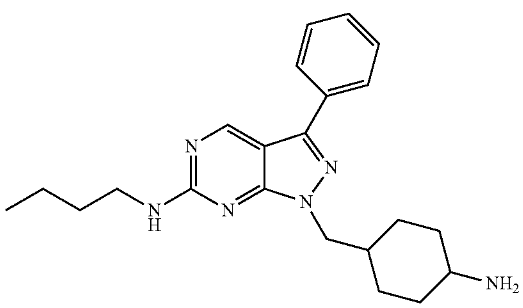 [SMILES: CCCCNc1ncc2c(-c3ccccc3)nn(CC3CCC(N)CC3)c2n1] | UNC 00000344A | 1.7:1 | ++++ | MS m/z 379.30 (M + 1). |
| 16 | 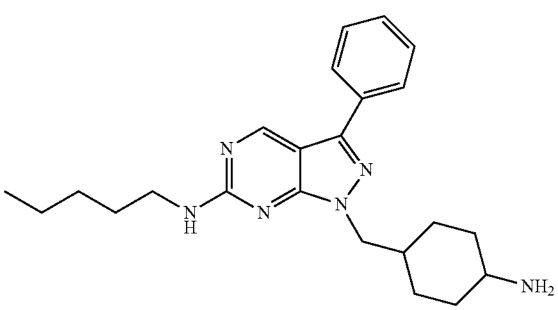 [SMILES: CCCCCNc1ncc2c(-c3ccccc3)nn(CC3CCC(N)CC3)c2n1] | UNC 00000463A | 1.7:1 | +++ | MS m/z 393.30 (M + 1). |

TABLE 3-continued

| | Structure | Compound_ID | dr cis: trans | Mer IC$_{50}$ | Physical Data MS m/z (M + 1) or/and $^1$H NMR (400 MHz, CD$_3$OD) |
|---|---|---|---|---|---|
| 17 | 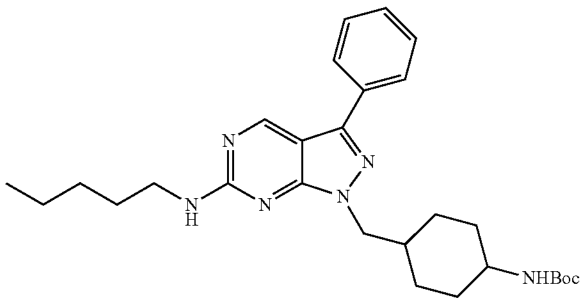 [SMILES: CCCCCNc1ncc2c(-c3ccccc3)nn(CC3CCC(NC(=O)OC(C)(C)C)CC3)c2n1] | UNC 00000461A | 1.7:1 | − | MS m/z 493.40 (M + 1). |
| 18 | 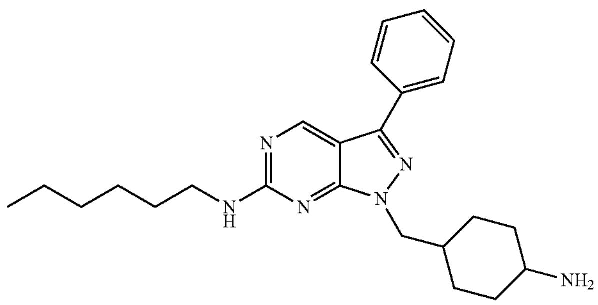 [SMILES: CCCCCCNc1ncc2c(-c3ccccc3)nn(CC3CCC(N)CC3)c2n1] | UNC 00000475A | 1.8:1 | ++++ | MS m/z 407.3 (M + 1). |
| 19 | 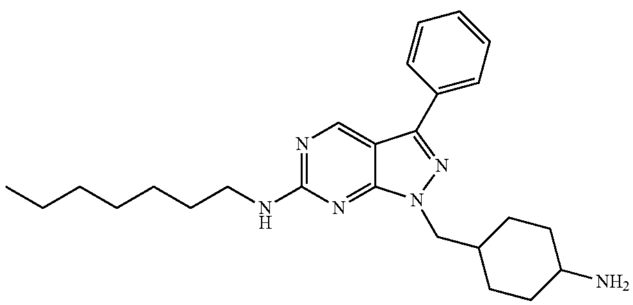 [SMILES: CCCCCCCNc1ncc2c(-c3ccccc3)nn(CC3CCC(N)CC3)c2n1] | UNC 00000464A | 1.8:1 | +++ | MS m/z 421.40 (M + 1). |
| 20 | 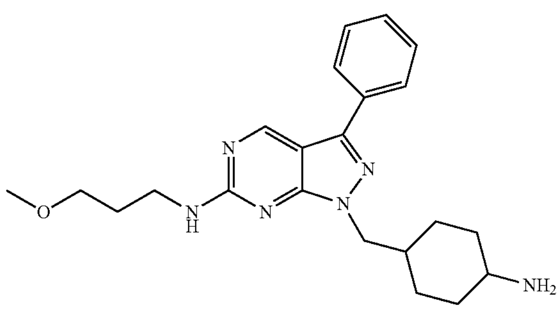 [SMILES: COCCCNc1ncc2c(-c3ccccc3)nn(CC3CCC(N)CC3)c2n1] | UNC 00000467A | 1.9:1 | ++ | MS m/z 395.30 (M + 1). |
| 21 | 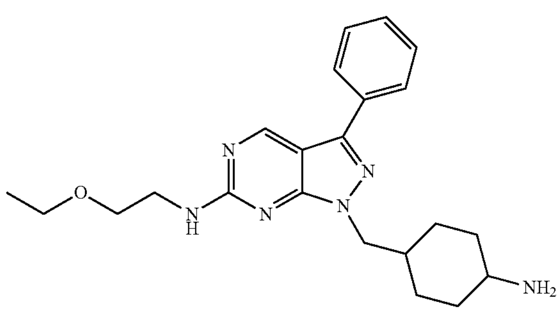 | UNC 00000468A | 1.8:1 | +++ | MS m/z 395.30 (M + 1). |

TABLE 3-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 22 | 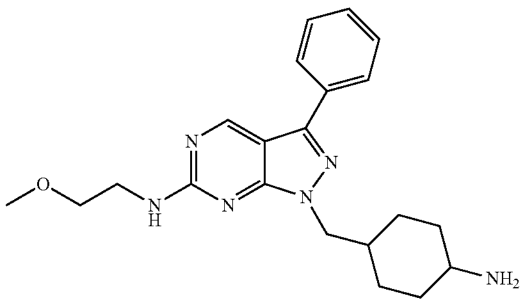 [SMILES: COCCNc1ncc2c(-c3ccccc3)nn(CC3CCC(N)CC3)c2n1] | UNC 00000469A | 1.9:1 | ++ | MS m/z 381.30 (M + 1). |
| 23 | 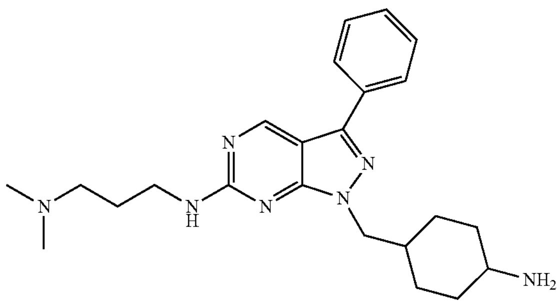 [SMILES: CN(C)CCCNc1ncc2c(-c3ccccc3)nn(CC3CCC(N)CC3)c2n1] | UNC 00000473A | 1.9:1 | − | MS m/z 408.30 (M + 1). |
| 24 | 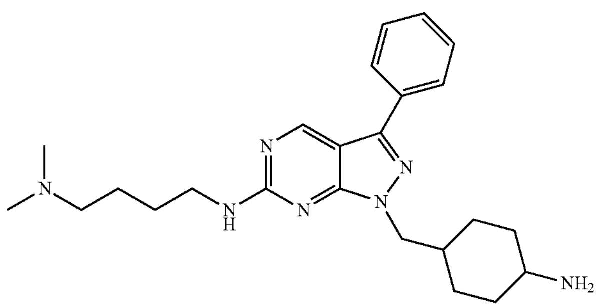 [SMILES: CN(C)CCCCNc1ncc2c(-c3ccccc3)nn(CC3CCC(N)CC3)c2n1] | UNC 00000474A | 1.6:1 | + | MS m/z 422.40 (M + 1). |
| 25 | 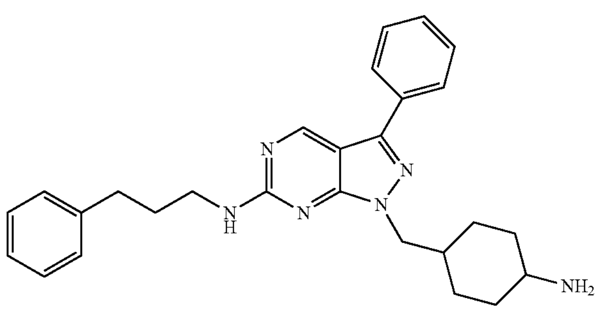 [SMILES: NC1CCC(Cn2nc(-c3ccccc3)c3cnc(NCCCc4ccccc4)nc32)CC1] | UNC 00000573A | 2:1 | +++ | MS m/z 441.30 (M + 1). |
| 26 | 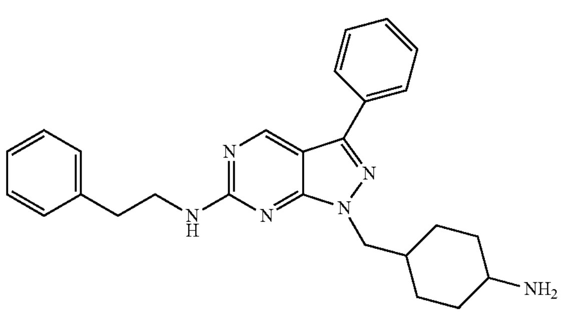 [SMILES: NC1CCC(Cn2nc(-c3ccccc3)c3cnc(NCCc4ccccc4)nc32)CC1] | UNC 00000472A | 1.9:1 | +++ | MS m/z 427.30 (M + 1). |

TABLE 3-continued

| | Structure | Compound_ID | dr cis: trans | Mer IC$_{50}$ | Physical Data MS m/z (M + 1) or/and $^1$H NMR (400 MHz, CD$_3$OD) |
|---|---|---|---|---|---|
| 27 | 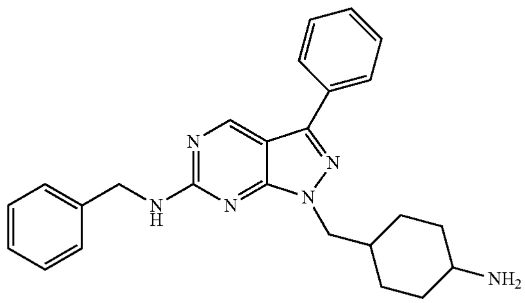 [SMILES: NC1CCC(Cn2nc(-c3ccccc3)c3cnc(NCc4ccccc4)nc32)CC1] | UNC 00000471A | 1.8:1 | ++++ | MS m/z 413.30 (M + 1). |
| 28 | 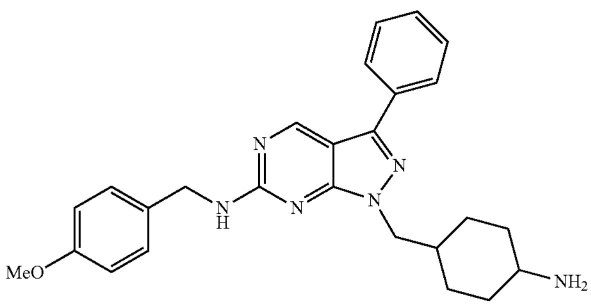 [SMILES: COc1ccc(CNc2ncc3c(-c4ccccc4)nn(CC4CCC(N)CC4)c3n2)cc1] | UNC 00000546A | 2:1 | +++ | MS m/z 443.30 (M + 1). |
| 29 | 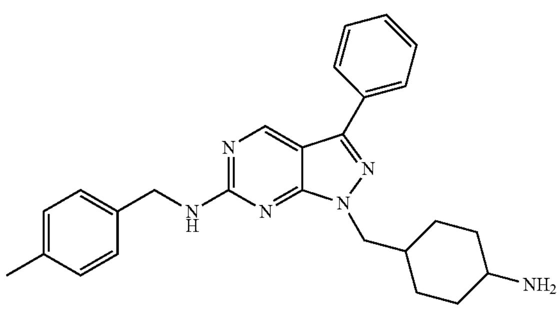 [SMILES: Cc1ccc(CNc2ncc3c(-c4ccccc4)nn(CC4CCC(N)CC4)c3n2)cc1] | UNC 00000551A | 2:1 | ++++ | MS m/z 427.30 (M + 1). |
| 30 | 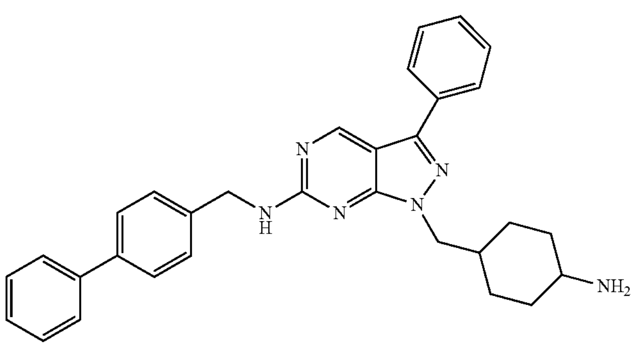 [SMILES: NC1CCC(Cn2nc(-c3ccccc3)c3cnc(NCc4ccc(-c5ccccc5)cc4)nc32)CC1] | UNC 00000554A | 1.7:1 | ++ | MS m/z 489.30 (M + 1). |

TABLE 3-continued

| | Structure | Compound_ID | dr cis: trans | Mer IC$_{50}$ | Physical Data MS m/z (M + 1) or/and $^1$H NMR (400 MHz, CD$_3$OD) |
|---|---|---|---|---|---|
| 31 | 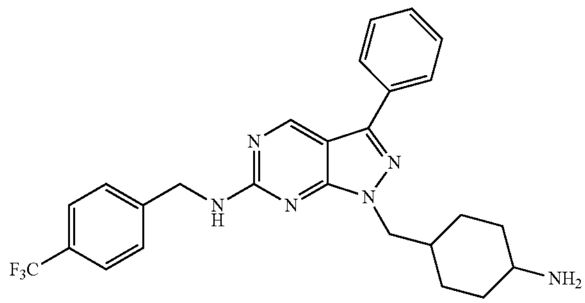 [SMILES: NC1CCC(Cn2nc(-c3ccccc3)c3cnc(NCc4ccc(C(F)(F)F)cc4)nc32)CC1] | UNC 00000550A | 1:1 | ++ | MS m/z 481.30 (M + 1). |
| 32 | 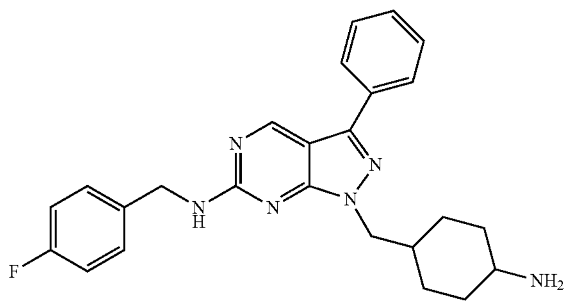 [SMILES: NC1CCC(Cn2nc(-c3ccccc3)c3cnc(NCc4ccc(F)cc4)nc32)CC1] | UNC 00000549A | 1.4:1 | +++ | MS m/z 431.30 (M + 1). |
| 33 | 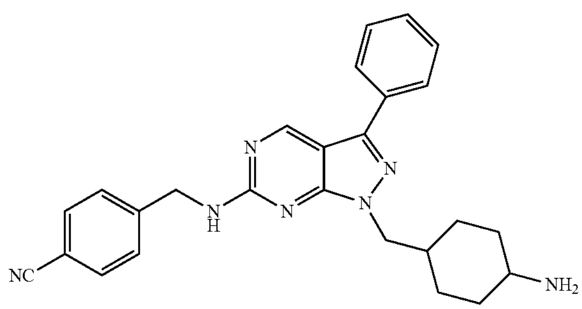 [SMILES: N#Cc1ccc(CNc2ncc3c(-c4ccccc4)nn(CC4CCC(N)CC4)c3n2)cc1] | UNC 00000555A | 2:1 | +++ | MS m/z 438.30 (M + 1). |
| 34 | 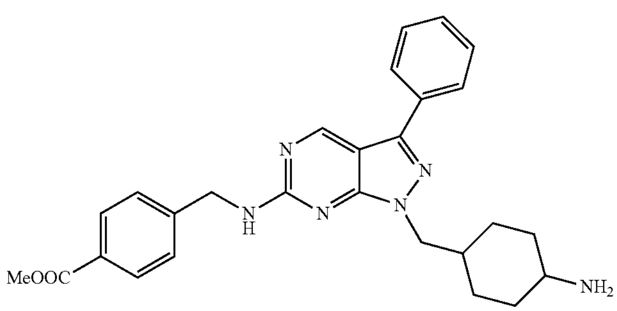 [SMILES: COC(=O)c1ccc(CNc2ncc3c(-c4ccccc4)nn(CC4CCC(N)CC4)c3n2)cc1] | UNC 00000574A | 2:1 | +++ | MS m/z 471.30 (M + 1). |
| 35 | 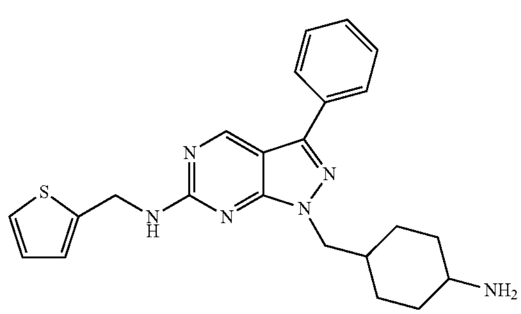 [SMILES: NC1CCC(Cn2nc(-c3ccccc3)c3cnc(NCc4ccco4)nc32)CC1] | UNC 00000552A | 1:1 | ++++ | MS m/z 419.20 (M + 1). |

TABLE 3-continued

| Structure | Compound_ID | dr cis:trans | Mer IC$_{50}$ | Physical Data MS m/z (M + 1) or/and $^1$H NMR (400 MHz, CD$_3$OD) |
|---|---|---|---|---|
| 36 | UNC 00000553A | 1.5:1 | +++ | MS m/z 403.25 (M + 1). |
| 37 | UNC 00000572A | 1.5:1 | +++ | MS m/z 414.30 (M + 1). |
| 38 | UNC 00000265A | 1:0 | ++ | $^1$H NMR (400 MHz, CD$_3$OD) δ 8.97 (s, 1H), 5.80 (s, 1H), 5.48 (s, 1H), 4.19 (d, J = 7.1 Hz, 2H), 3.86 (s, 1H), 3.04 (s, 3H), 2.20 (s, 3H), 2.10 (bs, 1H), 1.80-1.70 (m, 2H), 1.62-1.33 (m, 6H); MS m/z 302.20 (M + 1). |
| 39 | UNC 00000266A | 0:1 | ++ | $^1$H NMR (400 MHz, CD$_3$OD) δ 8.94 (s, 1H), 5.79 (s, 1H), 5.46 (s, 1H), 4.12(d, J = 7.0 Hz, 2H), 3.55-3.45 (m, 1H), 3.02 (s, 3H), 2.20 (s, 3H), 1.94 (d, J = 11.5 Hz, 3H), 1.67 (d, J = 12.0 Hz, 2H), 1.29-1.05 (m, 4H); MS m/z 302.20 (M + 1). |
| 40 | UNC 00000297A | 1:0 | + | $^1$H NMR (400 MHz, CD$_3$OD) δ 8.92 (s, 1H), 4.13 (d, J = 7.2 Hz, 2H), 3.86 (bs, 1H), 3.29-3.21 (m, 1H), 3.04 (d, J = 1.1 Hz, 3H), 2.12-2.01 (m, 1H), 1.78-1.66 (m, 2H), 1.62-1.44 (m, 5H), 1.44-1.32 (m, 1H), 1.39 (d, J = 7.2 Hz, 6H); MS m/z 304.30 (M + 1). |

TABLE 3-continued

| | Structure | Compound_ID | dr cis:trans | Mer IC$_{50}$ | Physical Data MS m/z (M + 1) or/and $^1$H NMR (400 MHz, CD$_3$OD) |
|---|---|---|---|---|---|
| 41 | 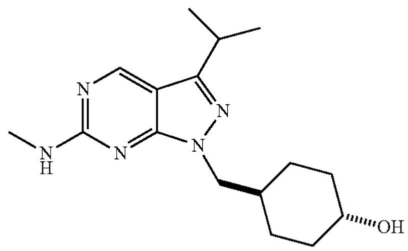 [SMILES: CNc1ncc2c(C(C)C)nn(C[C@H]3CC[C@H](O)CC3)c2n1] | UNC 00000298A | 0:1 | + | $^1$H NMR (400 MHz, CD$_3$OD) δ 8.90 (s, 1H), 4.08 (d, J = 6.8 Hz, 2H), 3.54-3.40 (m, 1H), 3.29-3.19 (m, 1H), 3.02 (s, 3H), 2.00-1.83 (m, 3H), 1.65 (d, J = 12.8 Hz, 2H), 1.38 (d, J = 8.0 Hz, 6H) 1.27-1.04 (m, 4H), MS m/z 304.20 (M + 1). |
| 42 | 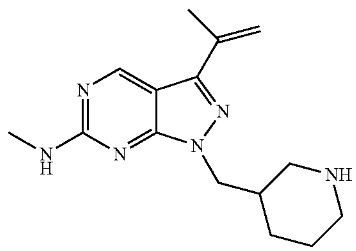 [SMILES: C=C(C)c1nn(CC2CCCNC2)c2nc(NC)ncc12] | UNC 00000267A | N/A | + | $^1$H NMR (400 MHz, CD$_3$OD) δ 8.9S (d, J = 1.0 Hz, 1H), 5.81 (s, 1H), 5,48 (s, 1H), 4.33-4.22 (m, 2H), 3.03 (d, J = 1.1 Hz, 3H), 2.95-2.83 (m, 3H), 2.51-2.38 (m, 1H), 2.20 (s, 3H), 2.05-1.84 (m, 3H), 1.80-1.65 (m, 1H), 1.46-1.33 (m, 1H); MS m/z 287.20 (M + 1). |
| 43 | 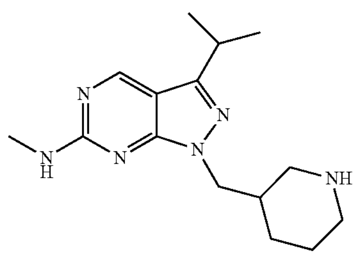 [SMILES: CNc1ncc2c(C(C)C)nn(CC3CCCNC3)c2n1] | UNC 00000299A | N/A | + | $^1$H NMR (400 MHz, CD$_3$OD) δ 8.97 (s, 1H), 4.31-4.16 (m, 2H), 3.35-3.25 (m, 3H), 3.05 (s, 3H), 2.96-2.81 (m, 2H), 2.44 (bs, 1H), 1.93-1.73 (m, 2H), 1.72-1.57 (m, 1H), 1.45-1.32 (m, 1H), 1.39 (d, J = 6.8 Hz, 6H); MS m/z 289.20 (M + 1). |
| 44 | 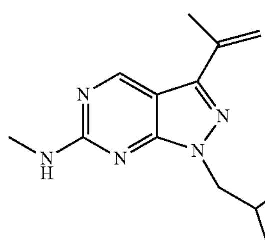 | UNC 00000268A | N/A | + | $^1$H NMR (400 MHz, CD$_3$OD) δ 9.00 (s, 1H), 5.84 (s, 1H), 5.49 (s, 1H), 4.74 (dd, J = 15.0, 3,7 Hz, 1H), 4.50 (dd, J = 15.0, 8.5 Hz, 1H), 4.13-4.00 (m, 1H), 3.45-3.31 (m, 2H), 3.35-3.25 (m, 1H), 2.23 (s, 3H), 2.14-1.99 (m, 2H), 1.92-1.80 (m, 1H); MS m/z 273.20 (M + 1). |
| 45 | 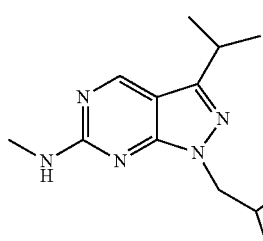 | UNC 00000300A | N/A | + | $^1$H NMR (400 MHz, CD$_3$OD) δ 9.00 (s, 1H), 4.67 (dd, J = 15.0, 3.8 Hz, 1H), 4.50 (dd, J = 15.0, 8.4 Hz, 1H), 4.16-4.02 (m, 1H), 3.48-3.31 (m, 3H), 3.05 (d, J = 1.1 Hz, 3H), 2.37-2.23 (m, 1H), 2.16-1.98 (m, 2H), 1.93-1.80 (m, 1H), 1.41 (dd, J = 7.0, 1.1 Hz, 6H); MS m/z 275.20 (M + 1). |
| 46 | 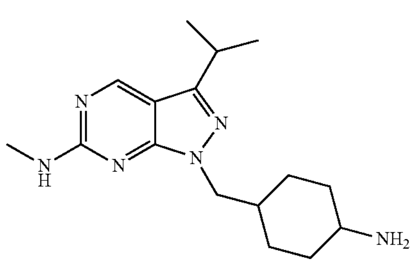 [SMILES: CNc1ncc2c(C(C)C)nn(CC3CCC(N)CC3)c2n1] | UNC 00000269A | 1:1 | + | MS m/z 303.30 (M + 1). |

TABLE 3-continued

| | Structure | Compound_ID | dr cis: trans | Mer IC$_{50}$ | Physical Data MS m/z (M + 1) or/and $^1$H NMR (400 MHz, CD$_3$OD) |
|---|---|---|---|---|---|
| 47 | 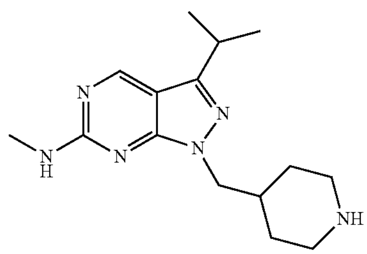 [SMILES: CNc1ncc2c(C(C)C)nn(CC3CCNCC3)c2n1] | UNC 00000270A | N/A | + | $^1$H NMR (400 MHz, CD$_3$OD) δ 9.01 (s, 1H), 4.23 (d, J = 6.8 Hz, 1H), 4.14 (d, J = 6.9 Hz, 1H), 3.31-3.29 (m, 1H), 3.06 (s, 3H), 2.34-2.25 (m, 1H), 2.09-1.96 (m, 2H), 1.88-1.73 (m, 2H), 1.65-1.48 (m, 2H), 1.39 (d, J = 7.0 Hz, 6H), 1.45-1.16 (m, 2H); MS m/z 289.20 (M + 1). |
| 48 | 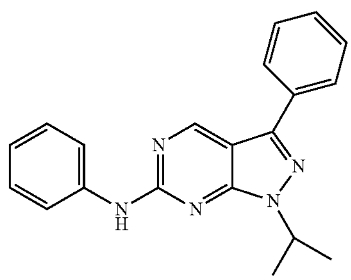 [SMILES: CC(C)n1nc(-c2ccccc2)c2cnc(Nc3ccccc3)nc21] | UNC 999A | N/A | + | $^1$H NMR (400 MHz, CDCl$_3$) δ 9.07 (s, 1H), 8.00-7.90 (m, 2H), 7.77 (d, J = 7.8 Hz, 2H), 7.51 (t, 2H), 7.46-7.34 (m, 4H), 7.08 (t, J = 7.4 Hz, 1H), 5.20-5.03 (m, 1H), 1.65 (d, J = 6.7 Hz, 6H); $^{13}$C NMR (100 MHz, CDCl$_3$) δ 157.6, 154.4, 153.7, 143.9, 139.7, 132.9, 129.1, 129.1, 128.8, 127.1, 122.7, 119.1, 108.0, 49.1, 22.0; MS m/z 330.2 (M + 1). |
| 49 | 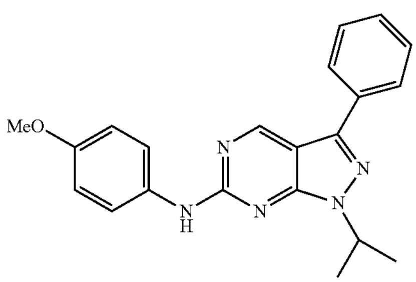 [SMILES: COc1ccc(Nc2ncc3c(-c4ccccc4)nn(C(C)C)c3n2)cc1] | UNC 1000A | N/A | + | $^1$H NMR (400 MHz, CDCl$_3$) δ 9.04 (s, 1H), 7.97-7.91 (m, 2H), 7.68-7.60 (m, 2H), 7.53-7.47 (m, 2H), 7.46-7.39 (m, 2H), 6.99-6.91 (m, 2H), 5.14-5.01 (m, 1H), 3.84 (s, 3H), 1.63 (d, J = 6.7 Hz, 6H); $^{13}$C NMR (100 MHz, CDCl$_3$) δ 158.0, 155.6, 154.6, 153.6, 143.9, 133.0, 132.9, 129.1, 128.8, 127.1, 121.2, 114.3, 107.7, 55.7, 48.9, 22.0; MS m/z 360.2 (M + 1). |
| 50 | 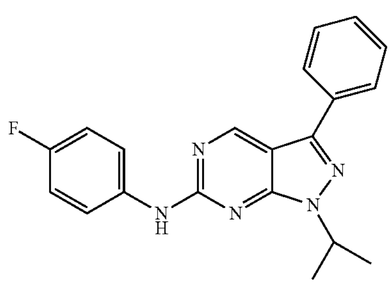 [SMILES: CC(C)n1nc(-c2ccccc2)c2cnc(Nc3ccc(F)cc3)nc21] | UNC 1001A | N/A | − | $^1$H NMR (400 MHz, CDCl$_3$) δ 9.06 (s, 1H), 7.97-7.91 (m, 2H), 7.74-7.66 (m, 2H), 7.55-7.46 (m, 3H), 7.45-7.39 (m, 1H), 7.13-7.04 (m, 2H), 5.14-5.04 (m, 1H), 1.64 (d, J = 6.7 Hz, 6H); $^{13}$C NMR (100 MHz, CDCl$_3$) δ 159.8, 157.7, 157.4, 154.4, 153.7, 144.0, 135.8, 135.7, 132.9, 129.1, 128.9, 127.1, 120.9, 120.8, 115.8, 115.6, 108.0, 49.1, 22.0; MS m/z 348.2 (M + 1). |

TABLE 3-continued

| | Structure | Compound_ID | dr cis: trans | Mer IC$_{50}$ | Physical Data MS m/z (M + 1) or/and $^1$H NMR (400 MHz, CD$_3$OD) |
|---|---|---|---|---|---|
| 51 | 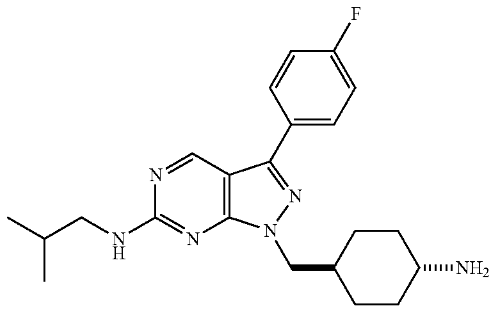 | UNC 1353A | N/A | ND | $^1$H NMR (400 MHz, CD$_3$OD) δ 9.07 (s, 1H), 8.01-7.93 (m, 2H), 7.31-7.22 (m, 2H), 4.22 (d, J = 6.8 Hz, 2H), 3.34 (d, J = 6.9 Hz, 2H), 3.12-3.02 (m, 1H), 2.13-1.94 (m, 4H), 1.84 (d, J = 12.3 Hz, 2H), 1.47-1.20 (m, 4H), 1.01 (d, J = 6.7 Hz, 6H): MS m/z 397.3 (M + 1). |
| 52 | 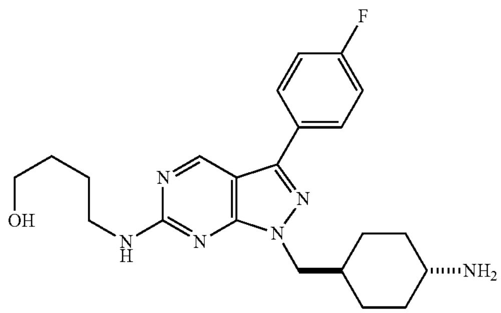 | UNC 1354A | N/A | ND | $^1$H NMR (400 MHz, CD$_3$OD) δ 9.13 (s, 1H), 8.03-7.95 (m, 2H), 7.31-7.22 (m, 2H), 4.23 (d, J = 6.9 Hz, 2H), 3.63 (t, J = 6.4 Hz, 2H), 3.56 (t, 7.0 Hz, 2H), 3.12-3.02 (m, 1H), 2.15-2.01 (m, 3H), 1.89-1.72 (m, 4H), 1.71-1.60 (m, 2H), 1.47-1.20 (m, 4H); MS m/z 413.50 (M + 1). |

Example 4

The R$^2$ Position

1-Cyclohexyl-3-phenyl-N-propyl-1H-pyrazolo[3,4-d]pyrimidin-6-amine

General Procedure D:

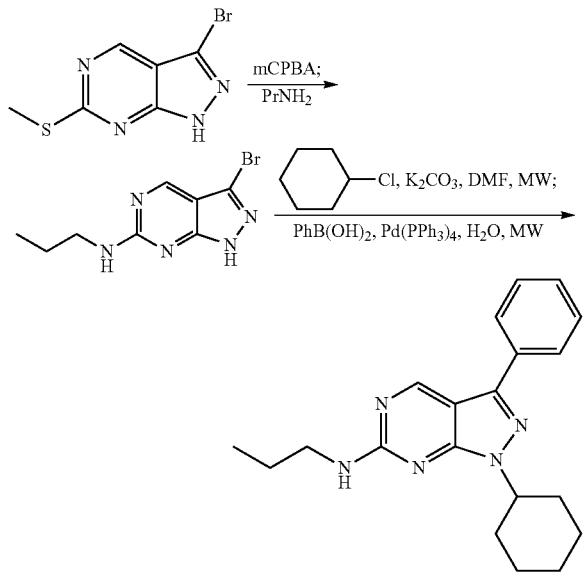

3-Bromo-N-propyl-1H-pyrazolo[3,4-d]pyrimidin-6-amine

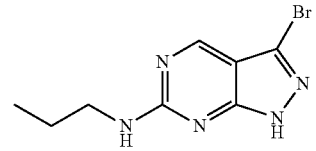

To a mixture of 3-bromo-6-(methylthio)-1H-pyrazolo[3,4-d]pyrimidine (0.49 g, 2.0 mmol) in THF (5 mL) was added meta-chloroperoxybenzoic acid (0.52 g, 99%, 3 mmol) at room temperature. The white mixture was stirred for 2 h and n-propylamine (0.82 mL, 10 mmol) was added at 0° C. The resulting solution was heated at 40° C. for 12 h. After removal of the solvent, MeOH was added and the mixture was filtered. The white solid was washed with MeOH (3×) and dried to provide 3-bromo-N-propyl-1H-pyrazolo[3,4-d]pyrimidin-6-amine (0.45 g, 88%) as a white solid. $^1$H NMR (400 MHz, DMSO-d6) δ 13.19 (bs, 1H), 8.63 (s, 1H), 7.69 (bs, 1H), 3.29-3.17 (m, 2H), 1.61-1.49 (m, 2H), 0.88 (t, J=7.4 Hz, 3H); $^{13}$C NMR (100 MHz, DMSO-d6) δ 161.61, 156.98, 152.71, 120.06, 106.66, 42.68, 21.72, 11.47; MS m/z 256.1 [M+1].

1-Cyclohexyl-3-phenyl-N-propyl-1H-pyrazolo[3,4-d]pyrimidin-6-amine

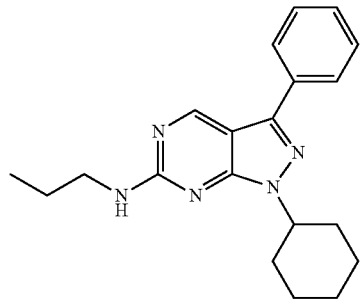 [SMILES: CCCNc1ncc2c(-c3ccccc3)nn(C3CCCCC3)c2n1]

A 10 mL microwave tube was charged with 3-bromo-N-propyl-1H-pyrazolo[3,4-d]pyrimidin-6-amine (0.052 g, 0.2 mmol), $K_2CO_3$ (0.14 g, 1.0 mmol), DMF (2 mL), and cyclohexyl chloride (0.072 g, 0.6 mmol). The resulting mixture was heated at 200° C. for 30 minutes under microwave irradiation. After the reaction was cooled to room temperature, phenylboronic acid (0.37 g, 0.3 mmol), $Pd(PPh_3)_4$ (0.023 g, 0.02 mmol), and $H_2O$ (1 mL) were added sequentially. The mixture was stirred at room temperature for 3 min and then heated at 150° C. for 15 min. After cooled to room temperature, the mixture was partitioned in $H_2O$ and $Et_2O$. The aqueous phase was extracted with ether (3×). The combined organic phase were dried ($Na_2SO_4$) and concentrated. The residue was purified by Isco to provide the 1-cyclohexyl-3-phenyl-N-propyl-1H-pyrazolo[3,4-d]pyrimidin-6-amine (UNC702A) (0.045 g, 67%) as a white solid. $^1$H NMR (400 MHz, CDCl$_3$) δ 8.93 (s, 1H), 7.90 (d, J=8.0 Hz, 2H), 7.48 (t, J=6.0 Hz, 2H), 7.38 (t, J=6.0 Hz, 1H), 5.42 (s, 1H), 4.60 (tt, J=11.6, 4.1 Hz, 1H), 3.48 (dt, J=13.1, 6.8 Hz, 2H), 2.18-2.08 (m, 2H), 2.04-2.00 (m, 2H), 1.95-1.92 (m, 2H), 1.77-1.74 (m, 1H), 1.74-1.65 (m, 2H), 1.58-1.42 (m, 2H), 1.40-1.28 (m, 1H), 1.03 (t, J=7.4 Hz, 3H); $^{13}$C NMR (100 MHz, CDCl$_3$) δ 160.73, 155.38, 153.50, 143.71, 133.27, 129.06, 128.60, 127.09, 106.91, 56.10, 43.68, 32.16, 25.91, 25.61, 22.98, 11.77; MS m/z 336.2 [M+1].

Table 4 describes compounds prepared following procedures described in Example 4 (General Procedure D), using appropriate reagents.

TABLE 4

| | Structure | Compound_ID | Mer IC$_{50}$ | Physical Data MS m/z (M + 1) or/and $^1$H NMR (400 MHz) |
|---|---|---|---|---|
| 1 | COOMe-substituted structure | UNC703A | ++ | $^1$H NMR (400 MHz, CDCl$_3$) δ 8.95 (s, 1H), 8.13 (d, J = 8.3 Hz, 2H), 7.98 (d, J = 8.3 Hz, 2H), 5.48 (bs, 1H), 4.61 (tt, J = 11.5, 4.1 Hz, 1H), 3.94 (s, 3H), 3.48 (dt, J = 12.6, 6.7 Hz, 2H), 2.16-2.06 (m, 2H), 2.06-1.98 (m, 2H), 1.97-1.90 (m, 2H), 1.80- 1.73 (m, 1H), 1.74-1.64 (m, 2H), 1.57-1.42 (m, 2H), 1.42-1.28 (m, 1H), 1.02 (t, J = 7.4 Hz, 3H); $^{13}$C NMR (100 MHz, CDCl$_3$) δ 166.95, 160.60, 155.47, 153.22, 142.40, 137.51, 130.30, 129.83, 126.69, 106.82, 56.17, 52.29, 43.61, 32.11, 25.81, 25.52, 22.88, 11.69; MS m/z 394.0 (M + 1). |
| 2 | COOH-substituted structure | UNC705A | ++++ | $^1$H NMR (400 MHz, CD$_3$OD + CD$_2$Cl$_2$ + several drops of NH$_3$ CH$_3$OH solution) δ 8.97 (s, 1H), 8.06 (d, J = 8.4 Hz, 2H),7.92 (d, J = 8.4 Hz, 2H), 4.66-4.58 (m, 1H), 3.44 (t, J = 7.1 Hz, 2H), 2.20-2.06 (m, 2H), 2.03-1.88 (m, 4H), 1.80-1.76 (m, 1H), 1.70 (tq, J = 7.1, 7.4 Hz, 2H), 1.59-1.45 (m, 2H), 1.42-1.33 (m, 1H), 1.01 (t, J = 7.4 Hz, 3H); $^{13}$C NMR (100 MHz, CD$_3$OD + CD$_2$Cl$_2$ + several drops of NH$_3$ CH$_3$OH solution) δ 174.84, 161.91, 156.45, 154.76, 144.75, 139.20, 135.55, 130.77, 127.21, 107.31, 57.22, 44.23, 32.94, 26.74, 26.49, 23.54, 11.85; MS m/z 380.2 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 3 | 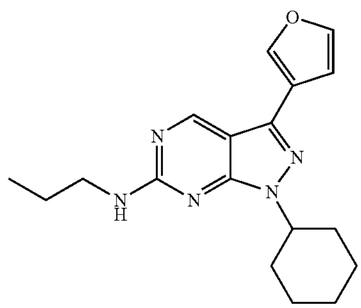 [SMILES: CCCNc1ncc2c(-c3ccoc3)nn(C3CCCCC3)c2n1] | UNC704A | +++ | $^1$H NMR (400 MHz, CDCl$_3$) δ 8.75 (s, 1H), 7.93 (s, 1H), 7.51 (t, J = 1.6 Hz, 1H), 6.93-6.87 (d, J = 1.6 Hz, 1H), 5.38 (bs, 1H), 4.54 (tt, J = 11.7, 4.0 Hz, 1H), 3.46 (dt, J = 13.1, 6.8 Hz, 2H), 2.15-2.03 (m, 2H), 2.01-1.88 (m, 4H), 1.78-1.72 (m, 1H), 1.73-1.63 (m, 2H), 1.54-1.41 (m, 2H), 1.38-1.29 (m, 1H), 1.02 (t, J = 7.4 Hz, 3H); $^{13}$C NMR (100 MHz, CDCl$_3$) δ 160.84, 154.94, 152.67, 143.68, 140.02, 136.96, 119.19, 109.06, 106.90, 56.13, 43.63, 32.02, 25.84, 25.52, 22.91, 11.69; MS m/z 326.2 (M + 1). |
| 4 | 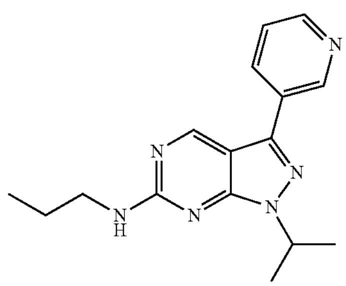 [SMILES: CCCNc1ncc2c(-c3cccnc3)nn(C(C)C)c2n1] | UNC706A | ++ | $^1$H NMR (400 MHz, CDCl$_3$) δ 9.15 (s, 1H), 8.91 (s, 1H), 8.63 (d, J = 4.9, 1H), 8.22 (d, J = 7.7 Hz, 1H), 7.42 (dd, J = 7.7, 4.9 Hz, 1H), 5.54 (bs, 1H), 5.10-4.98 (m, 1H), 3.47 (dt, J = 13.2, 6.7 Hz, 2H), 1.77-1.63 (m, 2H), 1.58 (d, J = 6.7 Hz, 6H), 1.02 (t, J = 7.4 Hz, 3H); $^{13}$C NMR (100 MHz, CDCl$_3$) δ 160.41, 155.33, 152.71, 149.49, 147.99, 140.79, 134.18, 129.29, 123.99, 106.62, 48.73, 43.60, 22.82, 21.87, 11.68; MS m/z 297.2 (M + 1). |
| 5 | 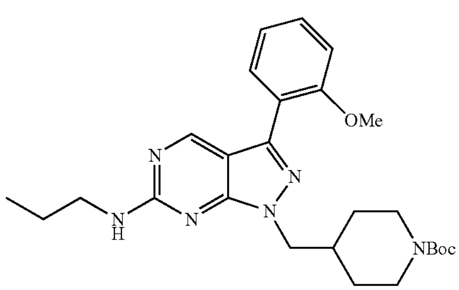 [SMILES: CCCNc1ncc2c(-c3ccccc3OC)nn(CC3CCN(C(=O)OC(C)(C)C)CC3)c2n1] | UNC707A | + | $^1$H NMR (400 MHz, CDCl$_3$) δ 8.80 (s, 1H), 7.75 (dd, J = 7.6, 1.6 Hz, 1H), 7.41-7.34 (m, 1H), 7.08-6.99 (m, 2H), 5.55 (bs, 1H), 4.20 (d, J = 7.1 Hz, 2H), 4.14-3.99 (m, 2H), 3.87 (s, 3H), 3.48-3.40 (m, 2H), 2.68 (t, J = 11.9 Hz, 2H), 2.28-2.16 (m, 1H), 1.72-1.57 (m, 4H), 1.43 (s, 9H), 1.34-1.22 (m, 2H), 1.00 (t, J = 7.4 Hz, 3H); $^{13}$C NMR (100 MHz, CDCl$_3$) δ 159.15, 156.76, 156.10, 154.93, 153.75, 143.05, 130.61, 130.46, 121.80, 121.30, 111.39 107.39, 79.50, 55.56, 51.49, 43.59, 36.74, 29.87, 28.58, 22.68, 11.68; MS m/z 481.3 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 6 | (structure with OMe-phenyl, pyrazolopyrimidine, propylamine, ethyl-pyrrolidine) | UNC708 A | + | $^1$H NMR (400 MHz, CD$_3$OD) δ 8.85 (s, 1H), 7.79 (d, J = 8.8 Hz, 2H), 6.99 (d, J = 8.8 Hz, 2H), 4.40 (t, J = 6.7 Hz, 2H), 3.82 (s, 3H), 3.44-3.35 (m, 2H), 3.00 (t, J = 6.8 Hz, 2H), 2.66-2.60 (m, 3H), 1.79-1.73 (m, 4H), 1.72-1.61 (m, 2H), 0.98 (t, J = 7.4 Hz, 3H); $^{13}$C NMR (100 MHz, CD$_3$OD) δ 162.20, 161.72, 157.35, 154.84, 145.77, 129.22, 126.20, 115.32, 106.86, 55.80, 55.79, 55.02, 45.76, 44.25, 24.19, 23.58, 11.88; MS m/z 381.3 (M + 1). |
| 7 | (structure with pyrimidine, pyrazolopyrimidine, propylamine, pentyl-OH) | UNC709 A | + | $^1$H NMR (400 MHz, CDCl$_3$) δ 9.22 (d, J = 13.2 Hz, 3H), 8.89 (s, 1H), 5.74 (s, 1H), 4.33 (t, J = 7.0 Hz, 2H), 3.63 (t, J = 6.5 Hz, 2H), 3.44 (dd, J = 13.0, 6.7 Hz, 2H), 2.44 (bs, 1H), 2.06-1.88 (m, 2H), 1.73-1.56 (m, 4H), 1.49-1.35 (m, 2H), 0.99 (t, J = 7.4 Hz, 3H); $^{13}$C NMR (100 MHz, CDCl$_3$) δ 160.95, 158.14, 156.19, 154.52, 152.81, 137.82, 127.32, 106.00, 62.57, 46.48, 43.52, 32.27, 29.17, 23.01, 22.72, 11.63; MS m/z 342.2 (M + 1). |
| 8 | (structure with CN-phenyl, pyrazolopyrimidine, propylamine, benzyl) | UNC710 A | + | $^1$H NMR (400 MHz, CDCl$_3$ + CD$_2$Cl$_2$) δ 8.92 (s, 1H), 8.00 (d, J = 8.3 Hz, 2H), 7.73 (d, J = 8.2 Hz, 2H), 7.38 (d, J = 6.8 Hz, 2H), 7.34-7.22 (m, 3H), 5.492 (bs, 1H), 5.49 (s, 2H), 3.47 (dt, J = 13.2, 6.6 Hz, 2H), 1.76-1.59 (m, 2H), 1.00 (t, J = 7.4 Hz, 3H); $^{13}$C NMR (100 MHz, CDCl$_3$ + CD$_2$Cl$_2$) δ 160.97, 156.38, 153.04, 142.32, 137.13, 136.66, 132.72, 128.65, 128.23, 127.89, 127.21, 118.78, 111.93, 106.16, 50.33, 43.50, 22.68, 11.51; MS m/z 369.2 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 9 | 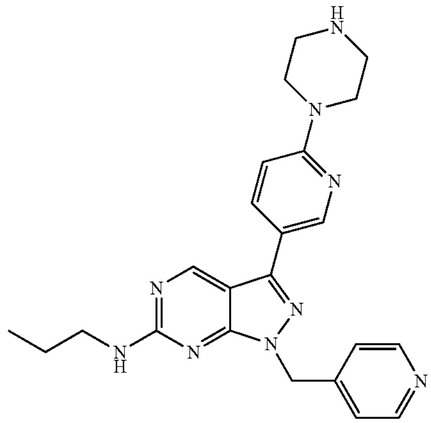 [SMILES: CCCNc1ncc2c(-c3ccc(N4CCNCC4)nc3)nn(Cc3ccncc3)c2n1] | UNC711A | ++ | $^1$H NMR (400 MHz, CD$_3$OD) δ 9.22 (s, 1H), 8.85 (d, J = 5.1 Hz, 2H), 8.75 (d, J = 2.2 Hz, 1H), 8.25 (dd, J = 9.1, 2.3 Hz, 1H), 8.00 (d, J = 6.2 Hz, 2H), 7.13 (d, J = 9.1 Hz, 1H), 5.88 (s, 2H), 4.03-3.91 (m, 4H), 3.44 (t, J = 7.1 Hz, 2H), 3.37 (m, 4H), 3.35 (s, 2H), 1.72-1.60 (m, 2H), 0.98 (q, J = 7.3 Hz, 3H); $^{13}$C NMR (100 MHz, CD$_3$OD) δ 159.29, 157.98, 146.44, 143.87, 138.08, 126.77, 120.24, 119.34, 117.41, 114.58, 111.75, 109.34, 106.72, 49.85, 44.34, 44.19, 43.35, 23.10, 11.69; MS m/z 430.3 (M + 1). |
| 10 | 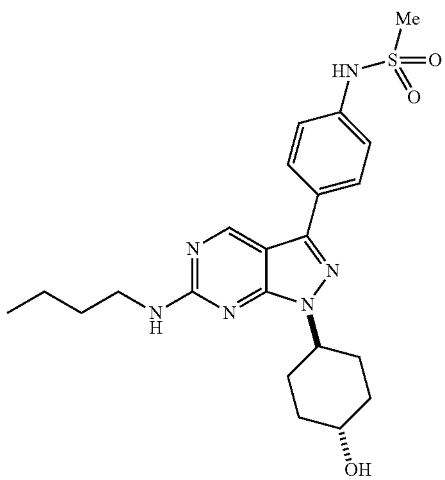 | UNC978A | ++++ | $^1$H NMR (400 MHz, CDCl$_3$) δ 8.76 (s, 1H), 7.76-7.72 (m, 2H), 7.28-7.24 (m, 2H), 4.56-4.48 (m, 1H), 3.71-3.61 (m, 1H), 3.42-3.39 (m, 1H), 3.29-3.27 (m, 2H), 2.92 (s, 3H), 2.14-2.02 (m, 4H), 1.97-1.90 (m, 2H), 1.61-1.53 (m, 2H), 1.47-1.32 (m, 6H), 0.90 (t, J = 7.36 Hz, 3H); MS m/z 459.30 (M + 1). |
| 11 | 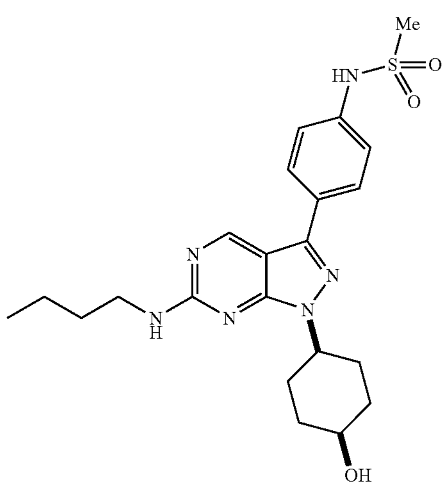 | UNC970A | +++ | $^1$H NMR (400 MHz, CDCl$_3$) δ 9.27 (s, 1H), 8.83 (s, 1H), 7.94 (s, 1H), 7.79 (d, J = 5.93 Hz, 2H), 7.38-7.35 (m, 2H), 4.67-4.60 (m, 1H), 3.53 (s, 2H), 3.06 (s, 3H), 2.56-2.48 (m, 1H), 2.36-2.32 (m, 1H), 2.16-1.97 (m, 4H), 1.86-1.68 (m, 4H), 1.49-1.40 (m, 3H), 0.97 (td, J = 3.02, 7.30 Hz, 3H); MS m/z 459.20 (M + 1). |

TABLE 4-continued

| | | | Physical Data |
|---|---|---|---|
| Structure | Compound_ID | Mer IC$_{50}$ | MS m/z (M + 1) or/and $^1$H NMR (400 MHz) |
| 12 | UNC971A | ++++ | $^1$H NMR (400 MHz, CDCl$_3$) δ 8.95 (s, 1H), 8.04 (d, J = 8.61 Hz, 2H), 7.97 (d, J = 8.59 Hz, 2H), 5.36 (brs, 1H), 4.67-4.64 (m, 1H), 4.34 (d, J = 7.55 Hz, 1H), 3.87-3.80 (m, 1H), 3.52 (dd, J = 7.03, 12.98 Hz, 2H), 3.24-3.15 (m, 1H), 2.28-2.18 (m, 4H), 2.09-2.06 (m, 2H), 182-1.79 (m, 2H), 1.67-1.56 (m, 6H), 1.52-1.46 (m, 4H), 1.27-1.14 (m, 6H), 1.00 (t, J = 7.35 Hz, 3H); MS m/z 527.00 (M + 1). |
| 13 | UNC972A | ++++ | $^1$H NMR (400 MHz, CDCl$_3$) δ 8.94 (s, 1H), 8.06-8.02 (m, 2H), 7.99-7.96 (m, 2H), 4.75-4.464 (m, 1H), 4.46 (d, J = 7.69 Hz, 1H), 3.53-3.51 (m, 2H), 3.24-3.16 (m, 1H), 2.59-2.49 (m, 1H), 2.41-2.32 (m, 1H), 2.20-2.12 (m, 1H), 2.04-1.96 (m, 4H), 1.87-1.81 (m, 4H), 1.69-1.62 (m, 4H), 1.51-1.43 (m, 4H), 1.27-1.13 (m, 6H), 0.99 (td, J = 0.99, 7.29 Hz, 3H); MS m/z 527.00 (M + 1). |

TABLE 4-continued
| | Structure | Compound_ID | Mer IC$_{50}$ | Physical Data MS m/z (M + 1) or/and $^1$H NMR (400 MHz) |
|---|---|---|---|---|
| 14 | 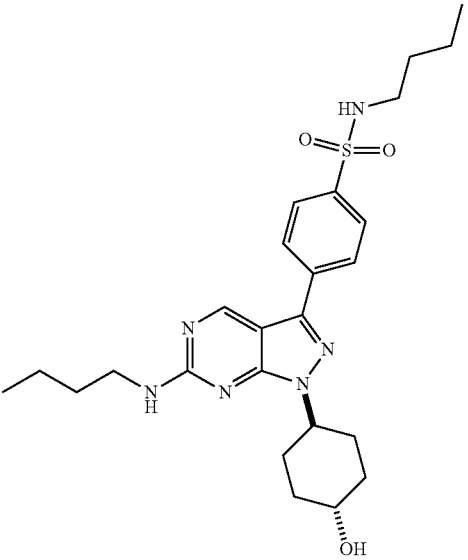 | UNC973A | ++++ | $^1$H NMR (400 MHz, CDCl$_3$) δ 8.85 (s, 1H), 8.02-7.97 (m, 4H), 4.70-4.64 (m, 1H), 4.47 (t, J = 6.18 Hz, 1H), 4.17 (s. 1H), 3.54 (t, J = 8.01 Hz, 2H), 3.01 (dd, J = 6.88, 13.39 Hz, 2H), 2.59-2.50 (m, 2H), 2.04 (d, J = 14.14 Hz, 2H), 1.89-1.67 (m, 6H), 1.51-1.42 (m, 4H), 1.31 (dq, J = 7.25, 14.31 Hz, 2H), 0.99 (t, J = 7.36 Hz, 3H), 0.87 (t, J = 7.32 Hz, 3H)); MS m/z 501.00 (M + 1). |
| 15 | 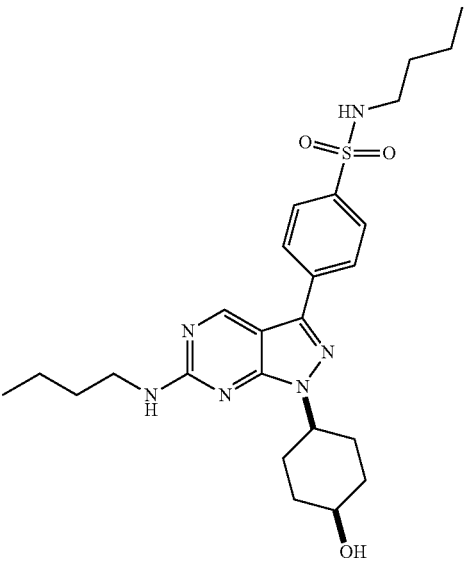 | UNC974A | ++++ | $^1$H NMR (400 MHz, CDCl$_3$) δ 8.85 (s, 1H), 8.00 (s, 4H), 4.73-4.64 (m,1H), 4.45 (t, J = 6.00 Hz, 1H), 3.92-3.84 (m, 1H), 3.54 (s, 2H) 3.01 (dd, J = 6.85, 13.40 Hz, 2H), 2.56-1.99 (m, 6H), 1.88-1.77 (m, 1H), 1.74-1.67 (m, 2H), 1.52-1.42 (m, 5H), 1.34-1.27 (m, 2H), 0.99 (td, J = 1.22, 7.32 Hz, 3H), 0.87 (t, J = 7.32 Hz, 3H)); MS m/z 501.00 (M + 1). |

TABLE 4-continued

| Structure | Compound_ID | Mer IC$_{50}$ | Physical Data MS m/z (M + 1) or/and $^1$H NMR (400 MHz) |
|---|---|---|---|
| 16 | UNC976A | ++++ | $^1$H NMR (400 MHz, CDCl$_3$) δ 8.91 (s, 1H), 8.00 (dd, J = 8.62, 20.77 Hz, 4H), 4.69-4.61 (m, 1H), 4.26 (d, J = 7.61 Hz, 1H), 3.88-3.80 (m, 1H), 3.57-3.48 (m, 2H), 2.27-2.18 (m, 4H), 2.07 (d, J = 10.85 Hz, 2H), 1.71-1.53 (m, 6H), 1.47 (dd, J = 7.36, 14.90 Hz, 2H), 1.11 (d, J = 6.52 Hz, 6H), 0.99 (t, J = 7.34 Hz, 3H); MS m/z 487.30 (M + 1). |
| 17 | UNC977A | ++++ | $^1$H NMR (400 MHz, CDCl$_3$) δ 8.86 (s, 1H), 8.00 (s, 4H), 4.70-4.63 (m, 1H), 4.48 (d, J = 7.67 Hz, 1H), 4.17 (s, 1H), 3.58-3.50 (m, 3H), 2.59-2.33 (m, 2H), 2.04 (d, J = 13.46 Hz, 2H), 1.88-1.67 (m, 6H), 1.51-1.42 (m, 2H), 1.12 (d, J = 6.53 Hz, 6H), 0.99 (t, J = 7.36 Hz, 3H); MS m/z 487.30 (M + 1). |

TABLE 4-continued

| Structure | Compound_ID | Mer IC$_{50}$ | Physical Data MS m/z (M + 1) or/and $^1$H NMR (400 MHz) |
|---|---|---|---|
| 18 | UNC979 A | ++++ | $^1$H NMR (400 MHz, CDCl$_3$) δ 8.73 (s, 1H), 7.71 (d, J = 8.28 Hz, 4H), 7.25 (d, J = 7.44 Hz, 2H), 7.20 (d, J = 7.44 Hz, 2H), 6.83 (s, 1H), 4.62-4.56 (m, 1H), 3.84-3.79 (m, 1H), 3.54-3.50 (m, 2H), 2.38 (s, 3H), 2.22-2.14 (m, 4H), 2.06-2.00 (m, 2H), 1.72-1.65 (m, 2H), 1.60-1.54 (m, 2H), 1.51-1.41 (m, 2H), 0.99 (td, J = 1.03, 7.25 Hz, 3H); MS m/z 535.25 (M + 1). |
| 19 | UNC980 A | +++ | $^1$H NMR (400 MHz, CDCl$_3$) δ 8.69 (s, 1H), 7.73-7.67 (m, 4H), 7.27-7.19 (m, 4H), 7.02 (s, 1H), 4.68-4.64 (m, 1H), 3.90-3.83 (m, 1H), 3.54-3.49 (m, 2H), 2.38 (s, 3H), 2.31 (d, J = 12.05 Hz, 1H), 2.17-2.06 (m, 2H), 2.01-1.96 (m, 3H), 1.70 (dt, J = 7.46, 14.85 Hz, 2H), 1.50-1.37 (m, 4H), 0.98 (t, J = 7.35 Hz, 3H); MS m/z 535.25 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 20 | 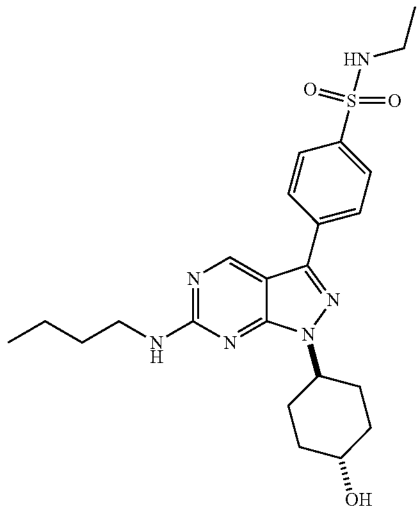 | UNC983 A | ++++ | $^1$H NMR (400 MHz, CDCl$_3$) δ 8.87 (s, 1H), 8.02-7.96 (m, 4H), 4.69-4.60 (m, 1H), 4.35 (t, J = 6.09 Hz, 1H), 2.87-3.79 (m, 1H), 3.53 (dd, J = 6.77, 11.90 Hz, 2H), 3.11-3.04 (m, 2H), 2.20-1.17 (m, 4H), 2.09-2.06 (m, 2H), 1.88 (brs, 2H), 1.72-1.60 (m, 2H), 1.60-1.56 (m, 2H), 1.47 (m, 2H), 1.14 (t, J = 7.24 Hz, 3H), 0.99 (t, J = 7.35 Hz, 3H); MS m/z 473.20 (M + 1). |
| 21 | 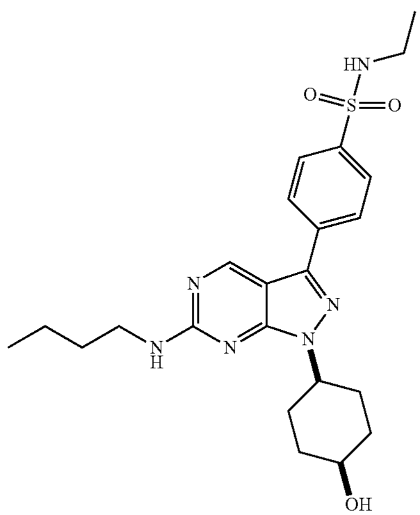 | UNC984 A | ++++ | $^1$H NMR (400 MHz, CDCl$_3$) δ 8.84 (s, 1H), 7.99 (s, 4H), 4.70.4.64 (m, 1H), 4.50-4.47 (m, 1H), 4.17 (s, 1H), 3.88-3.85 (m, 1H), 3.54 (s, 2H), 3.11-3.05 (m, 2H), 2.59-2.50 (m, 1H), 2.37-2.31 (m, 1H), 2.17-1.99 (m, 4H), 1.87-1.77 (m, 2H), 1.71 (dt, J = 6.98, 14.26 Hz, 2H), 1.46 (dq, J = 7.31, 14.50 Hz, 2H), 1.14 (t, J = 7.23 Hz, 3H), 0.99 (t, J = 7.34 Hz, 3H); MS m/z 473.20 (M + 1). |
| 22 | 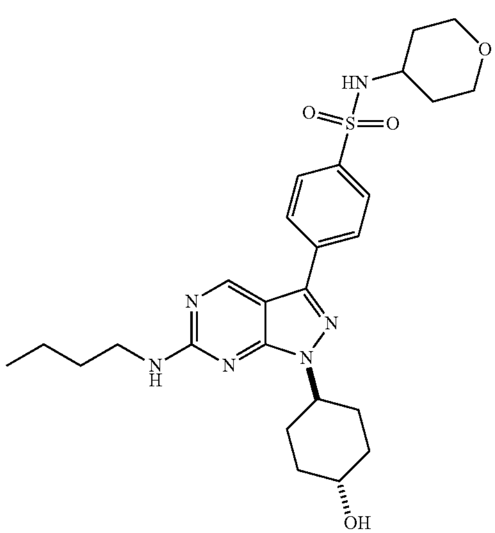 | UNC986 A | ++++ | $^1$H NMR (400 MHz, CDCl$_3$) δ 9.44 (brs, 1H), 8.92 (s, 1H), 8.00 (q, J = 8.67 Hz, 4H), 4.69-4.61 (m, 2H), 3.90-3.84 (m, 4H), 3.55 (t, J = 7.04 Hz, 2H), 3.43-3.33 (m, 2H), 2.21-2.07 (m, 6H), 1.79-1.68 (m, 4H), 1.60-1.44 (m, 6H), 1.00 (t, J = 7.36 Hz, 3H); MS m/z 529.30 (M + 1). |

| Structure | Compound_ID | Mer IC$_{50}$ | Physical Data MS m/z (M + 1) or/and $^1$H NMR (400 MHz) |
|---|---|---|---|
| 23 | UNC987 A | ++++ | $^1$H NMR (400 MHz, CDCl$_3$) δ 8.91 (s, 1H), 8.06-7.97 (m, 4H), 4.48 (d, J = 7.69 Hz, 1H), 3.90-3.85 (m, 2H), 3.55-3.50 (m, 2H), 3.45-3.33 (m, 4H), 2.55-2.49 (m, 1H), 2.35-2.32 (m,1H), 2.04-1.99 (m, 4H), 1.87-1.77 (m, 4H), 1.71-1.64 (m, 3H), 1.53-1.41 (m, 4H), 0.99 (t, J = 7.36 Hz, 3H); MS m/z 529.30 (M + 1). |
| 24 | UNC1029 A | +++ | $^1$H NMR (400 MHz, CDCl$_3$) δ 9.38 (s, 1H), 8.82 (s, 1H), 7.94-7.89 (m, 2H), 7.85-7.81 (m, 2H), 7.09-7.05 (m, 2H), 6.98-6.94 (m, 2H), 6.57 (s, 1H), 4.67-4.61 (m, 1H), 3.98-3.80 (m, 1H), 3.57-3.51 (m, 2H), 2.22-2.08 (m, 6H), 1.71 (dt, J = 7.29, 14.74 Hz, 2H), 1.62-1.57 (m, 2H), 1.45 (dt, J = 7.37, 14.45 Hz, 2H), 0.99 (t, J = 7.38 Hz, 3H); MS m/z 539.30 (M + 1). |
| 25 | UNC1030 A | +++ | $^1$H NMR (400 MHz; CDCl$_3$) δ 8.90 (s, 1H), 7.96 (dd, J = 3.63, 8.55 Hz, 2H), 7.81 (dd, J = 3.50, 8.53 Hz, 2H), 7.09-7.04 (m, 3H), 6.96-6.91 (m, 2H), 4.73-4.63 (m, 1H), 3.90-3.82 (m, 1H), 3.52 (s, 2H), 2.56-2.45 (m, 1H), 2.38-2.31 (m, 1H), 2.20-1.95 (m, 4H), 1.86-1.79 (m, 2H), 1.68-1.62 (m, 2H), 1.50-1.40 (m, 3H), 0.98 (t, J = 7.33 Hz, 3H); MS m/z 539.30 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 26 | 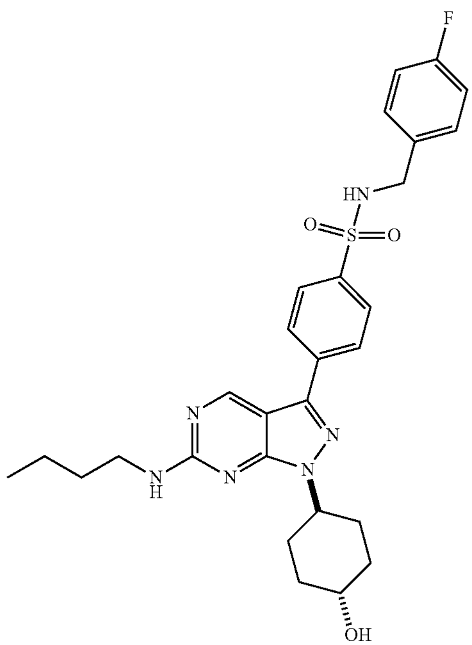 | UNC1032 A | ++++ | $^1$H NMR (400 MHz, CDCl$_3$) δ 8.86 (s, 1H), 8.03-7.95 (m, 4H), 7.26-7.18 (m, 2H), 6.97 (t, J = 8.58 Hz, 2H), 4.74 (t, J = 6.03 Hz, 1H), 4.68-4.66 (m, 1H), 4.17 (d, J = 6.11 Hz, 2H); 3.87-3.81 (m, 1H), 3.54-3.53 (m, 2H), 2.26-2.20 (m, 4H), 2.10-2.03 (m, 4H), 1.69 (dt, J = 7.43, 14.85 Hz, 2H), 1.63-1.54 (m, 1H), 1.52-1.44 (m, 2H), 0.99 (t, J = 7.35 Hz, 3H); MS m/z 553.30 (M + 1). |
| 27 | 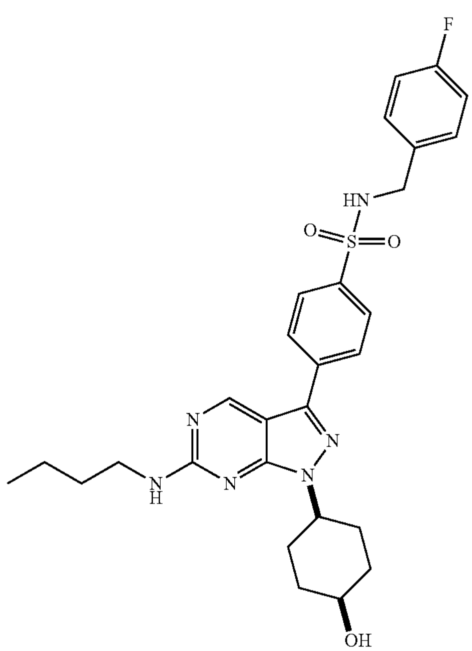 | UNC1033 A | ++++ | $^1$H NMR (400 MHz, CDCl$_3$) δ 9.45 (brs, 1H), 8.88 (s, 1H), 7.97 (s, 4H), 7.20 (dd, J = 5.42, 8.37 Hz, 2H), 6.96 (t, J = 8.55 Hz, 2H), 4.93 (s, 1H), 4.70-4.65 (m, 1H), 4.18 (d, J = 5.60 Hz, 2H), 3.91-3.86 (m, 1H), 3.55 (s, 2H), 2.60-2.51 (m, 1H), 2.36-2.34 (m, 1H), 2.19-2.00 (m, 3H), 1.88-1.81 (m, 2H), 1.72 (dt, J = 7.39, 14.89 Hz, 2H), 1.46 (dd, J = 7.40, 14.91 Hz, 2H), 0.99 (t, J = 7.31 Hz, 3H); MS m/z 553.30 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 28 | 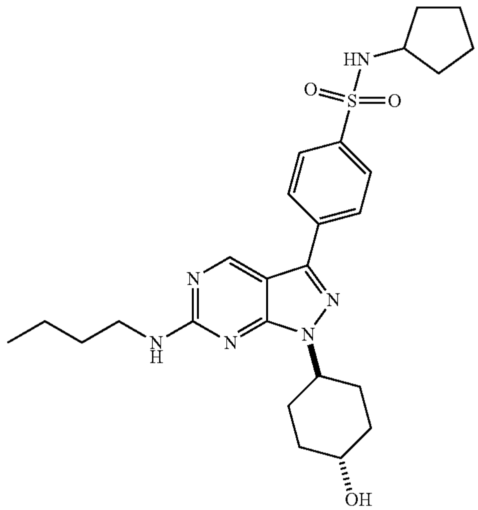 | UNC1035 A | ++++ | $^1$H NMR (400 MHz, CDCl$_3$) δ 8.82 (s, 1H), 7.99 (q, J = 8.67 Hz, 4H), 4.68-4.64 (m, 1H), 4.44 (d, J = 7.34 Hz, 1H), 3.86-3.82 (m, 1H), 3.67 (dd, J = 6.82, 13.53 Hz, 1H), 3.55-3.50 (m, 2H), 2.22-2.16 (m, 4H), 2.10-2.07 (m, 2H), 1.84 (dd, J = 5.70, 12.36 Hz, 2H), 1.71 (dd, J = 7.63, 14.79 Hz, 2H), 1.63-1.57 (m, 4H), 1.54-1.48 (m, 4H), 1.40-1.35 (m, 2H), 1.00 (t, J = 7.35 Hz, 3H); MS m/z 513.30 (M + 1). |
| 29 | 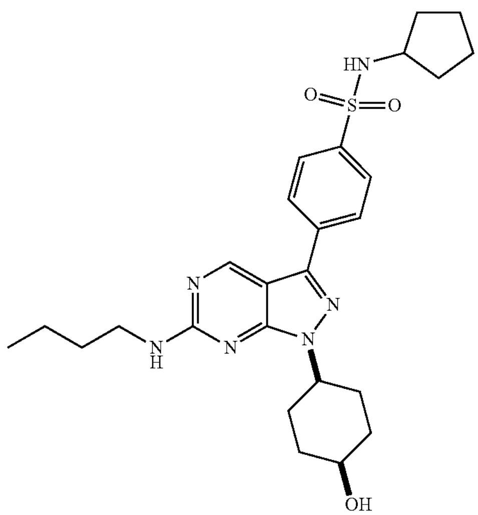 | UNC1036 A | ++++ | $^1$H NMR (400 MHz, CDCl$_3$) δ 8.90 (d, J = 4.54 Hz, 1H), 8.02-7.97 (m, 4H), 4.76-4.63 (m, 2H), 3.91-3.83 (m, 1H), 3.65 (dq, J = 6.83, 13.66 Hz, 1H), 3.53 (s, 2H), 2.59-2.49 (m, 1H), 2.36-2.33 (m, 1H), 2.18-1.97 (m, 4H), 1.88-1.76 (m, 4H), 1.71-1.61 (m, 4H), 1.55-1.33 (m, 6H), 0.98 (td, J = 0.93, 7.32 Hz, 3H); MS m/z 513.30 (M + 1). |
| 30 | 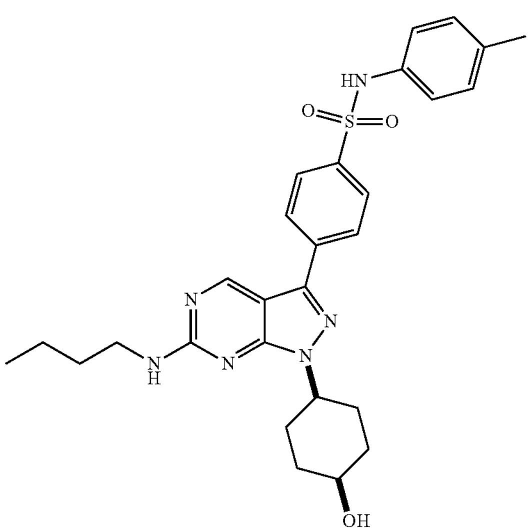 | UNC1039 A | +++ | $^1$H NMR (400 MHz, CDCl$_3$) δ 8.77 (s, 1H), 7.90-7.75 (m, 4H), 7.07 (d, J = 8.40 Hz, 2H), 6.98 (d, J = 8.43 Hz, 2H), 6.38 (s, 1H), 4.71-2.69 (m, 1H), 3.87-3.86 (m, 1H), 3.54-3.52 (m, 2H), 2.29 (s, 3H), 2.17-2.09 (m, 2H), 2.01-1.97 (m, 4H), 1.85-1.76 (m, 2H), 1.74-1.66 (m, 2H), 1.50-1.43 (m, 3H), 0.99 (td, J = 1.10, 7.33 Hz, 3H); MS m/z 535.30 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 31 | 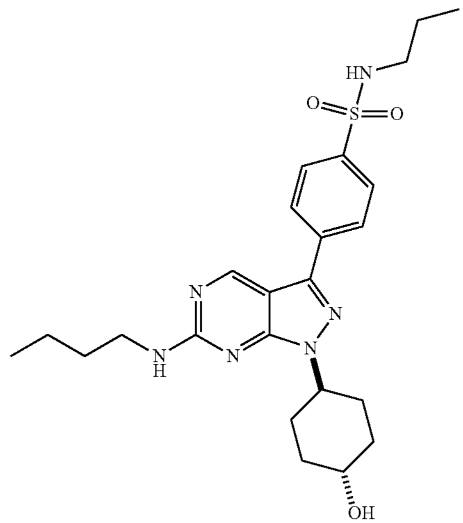 | UNC1059 A | ++++ | $^1$H NMR (400 MHz, CDCl$_3$) δ 8.83 (s, 1H), 7.98 (s, 4H), 4.68-4.62 (m, 1H), 4.42 (t, J = 6.16 Hz 1H), 3.87-3.81 (m, 1H), 3.57-3.51 (m, 2H), 2.98 (dd, J = 6.95, 13.46 Hz, 2H), 2.25-2.16 (m, 4H), 2.10-2.07 (m, 2H), 1.71 (dt, J = 7.43, 14.83 Hz, 2H), 1.60-1.42 (m, 6H), 1.00 (t, J = 7.36 Hz, 3H), 0.89 (t, J = 7.40 Hz, 3H); MS m/z 487.30 (M + 1). |
| 32 | 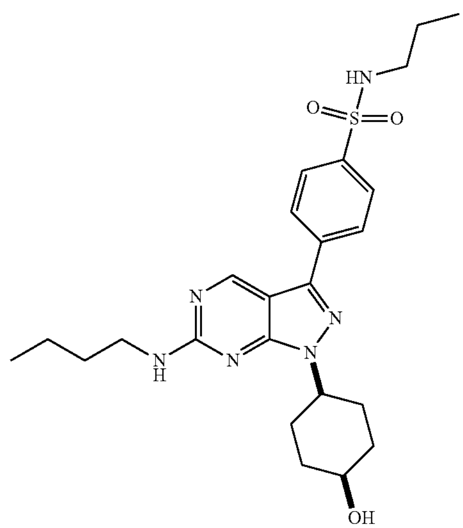 | UNC1061 A | ++++ | $^1$H NMR (400 MHz, CD$_3$OD) δ 9.11-9.09 (m, 1H), 8.18-8.14 (m, 2H), 7.96 (d, J = 8.40 Hz, 2H), 4.74-4.69 (m, 1H), 4.04 (s, 1H), 3.80-3.72 (m, 1H), 3.53-2.48 (m, 2H), 2.86 (t, J = 7.06 Hz, 2H), 2.58-2.48 (m, 1H), 2.41-2.25 (m, 1H), 2.10-1.95 (m, 4H), 1.84-1.78 (m, 2H), 1.71-1.64 (m, 2H), 1.53-1.38 (m, 4H), 1.00 (t, J = 7.36 Hz, 3H), 0.88 (t, J = 7.40 Hz, 3H); MS m/z 487.30 (M + 1). |
| 33 | 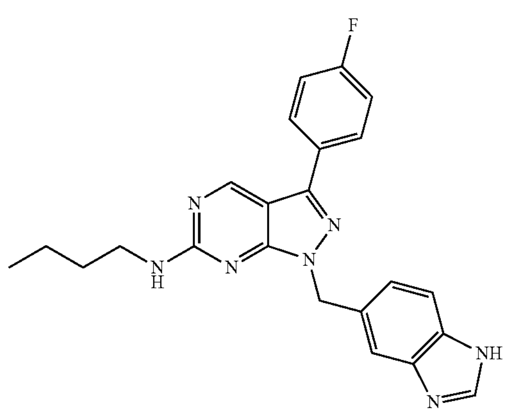 [SMILES: CCCCNc1ncc2c(-c3ccc(F)cc3)nn(Cc3ccc4[nH]cnc4c3)c2n1] | UNC866 A | +++ | $^1$H NMR (400 MHz, CD$_3$OD) δ 9.28 (s, 1H), 9.02 (s, 1H), 7.99-7.91 (m, 2H), 7.80 (d, J = 8.5 Hz, 2H), 7.68 (d, J = 9.4 Hz, 1H), 7.23 (t, J = 8.8 Hz, 2H), 5.70 (s, 2H), 3.49 (t, J = 7.1 Hz, 2H), 1.64 (dt, J = 14.8, 7.3 Hz, 2H), 1.43 (dq, J = 14.6, 7.4 Hz, 2H), 0.95 (t, J = 7.4 Hz, 3H); MS m/z 416.2 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 34 | 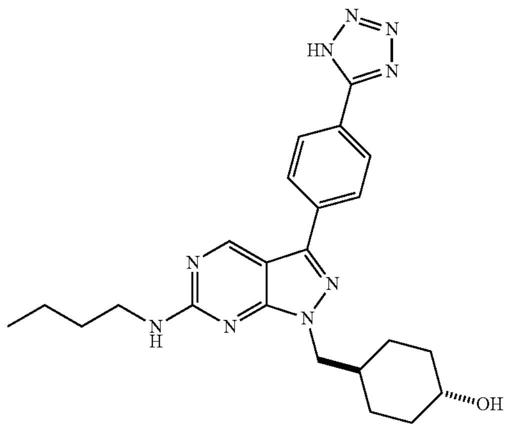 [SMILES: CCCCNc1ncc2c(-c3ccc(-c4nnn[nH]4)cc3)nn(C[C@H]3CC[C@H](O)CC3)c2n1] | UNC842 A | +++ | $^1$H NMR (400 MHz, CD$_3$OD) δ 9.31 (s, 1H), 8.27-8.18 (m, 4H), 4.26 (d, J = 7.0 Hz, 2H), 3.58 (t, J = 7.1 Hz, 2H), 3.55-3.47 (m, 1H), 2.11-1.94 (m, 3H), 1.81-1.68 (m, 4H), 1.49 (td, J = 14.7, 7.3 Hz, 2H), 1.33-1.15 (m, 4H), 1.02 (s, 3H); MS m/z 448.3 (M + 1). |
| 35 | 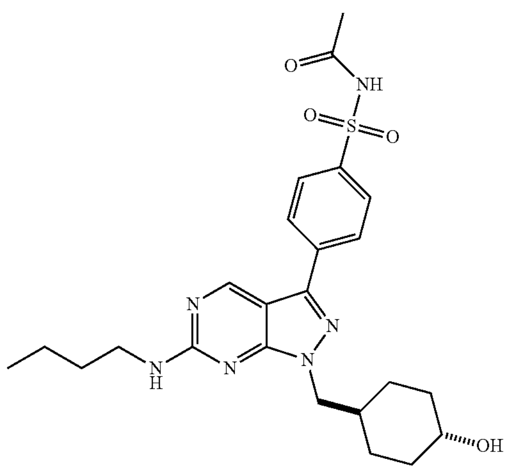 [SMILES: CCCCNc1ncc2c(-c3ccc(S(=O)(=O)NC(C)=O)cc3)nn(C[C@H]3CC[C@H](O)CC3)c2n1] | UNC843 A | +++ | $^1$H NMR (400 MHz, CD$_3$OD) δ 9.30 (s, 1H), 8.18 (q, J = 8.7 Hz, 4H), 4.26 (d, J = 7.0 Hz, 2H), 3.57 (t, J = 7.1 Hz, 2H), 3.54-3.47 (m, 1H), 2.09-1.92 (m, 6H), 1.81-1.67 (m, 4H), 1.48 (dq, J = 14.6, 7.4 Hz, 2H), 1.32-1.16 (m, 4H), 1.02 (t, J = 7.4 Hz, 3H); MS m/z 501.3 (M + 1). |
| 36 | 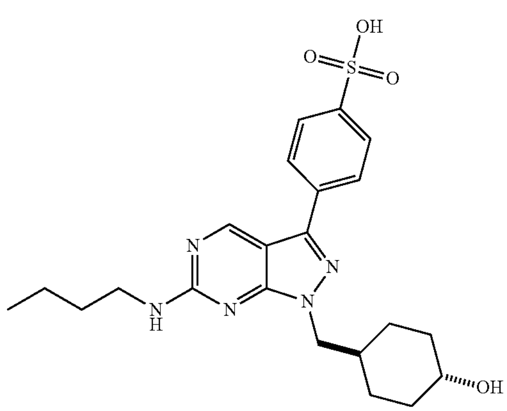 [SMILES: CCCCNc1ncc2c(-c3ccc(S(=O)(=O)O)cc3)nn(C[C@H]3CC[C@H](O)CC3)c2n1] | UNC844 A | +++ | $^1$H NMR (400 MHz, CD$_3$OD) δ 9.23 (s, 1H), 8.08-7.93 (m, 4H), 4.23 (d, J = 7.0 Hz, 2H), 3.60-3.47 (m, 3H), 2.08-1.93 (m, 3H), 1.80-1.65 (m, 4H), 1.47 (td, J = 14.9, 7.4 Hz, 2H), 1.31-1.15 (m, 4H), 1.00 (t, J = 7.4 Hz, 3H); MS m/z 460.2 (M + 1). |

TABLE 4-continued

| | Structure | Compound_ID | Mer IC$_{50}$ | Physical Data<br>MS m/z (M + 1) or/and<br>$^1$H NMR (400 MHz) |
|---|---|---|---|---|
| 37 | (structure with NHMe sulfonamide, phenyl, pyrazolopyrimidine, butylamine, and trans-4-hydroxycyclohexylmethyl) | UNC845 A | +++ | $^1$H NMR (400 MHz, CD$_3$OD) δ 9.30 (s, 1H), 8.20 (d, J = 8.0 Hz, 2H), 8.01 (d, J = 8.0 Hz, 2H), 4.26 (d, J = 7.0 Hz, 2H), 3.58 (t, J = 7.2 Hz, 2H), 3.55-3.45 (m, 1H), 2.58 (s, 3H), 2.11-1.93 (m, 3H), 1.73 (td, J = 14.9, 7.9 Hz, 4H), 1.49 (dq, J = 14.8, 7.5 Hz, 2H), 1.32-1.14 (m, 4H), 1.02 (t, J = 7.7 Hz, 3H); MS m/z 473.3 (M + 1). |
| 38 | (structure with 4-fluorophenyl, pyrazolopyrimidine, butylamine, and cyclohexyl) | UNC784 A | ++ | $^1$HNMR (400 MHz, CDCl$_3$) δ 8.86 (s, 1H), 7.91-7.83 (m, 2H), 7.21-7.12 (m, 2H), 5.44 (s, 1H), 4.59 (tt, J = 11.6, 4.2 Hz, 1H), 3.51 (dd, J = 12.9, 7.0 Hz, 2H), 2.17-1.88 (m, 6H), 1.80-1.71 (m, 1H), 1.70-1.60 (m, 2H), 1.55-1.41 (m, 4H), 1.34 (ddt, J = 16.4, 12.9, 6.3 Hz, 1H), 0.99 (t, J = 7.3 Hz, 3H); MS m/z 368.3 (M + 1). |
| 39 | (structure with CO$_2$H phenyl, pyrazolopyrimidine, butylamine, and trans-4-aminocyclohexylmethyl) | UNC785 A | +++ | $^1$H NMR (400 MHz, DMSO-d$_6$) δ 13.07 (bs, 1H), 9.19 (s, 1H), 8.16-7.99 (m, 4H), 7.70 (bs, 2H), 4.14 (d, J = 5.4 Hz, 2H), 3.39-3.29 (m, 2H), 2.95 (bs, 1H), 1.98-1.82 (m, 3H), 1.68 (d, J = 11.6 Hz, 2H), 1.62-1.51 (m, 2H), 1.36 (dt, J = 14.4, 7.3 Hz, 2H), 1.31-1.08 (m, 5H), 0.92 (t, J = 7.3 Hz, 3H); MS m/z 423.3 (M + 1). |
| 40 | (structure with NHMe sulfonamide, phenyl, pyrazolopyrimidine, butylamine, and cyclohexyl) | UNC904 A | ++ | $^1$H NMR (400 MHz, CDCl$_3$) δ 8.94 (s, 1H), 8.10-8.03 (m, 2H), 7.99-7.92 (m, 2H), 5.30 (bs, 1H), 4.68-4.56 (m, 1H), 4.33 (q, J = 5.4 Hz, 1H), 3.52 (dd, J = 12.9, 7.0 Hz, 2H), 2.70 (d, J = 5.4 Hz, 3H), 2.16-1.89 (m, 6H), 1.77 (d, J = 12.7 Hz, 1H), 1.66 (dt, J = 14.8, 7.3 Hz, 2H), 1.54-1.28 (m, 5H), 0.99 (t, J = 7.3 Hz, 3H); MS m/z 443.2 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 41 | 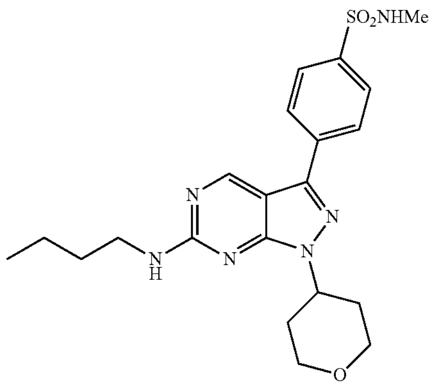 | UNC905 A | +++ | $^1$H NMR (400 MHz, CDCl$_3$) δ 8.96 (s, 1H), 8.07 (d, J = 8.5 Hz, 2H), 7.97 (d, J = 8.5 Hz, 2H), 5.33 (s, 1H), 4.92-4.79 (m, 1H), 4.32 (dd, J = 10.8, 5.4 Hz, 1H), 4.17 (dd, J = 11.7, 3.3 Hz, 2H), 3.64 (dd, J = 11.9, 10.2 Hz, 2H), 3.52 (dd, J = 12.9, 6.9 Hz, 2H), 2.71 (d, J = 5.4 Hz, 3H), 2.48 (ddd, J = 25.0, 12.5, 4.7 Hz, 2H), 1.97 (d, J = 10.8 Hz, 2H), 1.66 (dt, J = 14.8, 7.2 Hz, 2H), 1.47 (dq, J = 14.5, 7.3 Hz, 2H), 0.99 (t, J = 7.3 Hz, 3H); MS m/z 445.2 (M + 1). |
| 42 | 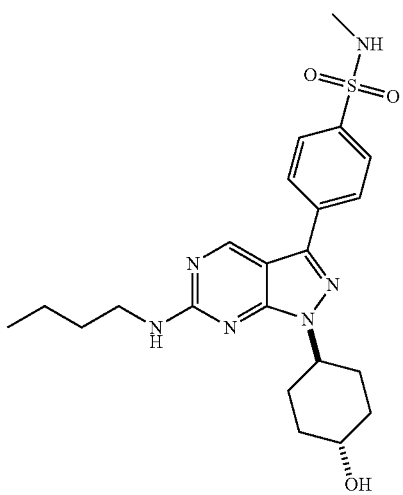 | UNC906 A | ++++ | $^1$H NMR (400 MHz, CDCl$_3$ + CD$_3$OD) δ 8.78 (s, 1H), 7.92 (d, J = 8.4 Hz, 2H), 7.82 (d, J = 8.3 Hz, 2H), 4.51 (s, 1H), 3.64 (s, 1H), 3.37 (t, J = 7.0 Hz, 2H), 2.50 (s, 3H), 2.17-1.86 (m, 6H), 1.61-1.29 (m, 6H), 0.87 (t, J = 7.3 Hz, 3H); MS m/z 459.2 (M + 1). |
| 43 | 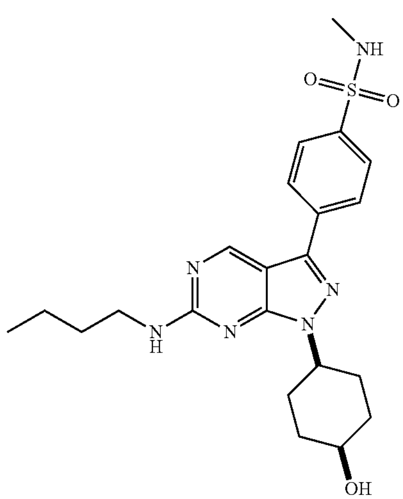 | UNC907 A | ++++ | $^1$H NMR (400 MHz, CDCl$_3$ + CD$_3$OD) δ 8.82 (s, 1H), 7.95 (dd, J = 8.2, 6.2 Hz, 2H), 7.84 (dd, J = 8.5, 1.8 Hz, 2H), 4.66-4.48 (m, 1H), 3.44-3.33 (m, 3H), 2.53 (s, 3H), 2.46-2.32 (m, 1H), 1.99-1.81 (m, 3H), 1.79-1.61 (m, 3H), 1.55 (dt, J = 14.8, 7.4 Hz, 2H), 1.36 (td, J = 14.8, 7.4 Hz, 3H), 0.88 (t, J = 7.3 Hz, 3H); MS m/z 459.2 (M + 1). |

TABLE 4-continued

| Structure | Compound_ID | Mer IC$_{50}$ | Physical Data MS m/z (M + 1) or/and $^1$H NMR (400 MHz) |
|---|---|---|---|
| 44 | UNC908 A | +++ | $^1$H NMR (400 MHz, CDCl$_3$) δ 8.95 (s, 1H), 8.10-8.03 (m, 2H), 8.00-7.93 (m, 2H), 5.37 (bs, 1H), 4.41-4.30 (m, 1H), 4.24 (d, J = 7.1 Hz, 2H), 4.03-3.91 (m, 2H), 3.51 (dd, J = 13.0, 6.9 Hz, 2H), 3.38 (td, J = 11.5, 2.6 Hz, 2H), 2.71 (d, J = 5.4 Hz, 3H), 2.40-2.24 (m, 1H), 1.71-1.61 (m, 2H), 1.60-1.56 (m, 1H), 1.54-1.38 (m, 5H), 0.99 (t, J = 7.3 Hz, 3H); MS m/z 459.3 (M + 1). |
| 45 | UNC909 A | +++ | $^1$H NMR (400 MHz, CDCl$_3$) δ 8.95 (s, 1H), 8.10-8.03 (m, 2H), 7.99-7.93 (m, 2H), 5.38 (bs, 1H), 4.47-4.33 (m, 3H), 3.95 (dd, J = 11.5, 3.5 Hz, 2H), 3.49 (dd, J = 13.1, 6.8 Hz, 2H), 3.33 (td, J = 11.7, 1.8 Hz, 2H), 2.71 (d, J = 5.4 Hz, 3H), 1.97-1.86 (m, 2H), 1.76 (d, J = 12.7 Hz, 2H), 1.65 (dt, J = 12.7, 7.4 Hz, 2H), 1.55-1.30 (m, 5H), 0.98 (t, J = 7.3 Hz, 3H); MS m/z 473.3 (M + 1). |
| 46 | UNC910 A | ++ | $^1$H NMR (400 MHz, CDCl$_3$) δ 8.94 (s, 1H), 8.09-8.01 (m, 2H), 8.00-7.92 (m, 2H), 5.37 (s, 1H), 4.49-4.34 (m, 3H), 3.76-3.60 (m, 4H), 3.50 (dd, J = 13.0, 6.9 Hz, 2H), 2.71 (d, J = 5.4 Hz, 3H), 2.44 (bs, 4H), 2.19-2.07 (m, 2H), 1.71-1.53 (m, 4H), 1.51-1.37 (m, 2H), 0.98 (t, J = 7.3 Hz, 3H); MS m/z 488.3 (M + 1). |

TABLE 4-continued

| Structure | Compound_ID | Mer IC$_{50}$ | Physical Data MS m/z (M + 1) or/and $^1$H NMR (400 MHz) |
|---|---|---|---|
| 47 | UNC911 A | +++ | $^1$H NMR (400 MHz, CDCl$_3$) δ 8.79 (s, 1H), 7.92 (d, J = 8.6 Hz, 2H), 7.83 (d, J = 8.6 Hz, 2H), 4.24 (t, J = 7.0 Hz, 2H), 3.45-3.30 (m, 3H), 2.50 (s, 3H), 1.81 (t, J = 11.5 Hz, 3H), 1.71 (dd, J = 13.7, 6.8 Hz, 2H), 1.53 (dt, J = 14.9, 7.3 Hz, 2H), 1.40-1.27 (m, 2H), 1.08 (dd, J = 23.1, 12.5 Hz, 4H), 1.00-0.89 (m, 2H), 0.86 (t, J = 7.9 Hz, 3H); MS m/z 487.3 (M + 1). |
| 48 | UNC912 A | +++ | $^1$H NMR (400 MHz, CD$_3$OD) δ 9.03 (s, 1H), 8.17-8.09 (m, 2H), 7.99-7.92 (m, 2H), 4.32 (t, J = 6.9 Hz, 2H), 3.48 (t, J = 7.0 Hz, 2H), 3.42 (dt, J = 10.8, 4.2 Hz, 1H), 2.58 (s, 3H), 2.02-1.84 (m, 4H), 1.76 (d, J = 11.6 Hz, 2H), 1.66 (dt, J = 14.8, 7.3 Hz, 2H), 1.52-1.39 (m, 2H), 1.29-1.13 (m, 5H), 0.99 (t, J = 7.4 Hz, 3H), 0.96-0.86 (m, 2H); MS m/z 501.3 (M + 1). |
| 49 | UNC913 A | ++++ | $^1$H NMR (400 MHz, CD$_3$OD) δ 9.17 (s, 1H), 8.20-8.14 (m, 2H), 8.01-7.95 (m, 2H), 4.26 (d, J = 6.8 Hz, 2H), 3.52 (t, J = 7.1 Hz, 2H), 3.13-3.00 (m, 1H), 2.81 (s, 3H), 2.15-2.01 (m, 3H), 1.86 (d, J = 12.0 Hz, 2H), 1.68 (dt, J = 12.7, 7.4 Hz, 2H), 1.48 (dt, J = 14.8, 7.3 Hz, 2H), 1.41-1.21 (m, 4H), 1.00 (t, J = 7.4 Hz, 3H); MS m/z 472.3 (M + 1). |

TABLE 4-continued

| Structure | Compound_ID | Mer IC$_{50}$ | Physical Data MS m/z (M + 1) or/and $^1$H NMR (400 MHz) |
|---|---|---|---|
| 50 | UNC914 A | +++ | $^1$H NMR (400 MHz, CD$_3$OD) δ 9.13 (s, 1H), 8.17 (d, J = 8.4 Hz, 2H), 7.97 (d, J = 8.5 Hz, 2H), 4.34 (d, J = 6.7 Hz, 2H), 3.50 (t, J = 7.1 Hz, 2H), 3.41 (d, J = 12.8 Hz, 2H), 3.00 (td, J = 12.8, 2.7 Hz, 2H), 2.58 (s, 3H), 2.46-2.34 (m, 1H), 1.95 (d, J = 12.7 Hz, 2H), 1.74-1.53 (m, 4H), 1.51-1.39 (m, 2H), 1.00 (t, J = 7.4 Hz, 3H); MS m/z 458.3 (M + 1). |
| 51 | UNC958 A | +++ | $^1$H NMR (400 MHz, CD$_3$OD) δ 9.09 (s, 1H), 8.02-7.93 (m, 2H), 7.32-7.22 (m, 2H), 4.27 (d, J = 7.9 Hz, 2H), 3.52 (t, J = 7.1 Hz, 2H), 2.24-2.09 (m, 1H), 1.88 (d, J = 15.8 Hz, 2H), 1.79-1.55 (m, 6H), 1.52-1.38 (m, 4H), 1.34 (s, 3H), 1.00 (t, J = 7.4 Hz, 3H); MS m/z 411.3 (M + 1). |
| 52 | UNC988 A | +++ | $^1$H NMR (400 MHz, CDCl$_3$) δ 8.94 (s, 1H), 8.10-8.04 (m, 2H), 7.99-7.93 (m, 2H), 5.31 (bs, 1H), 5.05 (dt, J = 13.3, 6.7 Hz, 1H), 4.35 (q, J = 5.4 Hz, 1H), 3.51 (dd, J = 12.9, 7.0 Hz, 2H), 2.71 (d, J = 5.4 Hz, 3H), 1.70-1.61 (m, 2H), 1.59 (d, J = 6.7 Hz, 6H), 1.52-1.41 (m, 2H), 0.99 (t, J = 7.3 Hz, 3H); MS m/z 403.0 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 53 | 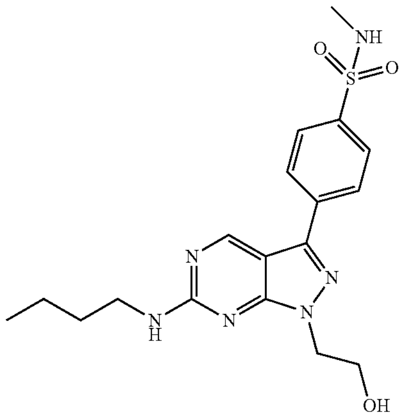 [SMILES: CCCCNc1ncc2c(-c3ccc(S(=O)(=O)NC)cc3)nn(CCO)c2n1] | UNC989 A | ++ | $^1$H NMR (400 MHz, CDCl$_3$) δ 8.86 (s, 1H), 8.00-7.92 (m, 2H), 7.91-7.83 (m, 2H), 4.42 (t, J = 5.0 Hz, 2H), 4.01 (t, J = 5.0 Hz, 2H), 3.38 (t, J = 7.1 Hz, 3H), 2.56 (s, 3H), 1.63-1.50 (m, 2H), 1.44-1.30 (m, 2H), 0.90 (t, J = 7.3 Hz, 3H); MS m/z 405.2 (M + 1). |
| 54 | 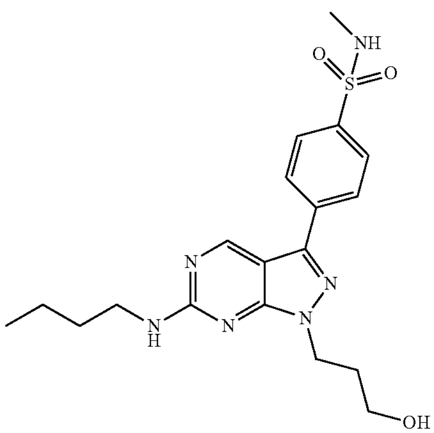 [SMILES: CCCCNc1ncc2c(-c3ccc(S(=O)(=O)NC)cc3)nn(CCCO)c2n1] | UNC990 A | ++ | $^1$H NMR (400 MHz, CDCl$_3$) δ 8.88 (s, 1H), 7.98 (d, J = 8.6 Hz, 2H), 7.90 (d, J = 8.6 Hz, 2H), 4.43 (t, J = 6.2 Hz, 2H), 3.50 (t, J = 5.8 Hz, 2H), 3.40 (t, J = 7.1 Hz, 2H), 2.59 (s, 3H), 2.10-2.00 (m, 2H), 1.60 (dt, J = 14.9, 7.4 Hz, 2H), 1.40 (dq, J = 14.5, 7.3 Hz, 2H), 0.92 (t, J = 7.3 Hz, 3H); MS m/z 419.2 (M + 1). |
| 55 | 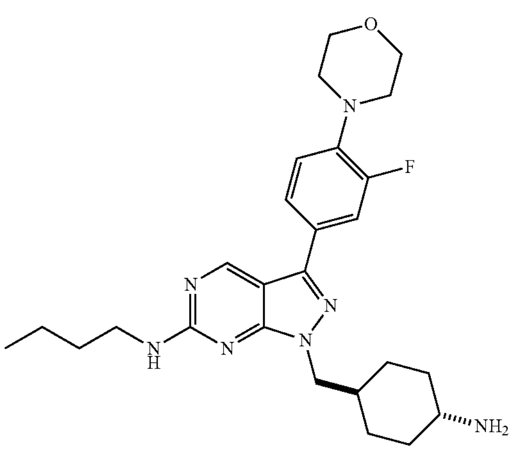 [SMILES: CCCCNc1ncc2c(-c3ccc(N4CCOCC4)c(F)c3)nn(C[C@H]3CC[C@H](N)CC3)c2n1] | UNC1084 A | ++++ | $^1$H NMR (400 MHz, CDCl$_3$ + CD$_3$OD) δ 8.74 (s, 1H), 7.51-7.41 (m, 2H), 6.94 (t, J = 8.6 Hz, 1H), 4.04 (d, J = 6.8 Hz, 2H), 3.80-3.74 (m, 4H), 3.35 (t, J = 7.0 Hz, 2H), 3.10-3.01 (m, 4H), 2.87 (dd, J = 13.6, 9.7 Hz, 1H), 1.93 (d, J = 10.1 Hz, 3H), 1.70 (d, J = 12.7 Hz, 2H), 1.58-1.47 (m, 2H), 1.33 (td, J = 14.6, 7.2 Hz, 2H), 1.27-1.17 (m, 2H), 1.09 (dd, J = 24.2, 11.9 Hz, 2H), 0.86 (t, J = 7.3 Hz, 3H); MS m/z 482.4 (M + 1). |

TABLE 4-continued

| | Structure | Compound_ID | Mer IC$_{50}$ | Physical Data MS m/z (M + 1) or/and $^1$H NMR (400 MHz) |
|---|---|---|---|---|
| 56 | 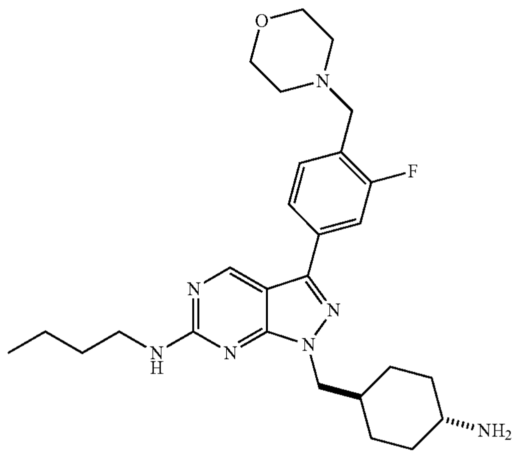 [SMILES: CCCCNc1ncc2c(-c3ccc(CN4CCOCC4)c(F)c3)nn(C[C@H]3CC[C@H](N)CC3)c2n1] | UNC1085 A | ++++ | $^1$H NMR (400 MHz, CD$_3$OD) δ 9.25 (s, 1H), 7.90 (ddd, J = 12.1, 9.3, 1.6 Hz, 2H), 7.76 (t, J = 7.7 Hz, 1H), 4.52 (s, 2H), 4.26 (d, J = 6.8 Hz, 2H), 3.98 (bs, 4H), 3.54 (t, J = 7.1 Hz, 2H), 3.40 (bs, 4H), 3.07 (ddd, J = 11.6, 7.7, 4.0 Hz, 1H), 2.16-2.02 (m, 3H), 1.86 (d, J = 11.7 Hz, 2H), 1.75-1.64 (m, 2H), 1.53-1.22 (m, 6H), 1.00 (t, J = 7.4 Hz, 3H); MS m/z 496.3 (M + 1). |
| 57 | 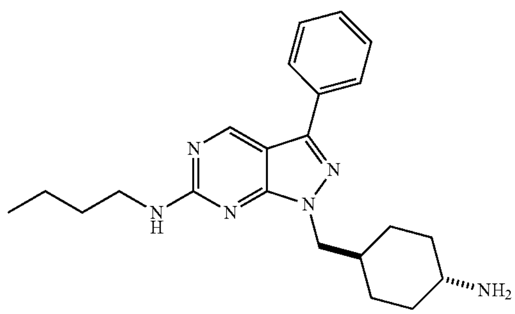 [SMILES: CCCCNc1ncc2c(-c3ccccc3)nn(C[C@H]3CC[C@H](N)CC3)c2n1] | UNC1167 A | ++++ | $^1$H NMR (400 MHz, CD$_3$OD) δ 9.10 (s, 1H), 7.94 (d, J = 7.0 Hz, 2H), 7.60-7.87 (m, 3H), 4.24 (d, J = 6.7 Hz, 2H), 3.52 (t, J = 7.0 Hz, 2H), 3.14-2.99 (m, 1H), 2.17-1.98 (m, 3H), 1.86 (d, J = 12.6 Hz, 2H), 1.75-1.60 (m, 2H), 1.55-1.20 (m, 6H), 1.01 (t, J = 7.3 Hz, 3H); MS m/z 379.3 (M + 1). |
| 58 | 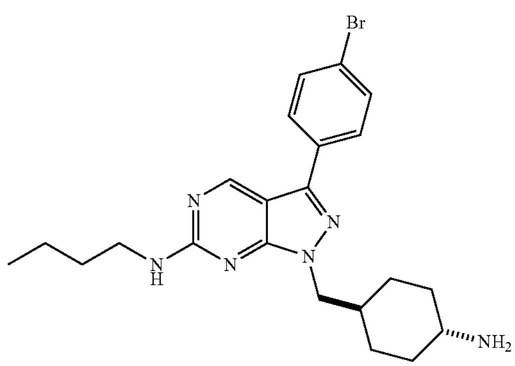 [SMILES: CCCCNc1ncc2c(-c3ccc(Br)cc3)nn(C[C@H]3CC[C@H](N)CC3)c2n1] | UNC1168 A | ++++ | $^1$H NMR (400 MHz, CD$_3$OD) δ 9.05 (s, 1H), 7.86 (d, J = 8.4 Hz, 2H), 7.67 (d, J = 8.4 Hz, 2H), 4.21 (d, J = 6.7 Hz, 2H), 3.49 (t, J = 7.0 Hz, 2H), 3.14-3.00 (m, 1H), 2.14-1.98 (m, 3H), 1.83 (d, J = 12.3 Hz, 2H), 1.73-1.61 (m, 2H), 1.53-1.19 (m, 6H), 1.00 (t, J = 7.3 Hz, 3H); MS m/z 457.2 (M + 1). |
| 59 | 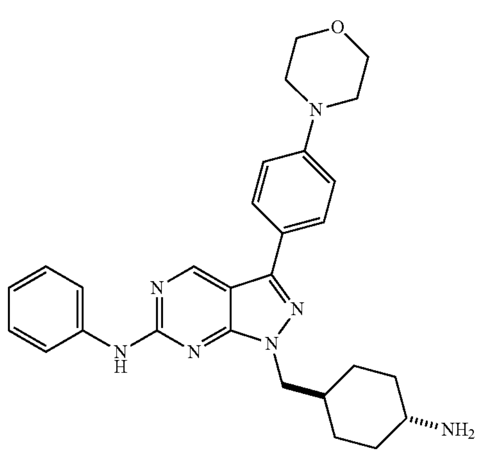 [SMILES: N[C@H]1CC[C@H](Cn2nc(-c3ccc(N4CCOCC4)cc3)c3cnc(Nc4ccccc4)nc32)CC1] | UNC1306 A | +++ | $^1$H NMR (400 MHz, DMSO-d$_6$) δ 10.02 (s, 1H), 9.32 (s, 1H), 8.01 (bs, 2H), 7.91 (dd, J = 12.8, 8.5 Hz, 4H), 7.35 (t, J = 7.9 Hz, 2H), 7.14 (d, J = 8.7 Hz, 2H), 7.00 (t, J = 7.3 Hz, 1H), 4.19 (d, J = 6.8 Hz, 2H), 3.81 (m, 4H), 3.29-3.19 (m, 4H), 2.94 (bs, 1H), 2.06-1.89 (m, 3H), 1.71 (d, J = 11.0 Hz, 2H), 1.38-1.24 (m, 2H), 1.24-1.09 (m, 2H); MS m/z 484.3 (M + 1). |

TABLE 4-continued

| Structure | Compound_ID | Mer IC$_{50}$ | Physical Data MS m/z (M + 1) or/and $^1$H NMR (400 MHz) |
|---|---|---|---|
| 60 | UNC1307A | +++ | $^1$H NMR (400 MHz, DMSO-d$_6$) δ 10.01 (s, 1H), 9.31 (s, 1H), 7.97 (bs, 2H), 7.92 (d, J = 8.8 Hz, 2H), 7.79 (t, J = 2.1 Hz, 1H), 7.36 (d, J = 9.3 Hz, 1H), 7.22 (t, J = 8.1 Hz, 1H), 7.12 (d, J = 8.8 Hz, 2H), 6.58 (dd, J = 8.1, 2.3 Hz, 1H), 4.19 (d, J = 6.8 Hz, 2H), 3.81-3.77 (m, 7H), 3.28-3.18 (m, 4H), 2.93 (bs, 1H), 2.07-1.88 (m, 3H), 1.70 (d, J = 11.2 Hz, 2H), 1.29 (dd, J = 24.0, 11.7 Hz, 2H), 1.18 (dd, J = 24.0, 12.2 Hz, 2H); MS m/z 514.3 (M + 1). |
| 61 | UNC1308A | +++ | $^1$H NMR (400 MHz, DMSO-d$_6$) δ 9.84 (s, 1H), 9.26 (s, 1H), 7.95 (bs, 2H), 7.90 (d, J = 8.6 Hz, 2H), 7.77 (d, J = 8.8 Hz, 2H), 7.11 (d, J = 8.7 Hz, 2H), 6.94 (d, J = 9.0 Hz, 2H), 4.16 (d, J = 6.5 Hz, 2H), 3.83-3.77 (m, 4H), 3.75 (s, 3H), 3.27-3.17 (m, 4H), 2.96 (s, 1H), 1.95 (d, J = 9.3 Hz, 3H), 1.71 (d, J = 11.7 Hz, 2H), 1.30 (dd, J = 24.4, 11.8 Hz, 2H), 1.17 (dd, J = 25.2, 12.5 Hz, 2H); MS m/z 514.3 (M + 1). |

Example 5

The R$^1$ Position 1-(4-Hydroxy-cyclohexyl)-3-(4-piperidinsulfonyl-phenyl)-1H-pyrazolo[3,4-d]pyrimidin-6-amine General Procedure E:

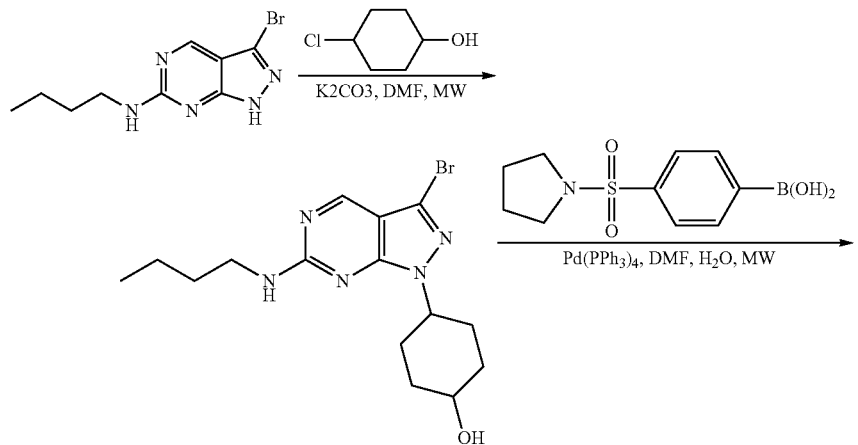

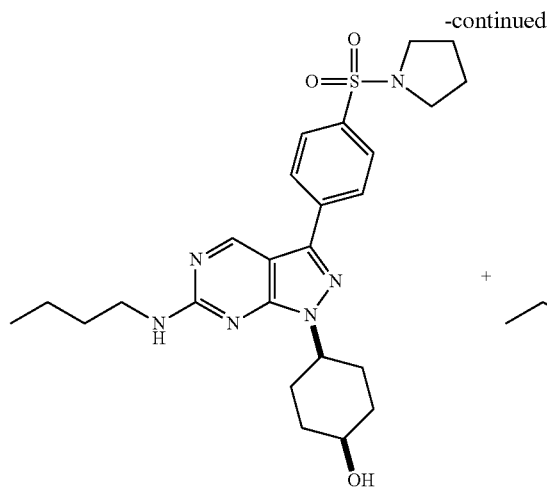

1-(4-hydroxy-cyclohexyl)-3-bromo-N-butyl-1H-pyrazolo[3,4-d]pyrimidin-6-amine

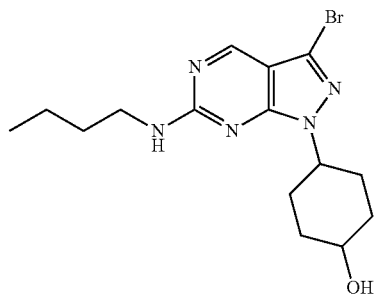 [SMILES: CCCCNc1ncc2c(Br)nn(C3CCC(O)CC3)c2n1]

To a solution of 3-bromo-N-butyl-1H-pyrazolo[3,4-d]pyrimidin-6-amine (122 mg, 0.45 mmol) and 4-hydroxy-cyclohexyl chloride (260 mg, 1.9 mmol) in DMF (6.0 mL) was added K$_2$CO$_3$ (270 g, 2.0 mmol). The mixture was heated at 150° C. for overnight. After the reaction was cooled to room temperature, the reaction was quenched with H$_2$O. The reaction mixture was partitioned in H$_2$O and EtOAc. The aqueous phase was extracted with EtOAc (3×). The combined organic phase were dried (Na$_2$SO$_4$) and concentrated. The residue was purified by Isco to provide a mixture of cis- and trans-1-(4-hydroxy-cyclohexyl)-3-bromo-N-butyl-1H-pyrazolo[3,4-d]pyrimidin-6-amine (90 mg, 54%) as a yellow solid.

1-(4-hydroxy-cyclohexyl)-3-(4-piperidinsulfonyl-phenyl)-1H-pyrazolo[3,4-d]pyrimidin-6-amine

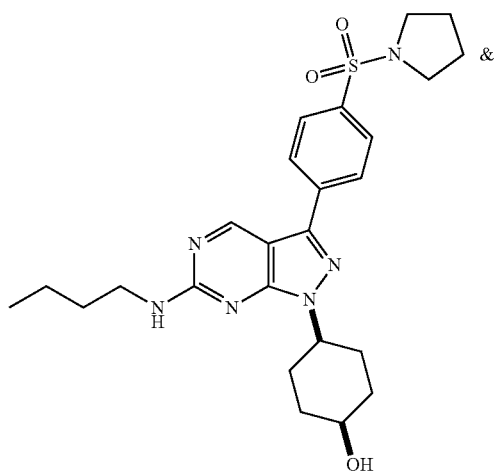

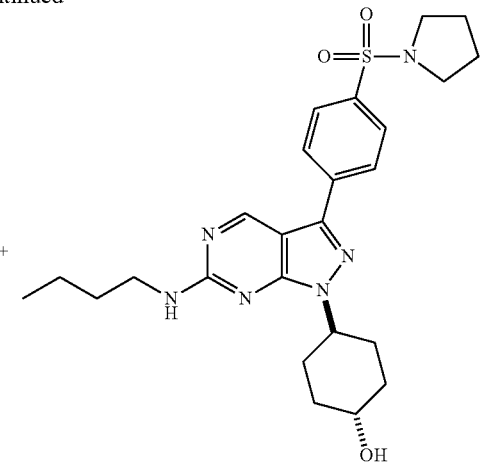

-continued

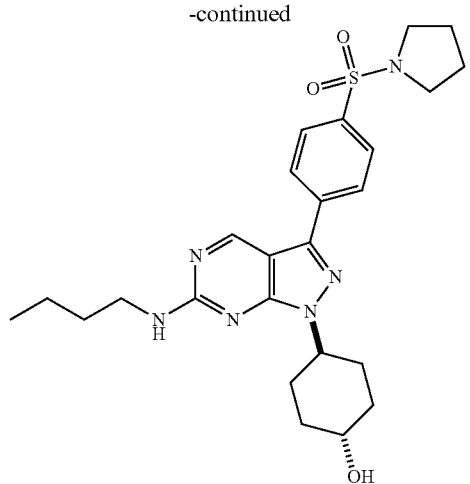

A 10 mL microwave tube was charged with 1-(4-hydroxy-cyclohexyl)-3-bromo-N-butyl-1H-pyrazolo[3,4-d]pyrimidin-6-amine (0.070 g, 0.19 mmol), (4-piperidinsulfonyl)phenyl boronic acid (0.10 g, 0.40 mmol), potassium carbonate (0.086 g, 0.62 mmol), tetrakis(triphenylphosphine)palladium (0.025 g, 0.022 mmol), DMF (2.0 mL) and water (0.50 mL). After stirring for 5 min, the reaction was heat at 150° C. for 10 min in microwave. The reaction was diluted with EtOAc and washed with water. The aqueous layer was extracted with EtOAc (3×). The combined organic layers were dried (Na$_2$SO$_4$), concentrated, and purified by Isco and HPLC to provide cis-1-(4-hydroxy-cyclohexyl)-3-(4-piperidinsulfonyl-phenyl)-1H-pyrazolo[3,4-d]pyrimidin)-6-amine (UNC1065A) (0.011 g, 12%) as a white solid, $^1$H NMR (400 MHz, CD$_3$OD). δ 9.21 (s, 1H), 8.22 (d, J=8.4 Hz, 2H), 7.98 (d, J=8.4 Hz, 2H), 4.79-4.69 (m, 1H), 4.08-4.02 (m, 1H), 3.55 (t, J=7.1 Hz, 2H), 3.32-3.25 (m, 4H), 2.62-2.46 (m, 2H), 2.07-1.96 (m, 2H), 1.89-1.65 (m, 10H), 1.48 (qd, J=14.5, 7.3 Hz, 2H), 1.01 (t, J=7.4 Hz, 3H); MS m/z 499.0 [M+1]$^+$, and trans-1-(4-hydroxy-cyclohexyl)-3-(4-piperidinsulfonyl-phenyl)-1H-pyrazolo[3,4-d]pyrimidin-6-amine (UNC1064A) (0.009 g, 10%) as a white solid. $^1$H NMR (400 MHz, CD$_3$OD). δ 9.20 (s, 1H), 8.20 (d, J=8.5 Hz, 2H), 7.98 (d, J=8.5 Hz, 2H), 4.75-4.64 (m, 1H), 3.78-3.67 (m, 1H), 3.55 (t, J=7.1 Hz, 2H), 3.32-3.23 (m, 4H), 2.30-2.02 (m, 6H), 1.85-1.64 (m, 6H), 1.62-1.42 (m, 4H), 1.02 (t, J=7.4 Hz, 3H); MS m/z 499.0 [M+1]$^+$.

Table 5 describes compounds prepared following procedures described in Example 5 (General Procedure E), using appropriate reagents.

TABLE 5

| | Structure | Compound_ID | Mer IC$_{50}$ | Physical Data MS m/z (M + 1) or/and $^1$H NMR (400 MHz) |
|---|---|---|---|---|
| 1 | 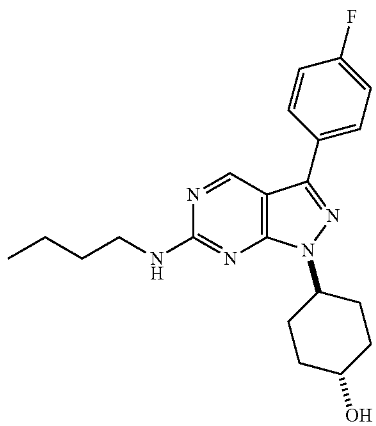 | UNC1060A | +++ | $^1$H NMR (400 MHz, CD$_3$OD) δ 9.07 (s, 1H), 8.04-7.96 (m, 2H), 7.30-7.22 (m, 2H), 4.75-4.64 (m, 1H), 4.07-4.02 (m, 1H), 3.53 (t, J = 7.1 Hz, 2H), 2.60-2.46 (m, 2H), 2.06-1.96 (m, 2H), 1.86-1.73 (m, 4H), 1.73-1.64 (m, 2H), 1.47 (dq, J = 14.5, 7.3 Hz, 2H), 1.01 (t, J = 7.4 Hz, 3H); MS m/z 384.2 (M + 1). |
| 2 | 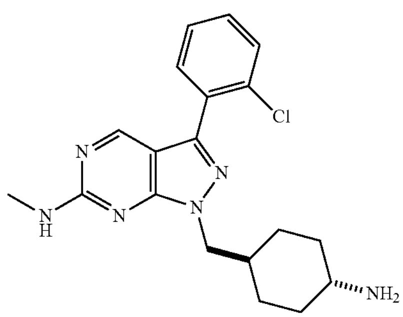 [SMILES: CNc1ncc2c(-c3ccccc3Cl)nn(C[C@H]3CC[C@H](N)CC3)c2n1] | UNC1040A | ++ | $^1$H NMR (400 MHz, CD$_3$OD). δ 8.87 (s, 1H), 7.67-7.59 (m, 2H), 7.55-7.45 (m, 2H), 4.28 (d, J = 6.9 Hz, 2H), 3.13-3.03 (m, 1H), 3.08 (s, 3H), 2.16-2.03 (m, 3H), 1.92-1.81 (m, 2H), 1.48-1.23 (m, 4H); MS m/z 371.2 (M + 1). |
| 3 | 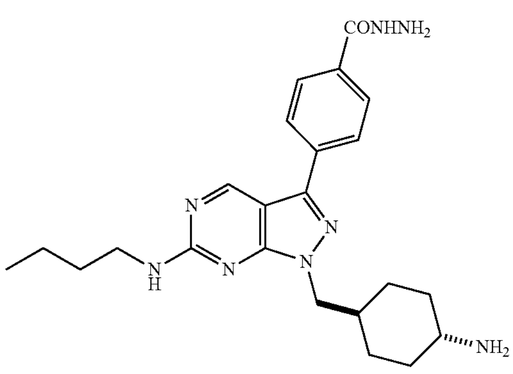 | UNC1058A | ++++ | $^1$H NMR (400 MHz, CD$_3$OD). δ 9.20 (s, 1H), 8.14 (d, J = 8.4 Hz, 2H), 8.05 (d, J = 8.4 Hz, 2H), 4.27 (d, J = 6.8 Hz, 2H), 3.53 (t, J = 7.1 Hz, 2H), 3.13-3.02 (m, 1H), 2.16-2.02 (m, 3H), 1.92-1.82 (m, 2H), 1.69 (dt, J = 14.8, 7.3 Hz, 2H), 1.54-1.22 (m, 6H), 1.01 (t, J = 7.4 Hz, 3H); MS m/z 437.3 (M + 1). |

TABLE 5-continued
| Structure | Compound_ID | Mer IC$_{50}$ | Physical Data MS m/z (M + 1) or/and $^1$H NMR (400 MHz) |
|---|---|---|---|
| 4 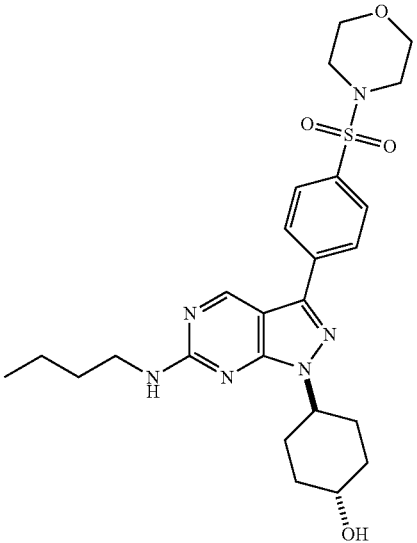 | UNC1062 A | ++++ | $^1$H NMR (400 MHz, CD$_3$OD). δ 9.20 (s, 1H), 8.26-8.20 (m, 2H), 7.95-7.89 (m, 2H), 4.75-4.64 (m, 1H), 3.79-3.68 (m, 1H), 3.73 (dd, J = 10.2, 5.7 Hz, 4H), 3.55 (t, J = 7.1 Hz, 2H), 3.08-2.97 (m, 4H), 2.36-2.01 (m, 6H), 1.76-1.65 (m, 2H), 1.62-1.42 (m, 4H), 1.02 (t, J = 7.4 Hz, 3H); MS m/z 515.0 (M + 1). |
| 5 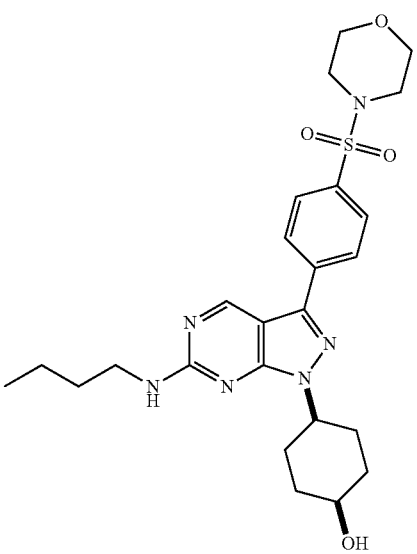 | UNC1063 A | ++++ | $^1$H NMR (400 MHz, CD$_3$OD). δ 9.19 (s, 1H), 8.28-8.20 (m, 2H), 7.96-7.88 (m, 2H), 4.78-4.69 (m, 1H), 4.08-4.02 (m, 1H), 3.78-3.67 (m, 4H), 3.54 (t, J = 7.1 Hz, 2H), 3.08-2.98 (m, 4H), 2.62-2.46 (m, 2H), 2.07-1.96 (m, 2H), 1.90-1.62 (m, 6H), 1.48 (dq, J = 14.5, 7.3 Hz, 2H), 1.01 (t, J = 7.4 Hz, 3H); MS m/z 515.2 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 6 | UNC1066 A | ++++ | $^1$H NMR (400 MHz, CD$_3$OD). δ 9.11 (s, 1H), 8.17 (d, J = 8.6 Hz, 2H), 8.00 (d, J = 8.6 Hz, 2H), 4.73-4.63 (m, 1H), 3.79-3.67 (m, 1H), 3.51 (t, J = 7.1 Hz, 2H), 2.30-2.01 (m, 7H), 1.69 (td, J = 14.7, 7.4 Hz, 2H), 1.61-1.42 (m, 4H), 1.01 (t, J = 7.4 Hz, 3H), 0.62-0.47 (m, 4H); MS m/z 485.0 (M + 1). |
| 7 | UNC1003 A | +++ | $^1$H NMR (400 MHz, CD$_3$OD). δ 9.06 (s, 1H), 7.83 (d, J = 8.9 Hz, 2H), 7.08 (d, J = 8.8 Hz, 2H), 4.68-4.58 (m, 1H), 3.89-3.81 (m, 4H), 3.76-3.67 (m, 1H), 3.55 (t, J = 7.1 Hz, 2H), 3.30-3.21 (m, 4H), 2.27-2.00 (m, 6H), 1.76-1.66 (m, 2H), 1.59-1.43 (m, 4H), 1.02 (t, J = 7.4 Hz, 3H); MS m/z 451.35 (M + 1). |
| 8 | UNC1170 A | ++++ | $^1$H NMR (400 MHz, CD$_3$OD). δ 9.22 (s, 1H), 8.07 (d, J = 8.4 Hz, 2H), 7.60 (d, J = 8.4 Hz, 2H), 4.26 (d, J = 6.8 Hz, 2H), 3.85-3.59 (m, 8H), 3.55 (t, J = 7.1 Hz, 2H), 3.13-3.02 (m, 1H), 2.15-2.01 (m, 3H), 1.87 (d, J = 12.1 Hz, 2H), 1.75-1.65 (m, 2H), 1.54-1.22 (m, 6H), 1.01 (t, J = 7.4 Hz, 3H); MS m/z 492.4 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 9 | 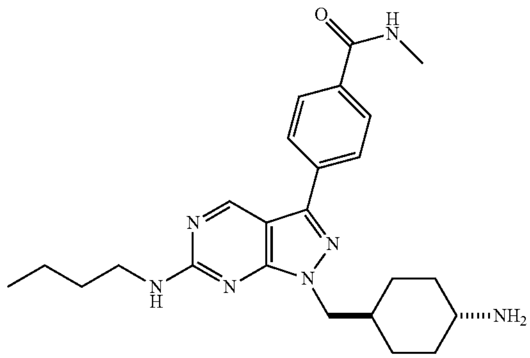 [SMILES: CCCCNc1ncc2c(-c3ccc(C(=O)NC)cc3)nn(C[C@H]3CC[C@H](N)CC3)c2n1] | UNC1179 A | ++++ | $^1$H NMR (400 MHz, CD$_3$OD) δ 9.13 (s, 1H), 8.05 (d, J = 8.5 Hz, 2H), 7.96 (d, J = 8.7 Hz, 2H), 4.25 (d, J = 6.8 Hz, 2H), 3.51 (t, J = 7.1 Hz, 2H), 3.12-3.02 (m, 1H), 2.95 (s, 3H), 2.15-2.01 (m, 3H), 1.85 (d, J = 12.3 Hz, 2H), 1.74-1.62 (m, 2H), 1.53-1.21 (m, 6H), 1.00 (t, J = 7.4 Hz, 3H); MS m/z 436.3 (M + 1). |
| 10 | 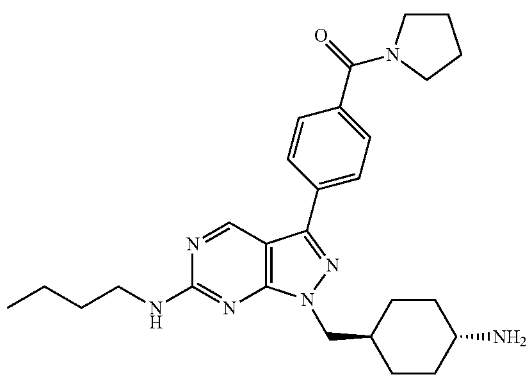 [SMILES: CCCCNc1ncc2c(-c3ccc(C(=O)N4CCCC4)cc3)nn(C[C@H]3CC[C@H](N)CC3)c2n1] | UNC1171 A | ++++ | $^1$H NMR (400 MHz, CD$_3$OD) δ 9.17 (s, 1H), 8.05 (d, J = 8.2 Hz, 2H), 7.68 (d, J = 8.2 Hz, 2H), 4.25 (d, J = 6.8 Hz, 2H), 3.62 (t, J = 8.0 Hz, 2H), 3.57-3.47 (m, 4H), 3.13-3.02 (m, 1H), 2.14-1.81 (m, 9H), 1.75-1.64 (m, 2H), 1.53-1.20 (m, 6H), 1.01 (t, J = 7.4 Hz, 3H); MS m/z 476.4 (M + 1). |
| 11 | 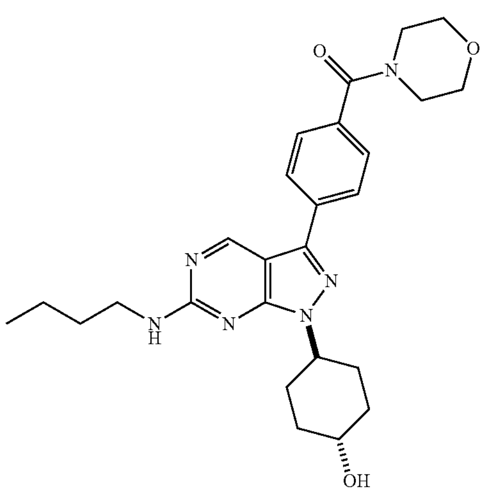 | UNC1180 A | ++++ | $^1$H NMR (400 MHz, CD$_3$OD) δ 9.13 (s, 1H), 8.05 (d, J = 8.0 Hz, 2H), 7.58 (d, J = 8.0 Hz, 2H), 4.72-4.60 (m, 1H), 3.86-3.44 (m, 11H), 2.29-1.99 (m, 6H), 1.76-1.64 (m, 2H), 1.61-1.41 (m, 4H), 1.02 (t, J = 7.3 Hz, 3H); MS m/z 479.3 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 12 | UNC1172 A | ++++ | $^1$H NMR (400 MHz, CD$_3$OD) δ 9.09 (s, 1H), 8.04 (d, J = 8.0 Hz, 2H), 7.56 (d, J = 6.5 Hz, 2H), 4.72-4.62 (m, 1H), 4.08-4.02 (m, 1H), 3.89-3.58 (m, 6H), 3.53 (t, J = 6.4 Hz, 2H), 3.58-3.43 (m, 2H), 2.60-2.45 (m, 2H), 2.07-1.95 (m, 2H), 1.89-1.61 (m, 6H), 1.52-1.39 (m, 2H), 0.99 (t, J = 7.3 Hz, 3H); MS m/z 479.3 (M + 1). |
| 13 | UNC1173 A | ++++ | $^1$H NMR (400 MHz, CD$_3$OD) δ 9.08 (s, 1H), 8.03 (d, J = 7.9 Hz, 2H), 7.65 (d, J = 7.9 Hz, 2H), 4.74-4.63 (m, 1H), 4.08-4.02 (m, 1H), 3.63 (t, J = 6.8 Hz, 2H), 3.56-3.47 (m, 4H), 2.61-2.45 (m, 2H), 2.07-1.89 (m, 6H), 1.88-1.62 (m, 6H), 1.53-1.40 (m, 2H), 0.99 (t, J = 7.3 Hz, 3H); MS m/z 463.3 (M + 1). |
| 14 | UNC1181 A | ++++ | $^1$H NMR (400 MHz, CD$_3$OD) δ 9.12 (s, 1H), 7.94 (d, J = 8.4 Hz, 2H), 7.80 (d, J = 8.4 Hz, 2H), 4.21 (d, J = 6.4 Hz, 2H), 3.97 (t, J = 6.9 Hz, 2H), 3.51 (t, J = 6.9 Hz, 2H), 3.13-3.01 (m, 1H), 2.63 (t, J = 8.0 Hz, 2H), 2.27-2.15 (m, 2H), 2.13-2.00 (m, 3H), 1.85 (d, J = 11.9 Hz, 2H), 1.74-1.62 (m, 2H), 1.54-1.20 (m, 6H), 1.00 (t, J = 7.3 Hz, 3H); MS m/z 462.3 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 15 | 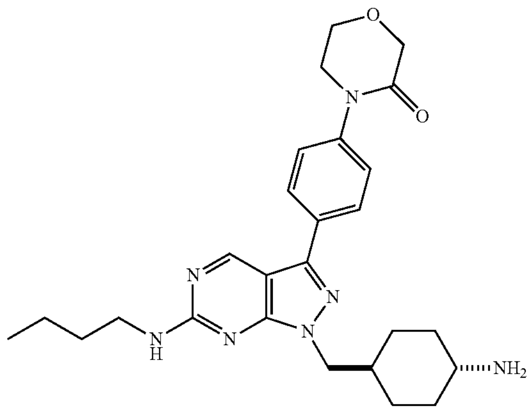 | UNC1182 A | ++++ | $^1$H NMR (400 MHz, CD$_3$OD) δ 9.16 (s, 1H), 8.05-7.99 (m, 2H), 7.60-7.54 (m, 2H), 4.32 (s, 2H), 4.23 (d, J = 6.8 Hz, 2H), 4.10-4.04 (m, 2H), 3.85 (dd, J = 5.8, 4.3 Hz, 2H), 3.53 (t, J = 7.1 Hz, 2H), 3.13-3.01 (m, 1H), 2.13-2.01 (m, 3H), 1.86 (d, J = 11.6 Hz, 2H), 1.74-1.65 (m, 2H), 1.53-1.21 (m, 6H), 1.01 (t, J = 7.4 Hz, 3H); MS m/z 478.3 (M + 1). |
| 16 | 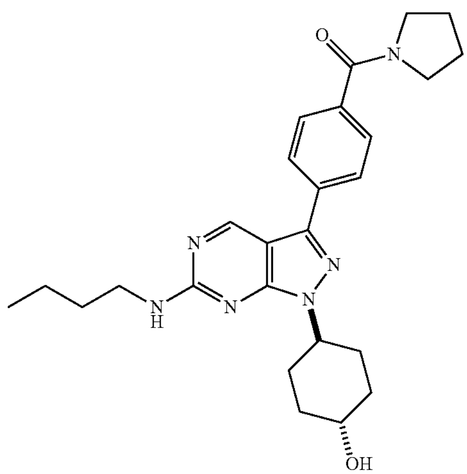 | UNC1183 A | ++++ | $^1$H NMR (400 MHz, CD$_3$OD) δ 9.11 (s, 1H), 8.03 (d, J = 8.1 Hz, 2H), 7.68 (d, J = 8.1 Hz, 2H), 4.72-4.61 (m, 1H), 3.78-3.68 (m, 1H), 3.63 (t, J = 6.8 Hz, 2H), 3.56-3.47 (m, 4H), 2.29-1.88 (m, 10H), 1.75-1.63 (m, 2H), 1.61-1.41 (m, 4H), 1.01 (t, J = 7.3 Hz, 3H); MS m/z 463.3 (M + 1). |
| 17 | 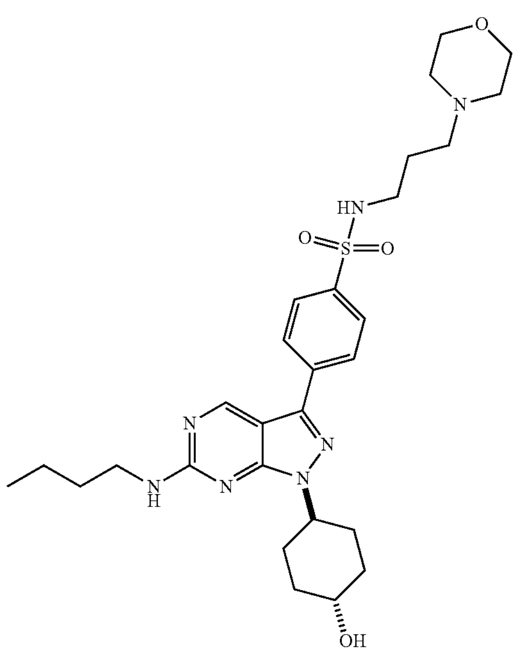 | UNC1095 A | ++++ | $^1$H NMR (400 MHz, CDCl$_3$), δ 9.43 (s, 1H), 8.86 (s, 1H), 7.98 (s, 4H), 4.66-4.63 (m, 1H), 4.02-3.98 (m, 4H), 3.87-3.82 (m, 1H), 3.59-3.53 (m, 4H), 3.25 (t, J = 6.97 Hz, 2H), 3.12-3.09 (m, 2H), 2.93-2.82 (m, 2H), 2.22-2.16 (m, 4H), 2.11-2.08 (m, 4H), 1.72 (td, J = 7.41, 14.83 Hz, 2H), 1.69-1.57 (m, 2H), 1.47 (dq, J = 7.29, 14.59 Hz, 2H), 1.00 (t, J = 7.35 Hz, 3H); MS m/z 572.35 (M + 1). |

TABLE 5-continued
| Structure | Compound_ID | Mer IC$_{50}$ | Physical Data MS m/z (M + 1) or/and $^1$H NMR (400 MHz) |
|---|---|---|---|
| 18 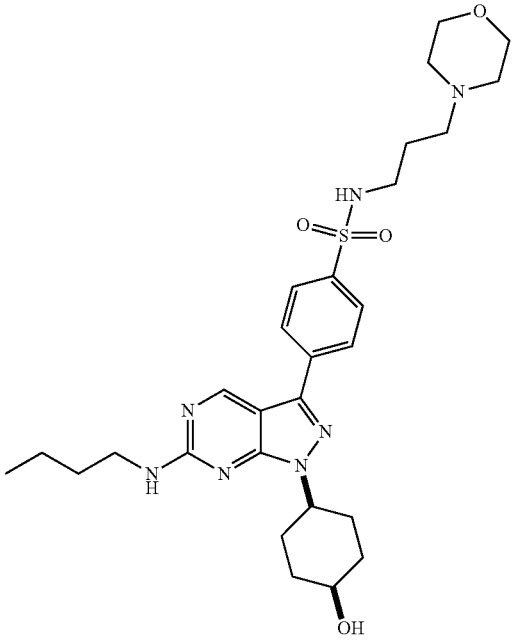 | UNC1096 A | ++++ | $^1$H NMR (400 MHz, CDCl$_3$) δ 9.41 (s, 1H), 8.94 (s, 1H), 7.96-7.91 (m, 4H), 6.86 (s, 1H), 4.70-4.64 (m, 1H), 4.17 (s, 1H), 3.98-3.87 (m, 4H), 3.54 (s, 4H), 3.22 (t, J = 6.67 Hz, 2H), 3.07 (s, 2H), 2.95-2.82 (m, 2H), 2.53-2.47 (m, 1H), 2.37-2.30 (m, 1H), 2.16-1.98 (m, 6H), 1.87-1.80 (m, 2H), 1.70 (dd, J = 7.38, 14.60 Hz, 2H), 1.46 (dq, J = 7.35, 14.60 Hz, 2H), 0.99 (t, J = 7.35 Hz, 3H); MS m/z 572.30 (M + 1). |
| 19 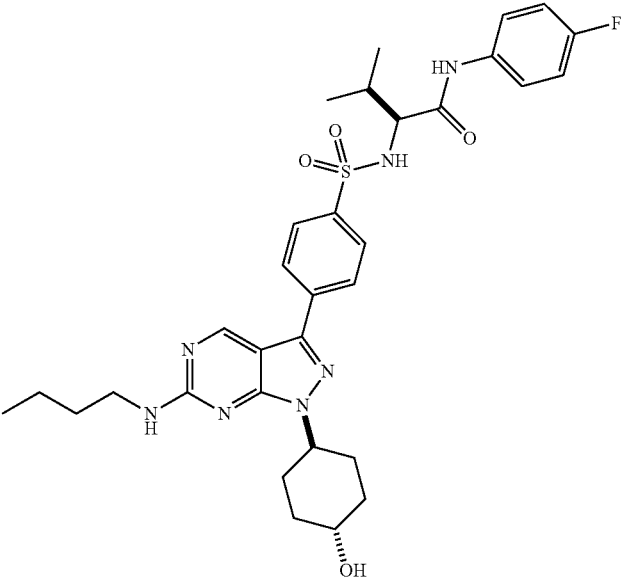 | UNC1120 A | ++++ | $^1$H NMR (400 MHz, CD$_3$OD) δ 8.80 (s, 1H), 7.91 (s, 4H), 7.18-7.13 (m, 2H), 6.73-6.66 (m, 2H), 4.66-4.59 (m, 1H), 3.75-3.68 (m, 1H), 3.58 (d, J = 7.92 Hz, 1H), 3.49 (t, J = 7.08 Hz, 2H), 2.22-2.12 (m, 4H), 2.02 (d, J = 11.21 Hz, 2H), 1.97-1.90 (m, 1H), 1.71-1.64 (m, 2H), 1.51-1.42 (m, 5H), 1.05-0.99 (m, 6H), 0.95 (d, J = 6.74 Hz, 3H); MS m/z 638.30 (M + 1). |

TABLE 5-continued

| Structure | Compound_ID | Mer IC$_{50}$ | Physical Data<br>MS m/z (M + 1) or/and<br>$^1$H NMR (400 MHz) |
|---|---|---|---|
| 20 | UNC1124A | +++ | $^1$H NMR (400 MHz, CD$_3$OD) δ 9.63 (s, 1H), 8.85 (s, 1H), 7.98-7.92 (m, 4H), 7.18-7.14 (m, 2H), 6.72-6.68 (m, 2H), 4.73-4.66 (m, 1H), 4.05 (s, 1H), 3.58 (d, J = 7.92 Hz, 1H), 3.51 (t, J = 7.07 Hz, 2H), 2.56-2.46 (m, 2H), 2.04-1.91 (m, 3H), 1.82-1.75 (m, 4H), 1.68 (dt, J = 7.37, 14.73 Hz, 2H), 1.48 (dq, J = 7.31, 14.44 Hz, 2H), 1.05 (d, J = 6.72 Hz, 3H), 1.01 (t, J = 7.35 Hz, 3H), 0.96 (d, J = 6.72 Hz, 3H); MS m/z 638.30 (M + 1). |
| 21 | UNC1125A | ++++ | $^1$H NMR (400 MHz, CD$_3$OD) δ 8.96 (s, 1H), 8.06 (d, J = 8.46 Hz, 2H), 7.89 (d, J = 8.54 Hz, 2H), 7.12-7.08 (m, 2H), 6.93-6.89 (m, 2H), 4.46-4.44 (m, 1H), 3.73-3.71 (m, 1H), 3.47 (t, J = 7.02 Hz, 2H), 3.12 (t, J = 7.38 Hz, 2H), 2.73 (t, J = 7.43 Hz, 2H), 2.22-2.02 (m, 7H), 1.69-1.62 (m, 2H), 1.54-1.43 (m, 4H), 0.99 (t, J = 7.36 Hz, 3H); MS m/z 567.20 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 22 | 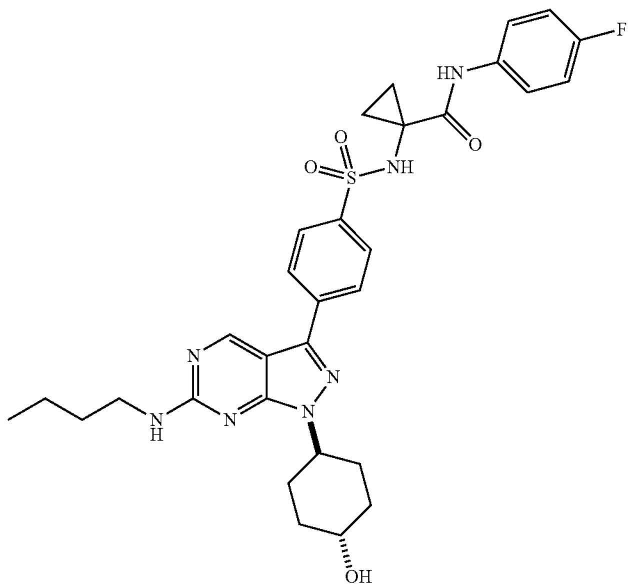 | UNC1137 A | +++ | $^1$H NMR (400 MHz, CD$_3$OD) δ 9.17 (s, 1H), 8.95 (s, 1H), 8.06 (d, J = 8.54 Hz, 2H), 7.96 (d, J = 8.33 Hz, 2H), 7.34-7.31 (m, 2H), 6.90-6.86 (m, 2H), 4.68-4.62 (m, 1H), 3.75-3.70 (m, 1H), 3.50 (t, J = 7.90 Hz, 2H), 2.24-2.13 (m, 4H), 2.06-2.03 (m, 2H), 1.71-1.64 (m, 2H), 1.58-1.38 (m, 6H), 1.10 (dd, J = 4.67, 7.89 Hz, 2H), 1.00 (t, J = 7.36 Hz, 3H); MS m/z 622.30 (M + 1). |
| 23 | 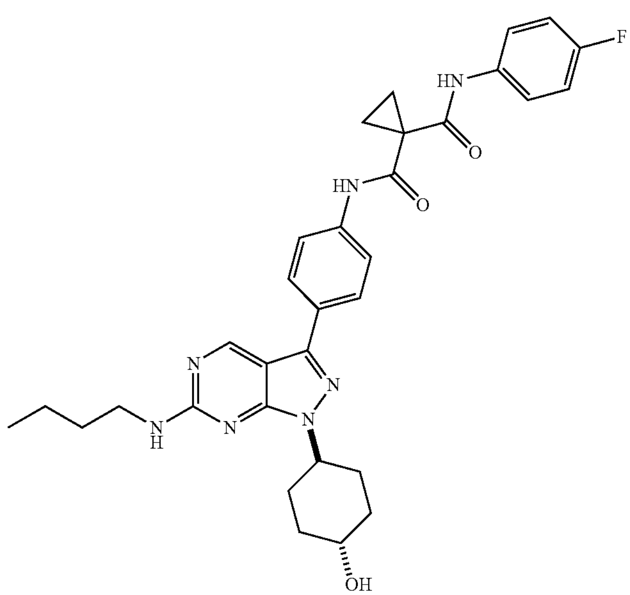 | UNC1138 A | +++ | $^1$H NMR (400 MHz, CDCl$_3$) δ 9.40 (s, 1H), 8.81 (s, 1H), 8.61 (s, 1H), 7.83 (d, J = 8.52 Hz, 2H), 7.67 (d, J = 8.52 Hz, 2H), 7.49-7.45 (m, 2H), 7.06 (t, J = 8.60 Hz, 2H), 4.62-4.60 (m, 1H), 3.84-3.82 (m, 1H), 3.54-3.49 (m, 2H), 2.27-2.17 (m, 4H), 2.06-2.00 (m, 2H), 1.74-1.66 (m, 8H), 1.58-1.55 (m, 2H), 1.46 (dd, J = 7.38, 14.93 Hz, 2H), 0.99 (t, J = 7.33 Hz, 3H); MS m/z 586.30 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 24 | 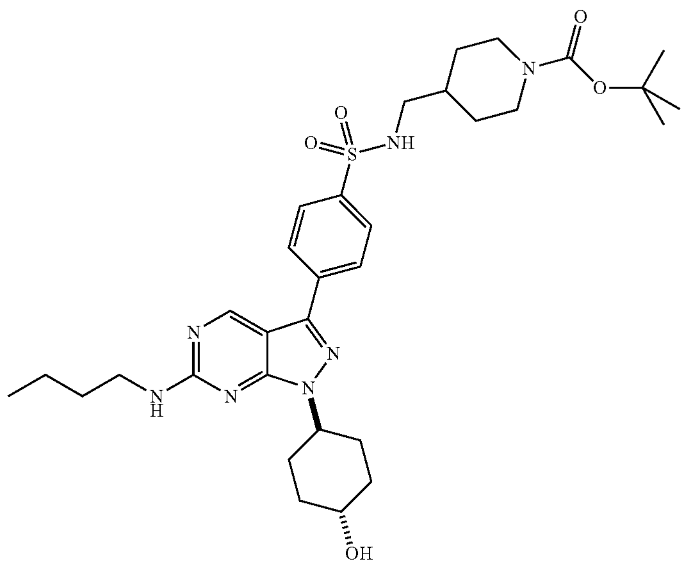 | UNC1174 A | ++++ | $^1$H NMR (400 MHz, CDCl$_3$ + CD$_3$OD) δ 8.78 (s, 1H), 7.90 (d, J = 8.44 Hz, 2H), 7.80 (d, J = 7.34 Hz, 2H), 4.46-4.43 (m, 1H), 3.91 (d, J = 12.95 Hz, 2H), 3.63-3.61 (m, 1H), 2.36 (t, J = 7.08 Hz, 2H), 3.22 (dt, J = 1.61, 3.24 Hz, 3H), 2.65 (d, J = 6.62 Hz, 2H), 2.54-2.51 (m, 2H), 2.08-2.00 (m, 4H), 1.93-1.90 (m, 2H), 1.58-1.46 (m, 4H), 1.31 (s, 12H), 0.97-0.91 (m, 2H), 0.89 (t, J = 7.35 Hz, 3H); MS m/z 642.40 (M + 1). |
| 25 | 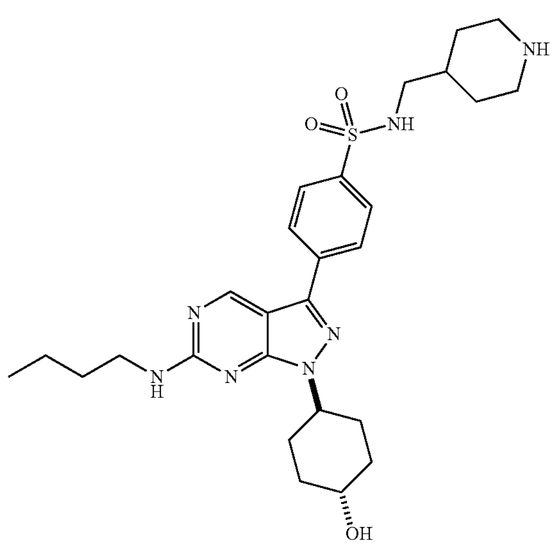 | UNC1175 A | ++++ | $^1$H NMR (400 MHz, CDCl$_3$ +CD$_3$OD) δ 8.25 (s, 1H), 7.23 (d, J = 8.45 Hz, 2H), 7.14 (d, J = 8.20 Hz, 2H), 3.85-3.80 (m, 1H), 2.96-2.91 (m, 1H), 2.72 (t, J = 7.15 Hz, 2H), 2.54-2.52 (m, 3H), 2.07-1.99 (m, 4H), 1.41-1.32 (m, 4H), 1.26-1.23 (m, 2H), 1.12 (d, J = 13.63 Hz, 2H), 0.98-0.94 (m, 1H), 0.91-0.84 (m, 2H), 0.79-0.75 (m, 2H), 0.67-0.56 (m, 4H), 0.17 (t, J = 7.35 Hz, 3H); MS m/z 542.30 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 26 | 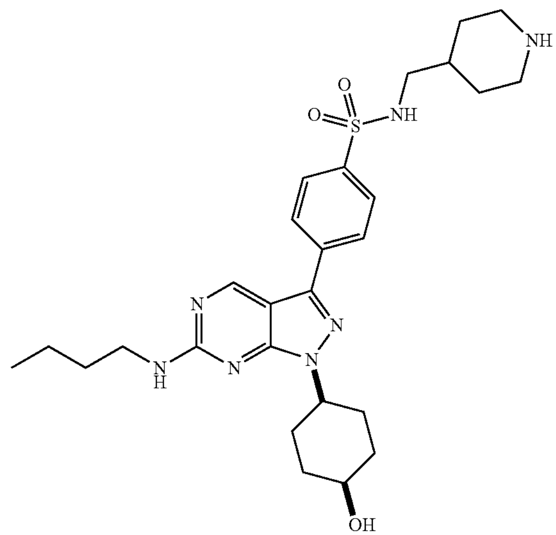 | UNC1176 A | ++++ | $^1$H NMR (400 MHz, CD$_3$OD) δ 9.20 (brs, 1H), 9.06 (s, 1H), 8.82 (brs, 1H), 7.96 (d, J = 7.39 Hz, 2H), 7.90 (d, J = 7.40 Hz, 2H), 4.68-4.63 (m, 1H), 4.15 (s, 1H), 3.54-3.49 (m, 2H), 3.41-3.39 (m, 2H), 2.85-2.83 (m, 5H), 2.47-2.44 (m, 2H), 2.01-1.97 (m, 2H), 1.75-1.65 (m, 8H), 1.51-1.39 (m, 4H), 0.95(t, J = 7.35 Hz, 3H); MS m/z 542.30 (M + 1). |
| 27 | 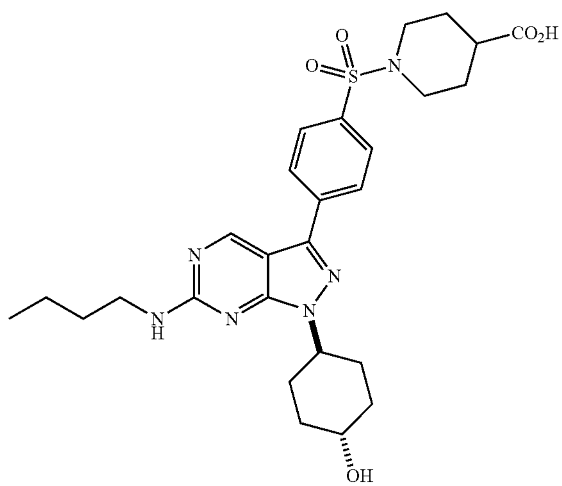 | UNC1177 A | ++++ | $^1$H NMR (400 MHz, CDCl$_3$ + CD$_3$OD) δ 8.81 (s, 1H), 7.95 (d, J = 8.33 Hz, 2H), 7.74 (d, J = 8.34 Hz, 2H), 4.54-4.52 (m, 1H), 3.69-3.64 (m, 1H), 3.57-3.54 (m, 2H), 3.39 (t, J = 7.07 Hz, 2H), 3.27-3.25 (m, 4H), 2.44 (t, J = 10.08 Hz, 2H), 2.17-2.04 (m, 4H), 1.96-1.88 (m, 4H), 1.77-1.68 (m, 2H), 1.59-1.52 (m, 2H), 1.49-1.43 (m, 2H), 1.40-1.31 (m, 2H), 0.89 (t, J = 7.35 Hz, 3H); MS m/z 557.20 (M + 1). |
| 28 | 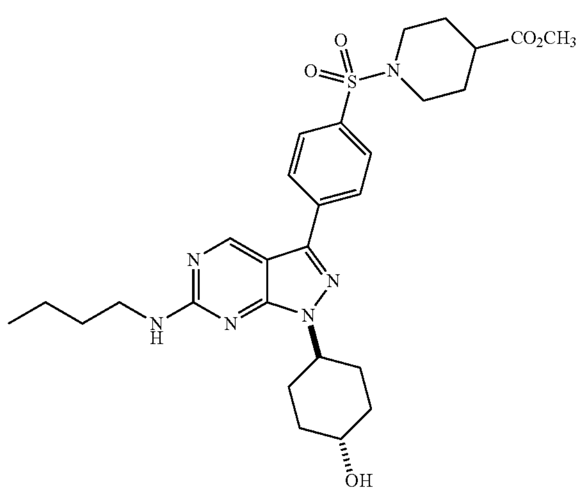 | UNC1178 A | ++++ | $^1$H NMR (400 MHz, CDCl$_3$ + CD$_3$OD) δ 8.90 (s, 1H), 8.18 (d, J = 8.18 Hz, 2H), 7.86 (d, J = 7.74 Hz, 2H), 4.68-4.62 (m, 1H), 3.88-3.81 (m, 1H), 3.68-3.66 (m, 5H), 3.55-3.49 (m, 2H), 2.58-2.55 (m, 2H), 2.31-2.20 (m, 6H), 2.09-2.06 (m, 2H), 1.99 (dd, J = 3.38, 14.62 Hz, 2H), 1.89-1.79 (m, 2H), 1.71-1.56 (m, 4H), 1.46 (dt, J = 7.30, 14.60 Hz, 2H), 1.00 (t, J = 7.35 Hz, 3H); MS m/z 571.20 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 29 | 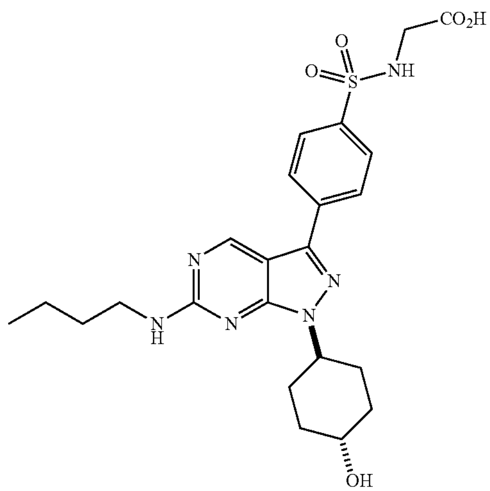 | UNC1184 A | ++++ | $^1$H NMR (400 MHz, DMSO-d$^6$) δ 12.68 (s, 1H), 9.18 (s, 1H), 8.15 (d, J = 8.17 Hz, 2H), 7.88 (d, J = 8.22 Hz, 2H), 7.62 (s, 1H), 4.55-4.49 (m, 1H), 3.62 (d, J = 6.01 Hz, 2H), 3.58-3.51 (m, 2H), 3.17 (s, 1H), 2.07-1.97 (m, 6H), 1.57 (s, 2H), 1.40-1.38 (m, 4H), 0.93 (t, J = 6.50 Hz, 3H); MS m/z 503.30 (M + 1). |
| 30 | 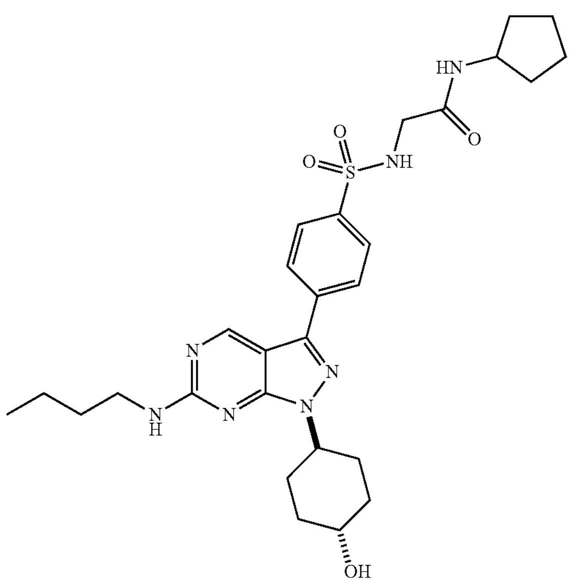 | UNC1185 A | ++++ | $^1$H NMR (400 MHz, CDCl$_3$) δ 8.79 (s, 1H), 7.91 (d, J = 8.34 Hz, 2H), 7.80 (d, J = 8.36 Hz, 2H), 4.52-4.46 (m, 1H), 3.91 (dd, J = 6.77, 14.84 Hz, 1H), 3.64-3.59 (m, 1H), 3.36 (s, 4H), 3.20 (s, 2H), 2.10-2.00 (m, 4H), 1.91 (d, J = 10.90 Hz, 2H), 1.74 (dt, J = 6.07, 12.39 Hz, 2H), 1.56-1.50 (m, 4H), 1.46-1.39 (m, 4H), 1.33 (dt, J = 7.19, 14.73 Hz, 2H), 1.26-1.20 (m, 2H), 0.85 (t, J = 7.35 Hz, 3H); MS m/z 570.30 (M + 1). |

TABLE 5-continued
| | Structure | Compound_ID | Mer IC$_{50}$ | Physical Data MS m/z (M + 1) or/and $^1$H NMR (400 MHz) |
|---|---|---|---|---|
| 31 | 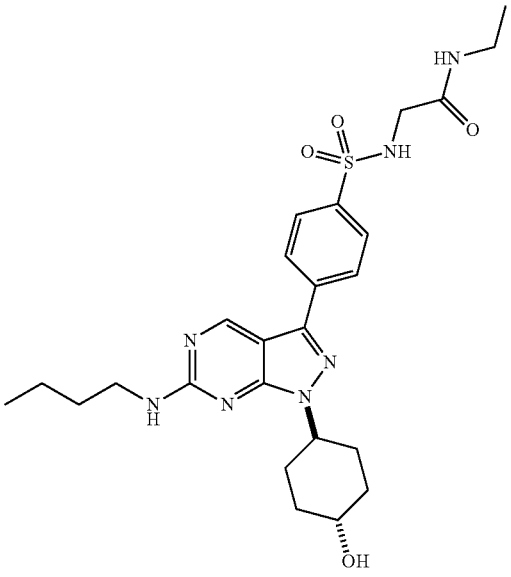 | UNC1186A | ++++ | $^1$H NMR (400 MHz, CDCl$_3$ + CD$_3$OD) δ 8.76 (s, 1H), 7.91 (d, J = 8.12 Hz, 2H), 7.80 (d, J = 8.12 Hz, 2H), 4.51-4.46 (m, 1H), 3.63-3.58 (m, 2H), 3.20 (s, 4H), 3.08 (dd, J = 7.09, 14.30 Hz, 2H), 2.06-2.01 (m, 4H), 1.90 (d, J = 11.10 Hz, 2H), 1.51-1.49 (m, 2H), 1.41-1.29 (m, 4H), 0.96 (t, J = 7.12 Hz, 3H), 0.84 (t, J = 7.24 Hz, 3H); MS m/z 530.30 (M + 1). |
| 32 | 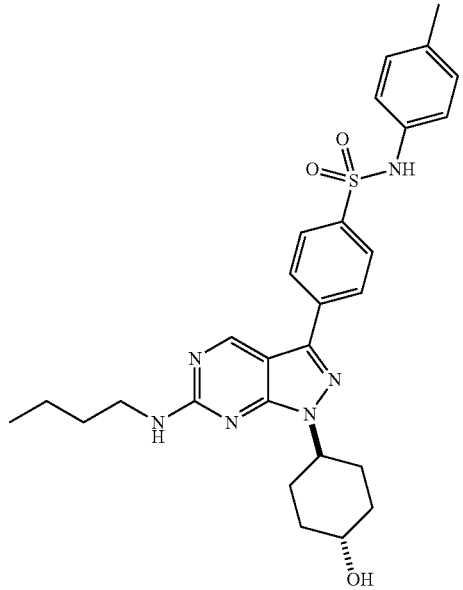 | UNC1187A | ++++ | $^1$H NMR (400 MHz, CDCl$_3$) δ 8.72 (s, 1H), 7.81-7.79 (m, 2H), 7.69-7.66 (m, 2H), 6.68-6.63 (m, 4H), 4.49-4.44 (m, 1H), 3.64-3.57 (m, 1H), 3.39-3.32 (m, 2H), 3.21 (dt, J = 1.62, 3.25 Hz, 3H), 2.10 (s, 3H), 2.04-1.98 (m, 4H), 1.90-1.87 (m, 2H), 1.51 (dt, J = 7.36, 14.80 Hz, 2H), 1.43-1.37 (m, 2H), 1.31 (dd, J = 7.43, 14.98 Hz, 2H), 0.84 (t, J = 7.35 Hz, 3H)); MS m/z 535.30 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 33 | UNC1188 A | ++++ | $^1$H NMR (400 MHz, CDCl$_3$) δ 9.06 (s, 1H), 7.84 (d, J = 8.55 Hz, 2H), 7.61 (d, J = 8.57 Hz, 2H), 4.66-4.60 (m, 1H), 3.76-3.70 (m, 1H), 3.55-3.48 (m, 6H), 2.30- 2.10 (m, 4H), 2.10-1.92 (m, 6H), 1.77-1.63 (m, 2H), 1.61-1.40 (m, 4H), 1.02 (t, J = 7.32 Hz, 3H); MS m/z 478.30 (M + 1). |
| 34 | UNC1189 A | +++ | $^1$H NMR (400 MHz, CDCl$_3$ + CD$_3$OD) δ 8.84 (s, 1H), 7.71 (d, J = 8.53 Hz, 2H), 7.51 (d, J = 8.48 Hz, 2H), 4.59-4.51 (m, 1H), 4.02 (s, 1H), 3.32 (s, 1H), 2.88-2.82 (m, 9H), 2.51-2.33 (m, 2H), 1.99-1.90 (m, 6H), 1.77-1.58 (m, 6H), 1.43-1.35 (m, 2H), 0.91 (t, J = 7.3 Hz, 3H); MS m/z 478.30 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 35 | 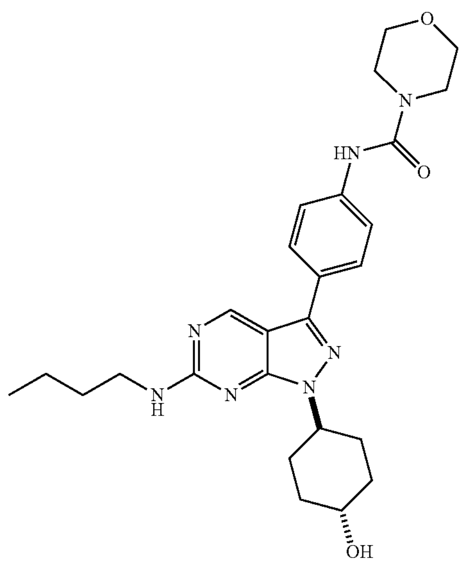 | UNC1190 A | ++++ | $^1$H NMR (400 MHz, CDCl$_3$ + CD$_3$OD) δ 8.81 (s, 1H), 7.71 (d, J = 8.41 Hz, 2H), 7.49 (d, J = 8.29 Hz, 2H), 4.54 (s, 1H), 3.75-3.67 (m, 4H), 2.24 (s, 9H), 2.15-2.12 (m, 4H), 2.00-1.98 (m, 2H), 1.70-1.58 (m, 2H), 1.54-1.49 (m, 2H), 1.46-1.38 (m, 2H), 0.94 (t, J = 7.35 Hz, 3H); MS m/z 494.30 (M + 1). |
| 36 | 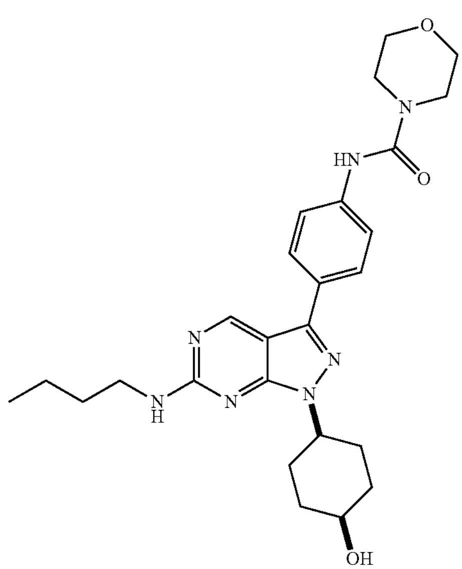 | UNC1191 A | +++ | $^1$H NMR (400 MHz, CDCl$_3$ + CD$_3$OD) δ 8.80 (s, 1H), 7.73 (d, J = 8.53 Hz, 2H), 7.48 (d, J = 8.53 Hz, 2H), 4.62-4.54 (m, 1H), 4.07 (s, 1H), 3.76-3.68 (m, 4H), 3.50-3.45 (m, 5H), 2.54-2.38 (m, 2H), 1.98 (d, J = 12.93 Hz, 2H), 1.90-1.70 (m, 8H), 1.64 (dt, J = 7.31, 14.58, 2H), 1.41 (dd, J = 7.41, 14.83 Hz, 2H), 0.94 (t, J = 7.32 Hz, 3H); MS m/z 494.30 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 37 | 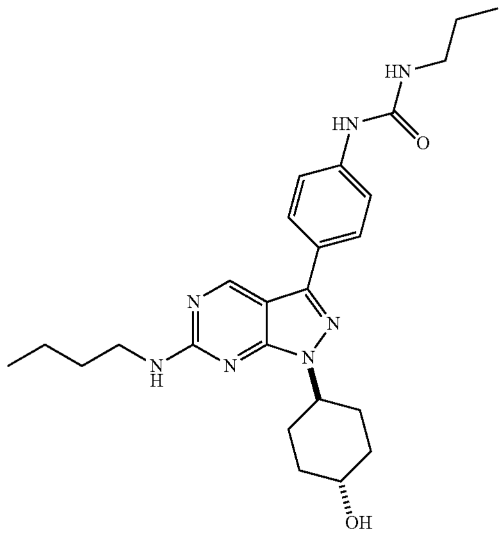 | UNC1192 A | ++++ | $^1$H NMR (400 MHz, CDCl$_3$ + CD$_3$OD) δ 8.81 (s, 1H), 7.67 (d, J = 8.51 Hz, 2H), 7.47 (d, J = 8.49 Hz, 2H), 4.57-4.51 (m, 1H), 3.76-3.71 (m, 1H), 3.48 (t, J = 7.15 Hz, 2H), 3.16 (t, J = 7.02 Hz, 2H), 2.76 (s, 4H), 2.19-2.13 (m, 4H), 2.01-1.98 (m, 2H), 1.71-1.59 (m, 2H), 1.56-1.39 (m, 6H), 0.93 (dt, J = 7.35, 14.83 Hz, 6H); MS m/z 466.30 (M + 1). |
| 38 | 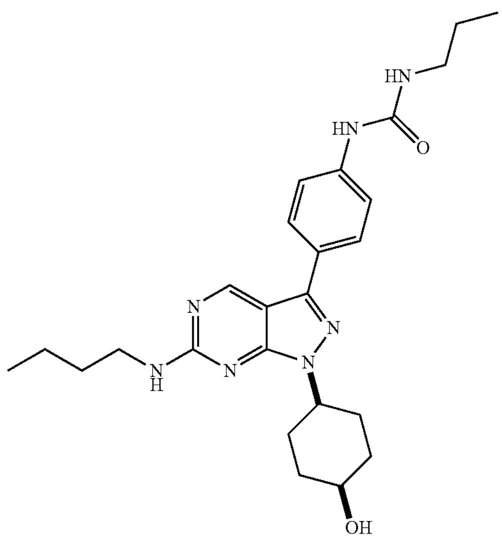 | UNC1193 A | +++ | $^1$H NMR (400 MHz, CDCl$_3$ + CD$_3$OD) δ 8.72 (s, 1H), 7.61 (d, J = 8.48 Hz, 2H), 7.41 (d, J = 8.51 Hz, 2H), 4.58-4.52 (m, 1H), 4.07 (s, 1H), 3.46 (t, J = 7.15 Hz, 2H), 3.17 (t, J = 7.02 Hz, 2H), 2.53-2.39 (m, 2H), 2.00 (s, 4H), 1.83-1.58 (m, 6H), 1.54-1.51 (m, 2H), 1.43-1.37 (m, 2H), 0.92 (dt, J = 7.39, 9.95 Hz, 6H); MS m/z 466.30 (M + 1). |
| 39 | 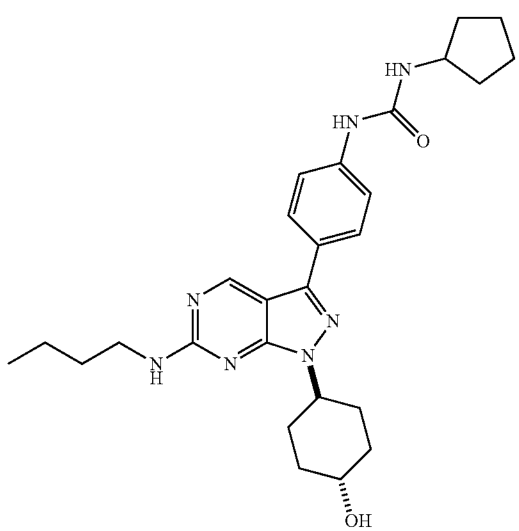 | UNC1222 A | ++++ | $^1$H NMR (400 MHz, CDCl$_3$) δ 9.46 (s, 1H), 8.60 (s, 1H), 7.67 (d, J = 8.57 Hz, 2H), 7.47 (d, J = 8.60 Hz, 2H), 6.76 (s, 1H), 4.59-4.53 (m, 1H), 4.15-4.07 (m, 1H), 3.84-3.75 (m, 1H), 3.53-3.48 (m, 2H), 2.17-2.12 (m, 4H), 2.03-1.98 (m, 4H), 1.77-1.49 (m, 8H), 1.48-1.39 (m, 4H), 0.97 (t, J = 7.35 Hz, 3H); MS m/z 492.30 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 40 | UNC1223A | ++++ | $^1$H NMR (400 MHz, CDCl$_3$) δ 8.72 (s, 1H), 7.74 (d, J = 8.52 Hz, 2H), 7.41 (d, J = 8.62 Hz, 2H), 6.43 (s, 1H), 4.68 (d, J = 6.47 Hz, 1H), 4.62-4.56 (m, 1H), 4.16-4.07 (m, 2H), 3.54-3.49 (m, 2H), 2.57-2.42 (m, 2H), 2.04-1.96 (m, 4H), 1.84-1.71 (m, 5H), 1.70-1.57 (m, 5H), 1.49-1.36 (m, 4H), 0.96 (t, J = 7.35 Hz, 3H); MS m/z 492.30 (M + 1). |
| 41 | UNC1142A | ++++ | $^1$H NMR (400 MHz, CDCl$_3$) δ 8.92 (s, 1H), 8.08-8.00 (m, 2H), 7.89-7.81 (m, 2H), 5.32 (bs, 1H), 4.72-4.56 (m, 1H), 3.91-3.76 (m, 1H), 3.52 (dd, J = 12.9, 6.9 Hz, 2H), 3.09 (bs, 4H), 2.53 (bs, 4H), 2.41 (q, J = 7.2 Hz, 2H), 2.30-2.14 (m, 4H), 2.13-1.99 (m, 2H), 1.66 (dt, J = 14.7, 7.3 Hz, 2H), 1.59-1.52 (m, 3H), 1.47 (dq, J = 14.4, 7.3 Hz, 2H), 1.03 (t, J = 7.1 Hz, 3H), 1.00 (t, J = 7.3 Hz, 3H); MS m/z 542.3 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 42 | UNC1143 A | ++++ | $^1$H NMR (400 MHz, CDCl$_3$) δ 8.94 (s, 1H), 8.03 (d, J = 8.3 Hz, 2H), 7.88 (d, J = 8.2 Hz, 2H), 5.32 (bs, 1H), 4.73-4.56 (m, 1H), 3.84 (bs, 1H), 3.52 (dd, J = 13.0, 6.6 Hz, 2H), 3.42 (bs, 4H), 2.70 (d, J = 19.2 Hz, 4H), 2.55 (bs, 2H), 2.31-2.14 (m, 4H), 2.07 (d, J = 11.0 Hz, 2H), 1.86 (s, 2H), 1.70-1.63 (m, 2H), 1.63-1.55 (m, 3H), 1.51-1.39 (m, 2H), 1.13-0.94 (m, 6H); MS m/z 556.4 (M + 1). |
| 43 | UNC1144 A | ++++ | $^1$H NMR (400 MHz, CDCl$_3$) δ 8.94 (s, 1H), 8.05 (d, J = 8.3 Hz, 2H), 7.85 (d, J = 8.3 Hz, 2H), 5.32 (s, 1H), 4.72-4.57 (m, 1H), 3.96-3.77 (m, 3H), 3.52 (dd, J = 13.0, 6.8 Hz, 2H), 2.45 (s, 4H), 2.29 (t, J = 11.0 Hz, 3H), 2.19 (dd, J = 18.1, 7.2 Hz, 4H), 2.07 (d, J = 11.0 Hz, 2H), 1.85 (d, J = 11.2 Hz, 2H), 1.67 (dt, J = 22.3, 7.5 Hz, 5H), 1.57 (d, J = 7.3 Hz, 6H), 1.51-1.37 (m, 4H), 0.99 (t, J = 7.3 Hz, 3H); MS m/z 596.4 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 44 | UNC1145 A | ++++ | $^1$H NMR (400 MHz, CDCl$_3$) δ 8.94 (s, 1H), 8.05 (d, J = 8.2 Hz, 2H), 7.85 (d, J = 8.2 Hz, 2H), 5.32 (bs, 1H), 4.76-4.57 (m, 1H), 3.85 (d, J = 10.8 Hz, 3H), 3.68 (bs, 4H), 3.52 (dd, J = 12.8, 6.6 Hz, 2H), 2.48 (s, 4H), 2.34 (t, J = 10.8 Hz, 2H), 2.20 (t, J = 11.9 Hz, 4H), 2.08 (s, 3H), 1.88 (d, J = 11.5 Hz, 2H), 1.65 (dd, J = 14.2, 7.8 Hz, 4H), 1.55 (d, J = 13.6 Hz, 3H), 1.47 (dd, J = 14.8, 7.4 Hz, 2H), 0.99 (t, J = 7.3 Hz, 3H); MS m/z 598.4 (M + 1). |
| 45 | UNC1146 A | ++++ | $^1$H NMR (400 MHz, CDCl$_3$) δ 8.93 (s, 1H), 8.07-7.97 (m, 2H), 7.96-7.89 (m, 2H), 5.40 (bs, 1H), 4.73-4.58 (m, 1H), 3.91-3.76 (m, 1H), 3.52 (dd, J = 12.9, 6.9 Hz, 2H), 3.01 (s, 3H), 2.30-2.14 (m, 4H), 2.07 (d, J = 10.8 Hz, 2H), 1.68-1.44 (m, 7H), 1.38 (d, J = 4.8 Hz, 9H), 0.99 (t, J = 7.3 Hz, 3H); MS m/z 515.3 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 46 | UNC1147 A | ++++ | $^1$H NMR (400 MHz, CDCl$_3$) δ 8.94 (s, 1H), 8.07 (d, J = 8.4 Hz, 2H), 7.88 (d, J = 8.3 Hz, 2H), 5.34 (bs, 1H), 4.73-4.59 (m, 1H), 3.90-3.76 (m, 1H), 3.52 (dd, J = 13.0, 6.8 Hz, 2H), 2.75 (s, 6H), 2.29-2.15 (m, 4H), 2.13-2.02 (m, 2H), 1.66 (dt, J = 14.9, 7.3 Hz, 2H), 1.59-1.52 (t, J = 10.2 Hz, 3H), 1.47 (dd, J = 15.0, 7.4 Hz, 2H), 1.00 (t, J = 7.3 Hz, 3H); MS m/z 473.3 (M + 1). |
| 47 | UNC1148 A | ++++ | $^1$H NMR (400 MHz, CDCl$_3$) δ 8.96 (s, 1H), 8.11 (d, J = 8.3 Hz, 2H), 7.95 (d, J = 8.2 Hz, 2H), 5.33 (s, 1H), 4.75-4.57 (m, 1H), 3.92-3.74 (m, 5H), 3.53 (dd, J = 13.1, 6.7 Hz, 2H), 2.32-2.16 (m, 4H), 2.15-2.03 (m, 4H), 1.66 (dt, J = 14.8, 7.2 Hz, 2H), 1.55-1.50 (m, 3H), 1.45 (dd, J = 14.6, 7.3 Hz, 2H), 1.00 (t, J = 7.3 Hz, 3H); MS m/z 485.3 (M + 1). |
| 48 | UNC1149 A | ++++ | $^1$H NMR (400 MHz, CDCl$_3$) δ 8.87 (s, 1H), 7.64-7.55 (m, 2H), 7.02 (t, J = 8.7 Hz, 1H), 5.38 (bs, 1H), 4.69-4.50 (m, 1H), 3.94-3.88 (m, 4H), 3.88-3.77 (m, 1H), 3.51 (dd, J = 13.0, 6.9 Hz, 2H), 3.20-3.10 (m, 4H), 2.29-2.12 (m, 4H), 2.10-1.98 (d, J = 11.8 Hz, 2H), 1.68-1.41 (m, 7H), 0.99 (t, J = 7.3 Hz, 3H); MS m/z 469.3 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 49 | 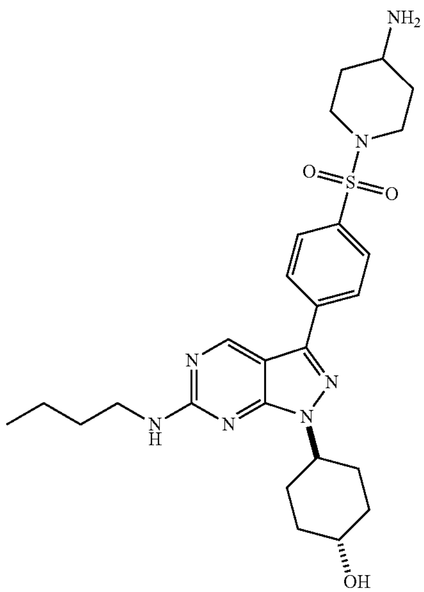 | UNC1150A | ++++ | $^1$H NMR (400 MHz, CD$_3$OD) δ 8.89 (s, 1H), 8.10-8.03 (m, 2H), 7.86-7.79 (m, 2H), 4.68-4.54 (m, 1H), 3.84-3.75 (m, 2H), 3.75-3.67 (m, 1H), 3.47 (t, J = 7.1 Hz, 2H), 2.75-2.64 (m, 1H), 2.40 (dt, J = 12.0, 6.0 Hz, 2H), 2.24-2.08 (m, 4H), 2.03 (d, J = 11.4 Hz, 2H), 1.92 (d, J = 10.3 Hz, 2H), 1.68-1.60 (m, 2H), 1.58-1.48 (m, 4H), 1.44 (dd, J = 15.0, 7.5 Hz, 2H), 0.96 (t, J = 7.4 Hz, 3H); MS m/z 528.3 (M + 1). |
| 50 | 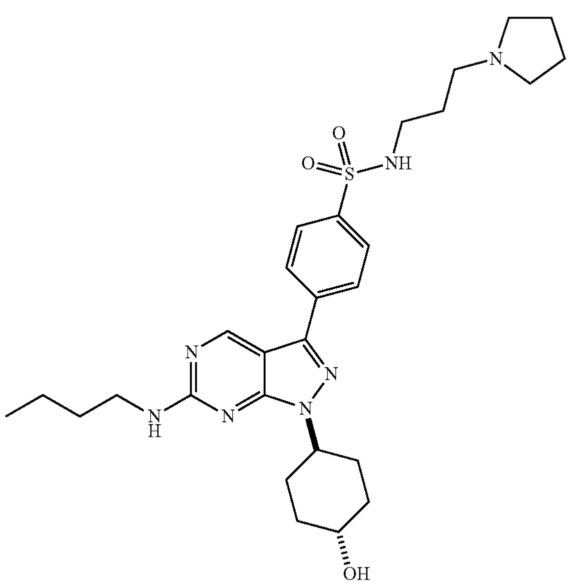 | UNC1224A | ++++ | $^1$H NMR (400 MHz, CDCl$_3$) δ 10.75 (s, 1H), 9.07 (s, 1H), 7.99 (d, J = 8.4 Hz, 2H), 7.94 (d, J = 8.4 Hz, 2H), 4.67-4.57 (m, 1H), 3.88-3.75 (m, 3H), 3.55-3.52 (m, 2H), 3.30 (dd, J = 13.3, 6.7 Hz, 2H), 3.06 (t, J = 6.0 Hz, 2H), 2.92-2.82 (m, 2H), 2.24-1.98 (m, 12H), 1.74-1.64 (m, 2H), 1.62-1.52 (m, 2H), 1.49-1.39 (m, 2H), 0.97 (t, J = 7.4 Hz, 3H); MS m/z 556.40 (M + 1) |

TABLE 5-continued

| Structure | Compound_ID | Mer IC$_{50}$ | Physical Data MS m/z (M + 1) or/and $^1$H NMR (400 MHz) |
|---|---|---|---|
| 51 | UNC1225A | ++++ | $^1$H NMR (400 MHz, CDCl$_3$) δ 9.03 (s, 1H), 8.00 (d, J = 8.2 Hz, 2H), 7.94 (d, J = 8.1 Hz, 2H), 4.64-4.57 (m, 1H), 3.89 (dd, J = 11.3, 4.1 Hz, 2H), 3.79-3.74 (m, 1H), 3.53-3.47 (m, 4H), 3.41 (d, J = 1.6 Hz, 1H), 3.38-3.28 (m, 2H), 3.23 (t, J = 7.2 Hz, 2H), 2.19-2.11 (m, 4H), 2.07-1.99 (m, 2H), 1.71-1.62 (m, 2H), 1.60-1.48 (m, 4H), 1.42 (dt, J = 14.5, 7.4 Hz, 5H), 1.29-1.17 (m, 3H), 0.96 (t, J = 7.3 Hz, 3H)); MS m/z 614.30 (M + 1). |
| 52 | UNC1226A | ++++ | $^1$H NMR (400 MHz, CDCl$_3$) δ 8.93 (s, 1H), 7.99 (d, J = 8.3 Hz, 2H), 7.89 (d, J = 8.3 Hz, 2H), 4.65-4.51 (m, 1H), 3.83-3.67 (m, 1H), 3.49-3.43 (m, 4H), 3.37-3.33 (m, 3H), 2.61-2.55 (m, 1H), 2.19-2.10 (m, 4H), 2.02-1.99 (m, 2H), 1.63 (dt, J = 14.5, 7.1 Hz, 2H), 1.57-3.47 (m, 2H), 1.46-1.37 (m, 2H), 0.94 (t, J = 7.3 Hz, 3H), 0.69 (q, J = 6.6 Hz, 2H), 0.51-0.38 (m, 2H); MS m/z 542.20 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 53 | UNC1265 A | ++++ | $^1$H NMR (400 MHz, CDCl$_3$ + CD$_3$OD) δ 9.15 (s, 1H), 8.16-8.10 (m, 2H), 8.00-7.93 (m, 2H), 4.70-4.60 (m, 1H), 3.92-3.81 (m, 1H), 3.76-3.65 (m, 1H), 3.55-3.45 (m, 4H), 3.42-3.34 (m, 1H), 3.19-3.11 (m, 2H), 3.06 (td, J = 13.0, 2.6 Hz, 2H), 2.85 (d, J = 15.8 Hz, 3H), 2.49-2.27 (m, 3H), 2.25-2.00 (m, 8H), 1.77-1.62 (m, 4H), 1.59-1.50 (m, 2H), 1.45 (dt, J = 14.4, 7.4 Hz, 2H), 0.99 (t, J = 7.4 Hz, 3H); MS m/z 613.40 (M + 1). |
| 54 | UNC1266 A | ++++ | $^1$H NMR (400 MHz, CDCl$_3$ + CD$_3$OD) δ 9.19 (s, 1H), 8.19-8.12 (m, 2H), 8.00-7.94 (m, 2H), 4.75-4.68 (m, 1H), 4.06-4.00 (m, 1H), 3.92-3.82 (m, 1H), 3.57-3.46 (m, 4H), 3.43-3.35 (m, 1H), 3.27-3.12 (m, 3H), 3.07 (td, J = 13.0, 2.5 Hz, 2H), 2.85 (d, J = 15.3 Hz, 3H), 2.56-2.43 (m, 2H), 2.38 (t, J = 6.7 Hz, 2H), 2.12 (d, J = 14.9 Hz, 2H), 2.03-1.94 (m, 3H), 1.86-1.74 (m, 3H), 1.72-1.63 (m, 3H), 1.46 (dq, J = 14.5, 7.3 Hz, 2H), 0.99 (t, J = 7.4 Hz, 3H); MS m/z 613.40 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 55 | 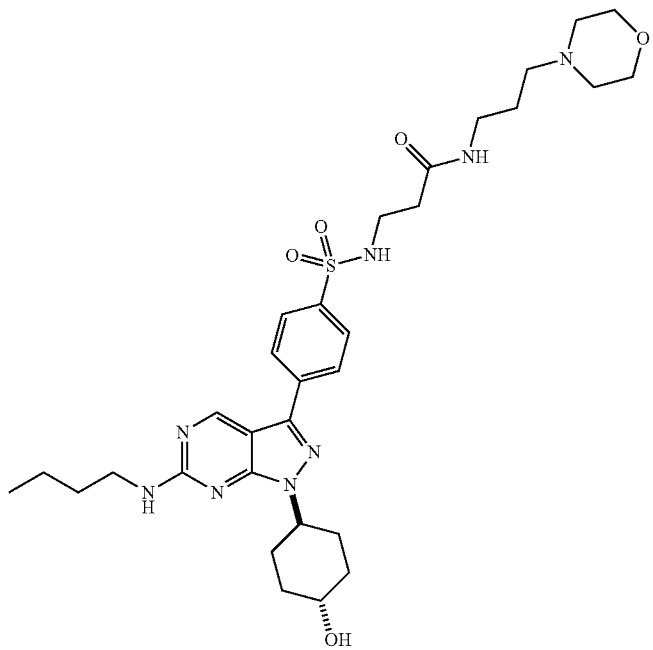 | UNC1267 A | ++++ | $^1$H NMR (400 MHz, CDCl$_3$ + CD$_3$OD) δ 9.00 (s, 1H), 7.97 (d, J = 8.3 Hz, 2H), 7.92 (d, J = 7.91 Hz, 2H), 5.10-4.99 (m, 1H), 4.63-4.52 (m, 1H), 4.03-3.92 (m, 2H), 3.88-3.82 (m, 2H), 3.77-3.67 (m, 1H), 3.50-3.46 (m, 4H), 3.31-3.27 (m, 3H), 3.18-3.08 (m, 4H), 3.00-2.89 (m, 2H), 2.40-2.33 (m, 2H), 2.30-2.27 (m, 1H), 2.17-2.08 (m, 3H), 2.05-1.89 (m, 4H), 1.69-1.58 (m, 2H), 1.57-1.44 (m, 2H), 1.44-1.37 (m, 2H), 0.93 (t, J = 7.3 Hz, 3H); MS m/z 643.40 (M + 1). |
| 56 | 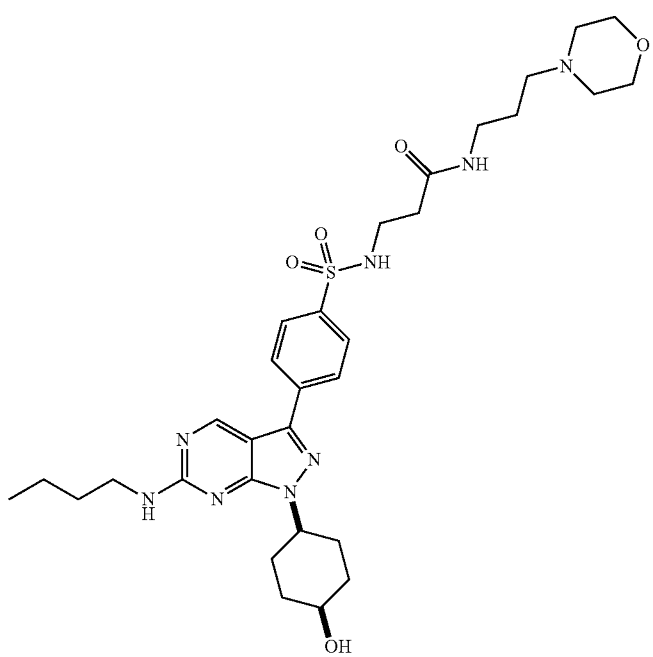 | UNC1268 A | ++++ | $^1$H NMR (400 MHz, CDCl$_3$ + CD$_3$OD) δ 9.00 (s, 1H), 7.98 (dd, J = 8.4, 4.2 Hz, 2H), 7.90 (dd, J = 11.6, 3.4 Hz, 2H), 4.67-4.54 (m, 1H), 4.06-3.76 (m, 5H), 3.58 (s, 3H), 3.52-3.42 (m, 4H), 3.31-3.23 (m, 2H), 3.17-3.06 (m, 4H), 3.01-2.89 (m, 2H), 2.49-2.39 (m, 2H), 2.37-2.30 (m, 2H), 1.99-1.86 (m, 4H), 1.81-1.69 (m, 3H), 1.66-1.59 (m, 2H), 1.39 (dt, J = 14.9, 7.4 Hz, 2H), 0.91 (t, J = 7.4 Hz, 3H); MS m/z 643.40 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 57 | UNC1269 A | ++++ | $^1$H NMR (400 MHz, CDCl$_3$ + CD$_3$OD) δ 8.95 (s, 1H), 8.06 (d, J = 8.2 Hz, 2H), 7.92 (d, J = 8.1 Hz, 2H), 4.64-4.57 (m, 1H), 3.74-3.67 (m, 1H), 3.57-3.53 (m, 1H), 3.46 (t, J = 7.1 Hz, 2H), 3.13 (t, J = 6.7 Hz, 2H), 2.33 (t, J = 6.8 Hz, 2H), 2.26-1.98 (m, 7H), 1.78 (d, J = 10.9 Hz, 2H), 1.71-1.60 (m, 4H), 1.54 (dd, J = 19.6, 9.4 Hz, 2H), 1.46-1.41 (m, 2H), 1.33-1.21 (m, 3H), 1.17-1.07 (m, 3H), 0.96 (t, J = 7.3 Hz, 3H); MS m/z 598.40 (M + 1). |
| 58 | UNC1270 A | +++ | $^1$H NMR (400 MHz, CDCl$_3$ + CD$_3$OD) δ 8.91 (s, 1H), 8.05-8.00 (m, 2H), 7.98-7.92 (m, 2H), 5.72-5.64 (m, 1H), 5.33 (d, J = 7.5 Hz, 1H), 4.78-4.59 (m, 1H), 4.14 (dd, J = 7.6, 4.3 Hz, 1H), 3.93-3.81 (m, 1H), 3.75-3.64 (m, 1H), 3.56-3.46 (m, 2H), 3.22 (dd, J = 11.6, 6.2 Hz, 2H), 2.58-2.49 (m, 1H), 2.41-2.34 (m, 2H), 2.09-1.92 (m, 4H), 1.91-1.80 (m, 4H), 1.72-1.56 (m, 6H), 1.46 (dt, J = 14.7, 7.3 Hz, 3H), 1.31 (dt, J = 15.5, 3.4 Hz, 2H), 1.17-1.04 (m, 3H), 1.01-0.94 (m, 3H); MS m/z 598.40 (M + 1). |

TABLE 5-continued

| | Structure | Compound_ID | Mer IC₅₀ | Physical Data MS m/z (M + 1) or/and ¹H NMR (400 MHz) |
|---|---|---|---|---|
| 59 | 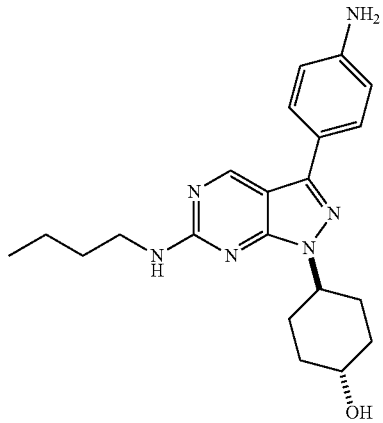 | UNC1234 A | ++++ | ¹H NMR (400 MHz, CDCl₃ + CD₃OD) δ 8.80 (s, 1H), 7.59 (d, J = 8.4 Hz, 2H), 6.76 (d, J = 8.4 Hz, 2H), 4.55-4.49 (m, 1H), 3.74-3.69 (m, 1H), 3.48 (t, J = 7.1 Hz, 2H), 2.20-2.04 (m, 4H), 1.98 (d, J = 9.2 Hz, 2H), 1.72-1.58 (m, 2H), 1.56-1.45 (m, 2H), 1.42-1.36 (m, 2H), 0.94 (t, J = 7.3 Hz, 3H); MS m/z 381.30 (M + 1). |
| 60 | 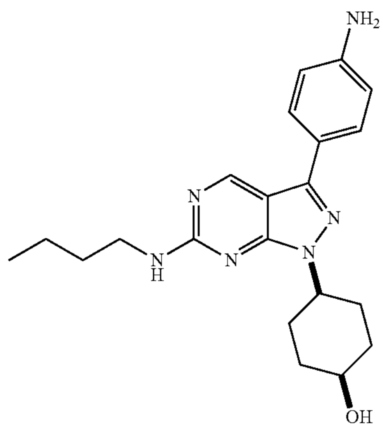 | UNC1235 A | +++ | ¹H NMR (400 MHz, CDCl₃ + CD₃OD) δ 8.80 (s, 1H), 7.61 (d, J = 8.3 Hz, 2H), 6.79 (d, J = 8.4 Hz, 2H), 4.58-4.52 (m, 1H), 4.05 (s, 1H), 3.47 (t, J = 7.2 Hz, 2H), 2.52-2.34 (m, 2H), 1.97 (d, J = 12.0 Hz, 2H), 1.79-1.69 (m, 4H), 1.63 (dd, J = 14.8, 7.6 Hz, 2H), 1.40 (dq, J = 14.5, 7.3 Hz, 2H), 0.93 (t, J = 7.3 Hz, 3H); MS m/z 381.30 (M + 1). |
| 61 | 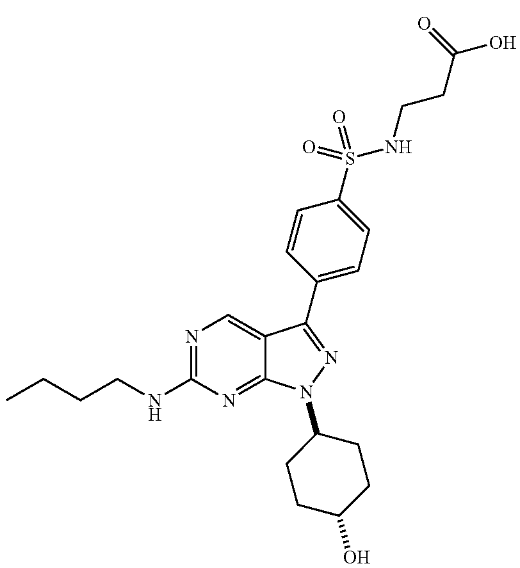 | UNC1236 A | ++++ | ¹H NMR (400 MHz, CDCl₃ + CD₃OD) δ 8.85 (s, 1H), 7.94 (d, J = 8.4 Hz, 2H), 7.87 (d, J = 8.2 Hz, 2H), 4.60-4.50 (m, 1H), 3.73-3.64 (m, 1H), 3.42 (t, J = 7.1 Hz, 2H), 3.30-3.27 (m, 3H), 2.43 (t, J = 6.1 Hz, 2H), 2.14-1.94 (m, 7H), 1.61-1.55 (m, 2H), 1.51-1.44 (m, 2H), 1.42-1.33 (m, 3H), 0.90 (t, J = 7.2 Hz, 3H); MS m/z 517.30 (M + 1). |

TABLE 5-continued
| | Structure | Compound_ID | Mer IC$_{50}$ | Physical Data MS m/z (M + 1) or/and $^1$H NMR (400 MHz) |
|---|---|---|---|---|
| 62 | 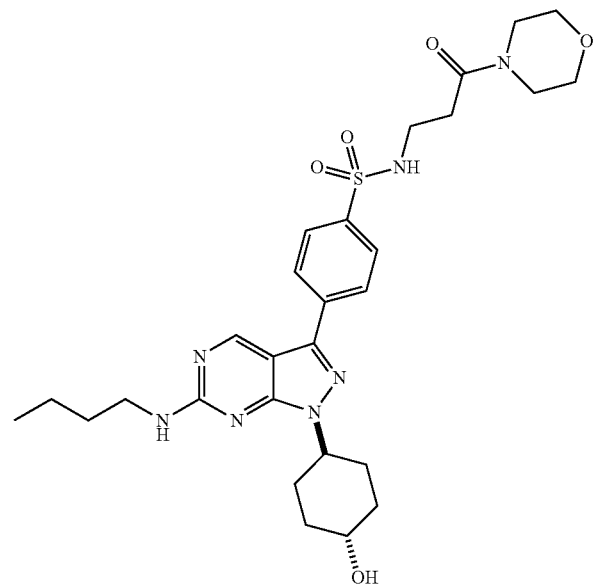 | UNC1281 A | ++++ | $^1$H NMR (400 MHz, CD$_3$OD) δ 9.14 (s, 1H), 8.16 (d, J = 8.4 Hz, 2H), 7.99 (d, J = 8.4 Hz, 2H), 4.71-4.65 (m, 1H), 3.75-3.68 (m, 1H), 3.62 (dd, J = 9.5, 4.8 Hz, 3H), 3.53 (t, J = 6.3 Hz, 3H), 3.48-3.44 (m, 2H), 3.20 (t, J = 6.6 Hz, 2H), 2.65 (s, 1H), 2.58 (t, J = 6.6 Hz, 2H), 2.29-2.03 (m, 7H), 1.75-1.63 (m, 3H), 1.59-1.51 (m, 2H), 1.51-1.44 (m, 2H), 1.02 (t, J = 7.4 Hz, 3H); MS m/z 586.35 (M + 1). |
| 63 | 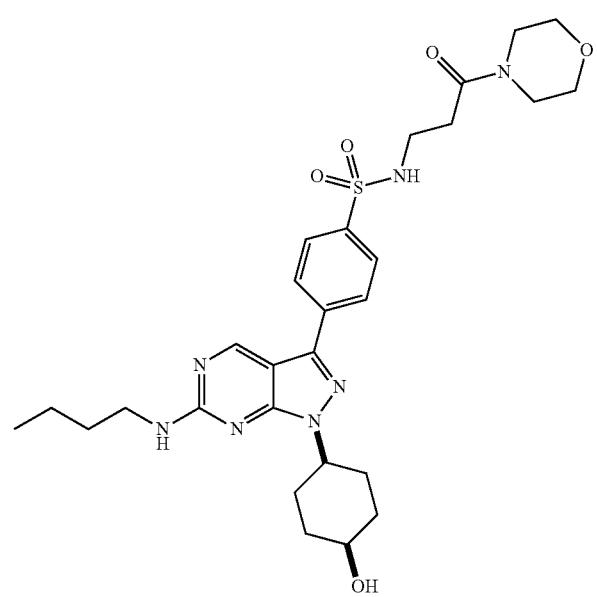 | UNC1282 A | +++ | $^1$H NMR (400 MHz, CDCl$_3$) δ 8.86 (s, 1H), 8.03-7.92 (m, 4H), 5.72 (t, J = 6.6 Hz, 1H), 4.70-4.60 (m, 1H), 4.13 (s, 1H), 3.68-3.60 (m, 4H), 3.60-3.46 (m, 5H), 3.39-3.32 (m, 2H), 3.26 (dd, J = 11.3, 6.2 Hz, 2H), 2.59-2.45 (m, 4H), 2.06-1.95 (m, 2H), 1.89-1.74 (m, 4H), 1.72-1.62 (m, 2H), 1.50-1.39 (m, 2H), 0.97 (t, J = 7.4 Hz, 3H); MS m/z 586.40 (M + 1). |

TABLE 5-continued
| | Structure | Compound_ID | Mer IC$_{50}$ | Physical Data MS m/z (M + 1) or/and $^1$H NMR (400 MHz) |
|---|---|---|---|---|
| 64 | 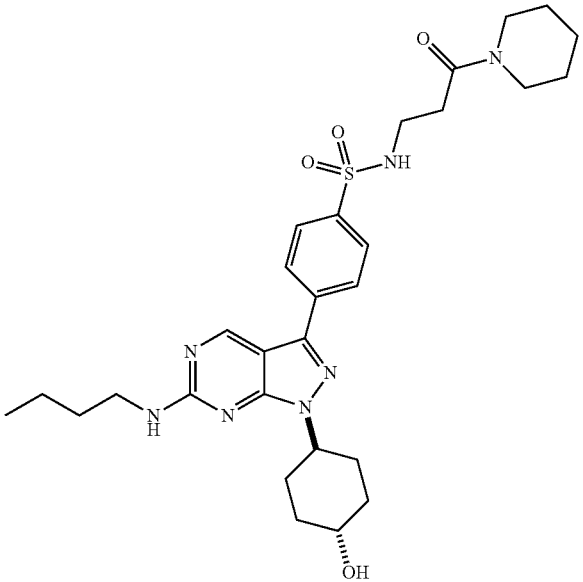 | UNC1283 A | ++++ | $^1$H NMR (400 MHz, CD$_3$OD) δ 9.03 (s, 1H), 8.15-8.10 (m, 2H), 7.98-7.93 (m, 2H), 4.69-4.60 (m, 2H), 3.74-3.66 (m, 1H), 3.49-3.43 (m, 4H), 3.39-3.34 (m, 2H), 3.17 (t, J = 6.8 Hz, 2H), 2.52 (t, J = 6.8 Hz, 2H), 2.28-2.18 (m, 2H), 2.16-2.08 (m, 2H), 2.06-1.98 (m, 2H), 1.70-1.55 (m, 5H), 1.55-1.41 (m, 8H), 0.99 (t, J = 7.4 Hz, 3H); MS m/z 584.35 (M + 1) |
| 65 | 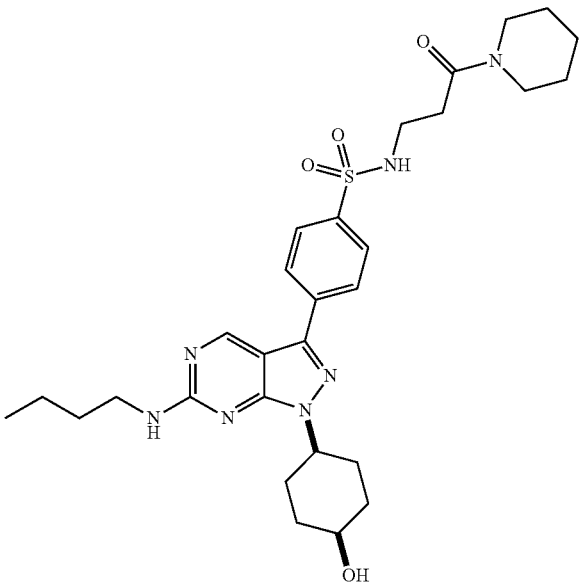 | UNC1284 A | ++++ | $^1$H NMR (400 MHz, CDCl$_3$ + CD$_3$OD) δ 8.89 (d, J = 1.6 Hz, 1H), 8.02-7.96 (m, 2H), 7.95-7.89 (m, 2H), 4.71-4.57 (m, 1H), 4.08-4.02 (m, 1H), 3.83-3.73 (m, 1H), 3.50-3.40 (m, 4H), 3.35 (dt, J = 3.3, 1.6 Hz, 1H), 3.30-3.23 (m, 2H), 3.16 (t, J = 5.6 Hz, 2H), 2.54-2.40 (m, 2H), 2.28-2.25 (m, 1H), 2.14-2.04 (m, 1H), 2.04-1.87 (m, 3H), 1.86-1.68 (m, 2H), 1.66-1.53 (m, 4H), 1.53-1.36 (m, 6H), 0.93 (td, J = 7.3, 0.7 Hz, 3H); MS m/z 584.30 (M + 1). |

TABLE 5-continued
| | Structure | Compound_ID | Mer IC$_{50}$ | Physical Data MS m/z (M + 1) or/and $^1$H NMR (400 MHz) |
|---|---|---|---|---|
| 66 | 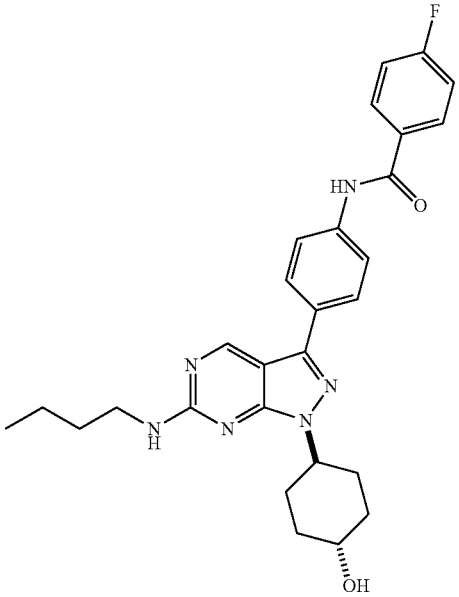 | UNC1279 A | +++ | $^1$H NMR (400 MHz, CDCl$_3$ + CD$_3$OD) δ 8.87 (s, 1H), 7.94-7.90 (m, 2H), 7.85-7.76 (m, 4H), 7.17-7.09 (m, 2H), 4.62-4.51 (m, 1H), 3.79-3.71 (m, 1H), 3.48 (t, J = 7.2 Hz, 2H), 2.18 (dt, J = 22.5, 7.1 Hz, 4H), 2.06-1.96 (m, 2H), 1.69-1.59 (m, 2H), 1.59-1.47 (m, 2H), 1.47-1.37 (m, 2H), 0.95 (t, J = 7.4 Hz, 3H); MS m/z 503.30 (M + 1). |
| 67 | 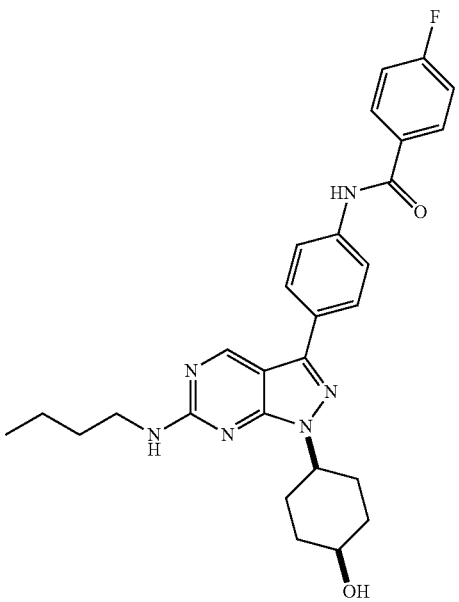 | UNC1280 A | +++ | $^1$H NMR (400 MHz, CDCl$_3$ + CD$_3$OD) δ 8.86 (s, 1H), 7.96-7.88 (m, 2H), 7.84-7.72 (m, 4H), 7.17-7.08 (m, 2H), 4.67-4.53 (m, 1H), 4.10-4.02 (m, 1H), 3.46 (td, J = 7.2, 3.3 Hz, 2H), 2.48 (dt, J = 20.7, 6.7 Hz, 2H), 2.09-1.94 (m, 3H), 1.85-1.67 (m, 3H), 1.63 (dt, J = 14.8, 7.4 Hz, 2H), 1.39 (dq, J = 14.8, 7.4 Hz, 3H), 0.93 (t, J = 7.3, 1.3 Hz, 3H); MS m/z 503.30 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 68 | 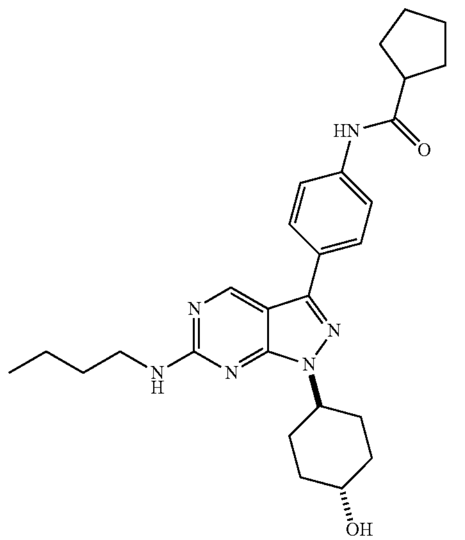 | UNC1309 A | +++ | $^1$H NMR (400 MHz, CDCl$_3$ + CD$_3$OD) δ 8.83 (s, 1H), 7.81 (d, J = 8.6 Hz, 2H), 7.66 (d, J = 8.5 Hz, 2H), 7.30 (s, 1H), 4.66-4.54 (m, 1H), 3.88-3.77 (m, 1H), 3.51 (dd, J = 12.6, 7.0 Hz, 2H), 2.71 (p, J = 8.1 Hz, 1H), 2.26-2.13 (m, 4H), 2.09-2.00 (m, 2H), 2.00-1.88 (m, 4H), 1.85-1.73 (m, 2H), 1.71-1.59 (m, 4H), 1.60-1.50 (m, 2H), 1.49-1.40 (m, 2H), 0.98 (t, J = 7.3 Hz, 3H); $^{13}$C NMR (100 MHz, CDCl$_3$ + CD$_3$OD) δ 174.86, 155.50, 139.09, 127.47, 119.83, 77.30, 76.98, 76.66, 69.65, 55.03, 47.14, 41.28, 34.39, 31.47, 30.51, 29.47, 26.00, 20.09, 13.80; MS m/z 477.30 (M + 1). |
| 69 | 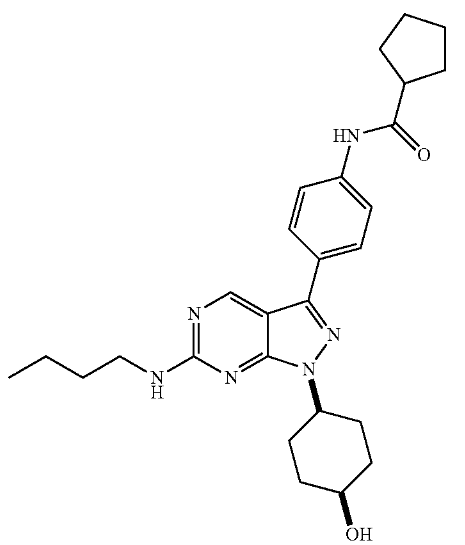 | UNC1310 A | +++ | $^1$H NMR (400 MHz, CDCl$_3$ + CD$_3$OD) δ 8.83 (s, 1H), 7.81 (d, J = 8.6 Hz, 2H), 7.63 (d, J = 8.5 Hz, 2H), 7.39 (s, 1H), 4.65-4.54 (m, 1H), 4.15-4.05 (m, 1H), 3.49 (dd, J = 12.3, 6.9 Hz, 2H), 2.74-2.65 (m, 1H), 2.58-2.44 (m, 2H), 2.03-1.87 (m, 6H), 1.87-3.70 (m, 6H), 1.70-1.54 (m, 4H), 1.44 (dt, J = 14.8, 7.3 Hz, 2H), 0.96 (t, J = 7.3 Hz, 3H); $^{13}$C NMR (100 MHz, CDCl$_3$ + CD$_3$OD) δ 174.66, 155.11, 143.63, 138.71, 128.18, 127.44, 119.84, 77.30, 76.99, 76.67, 65.25, 54.89, 46.90, 41.33, 31.84, 31.41, 30.52, 26.01, 25.71, 20.09, 13.81; MS m/z 477.35 (M + 1). |
| 70 | 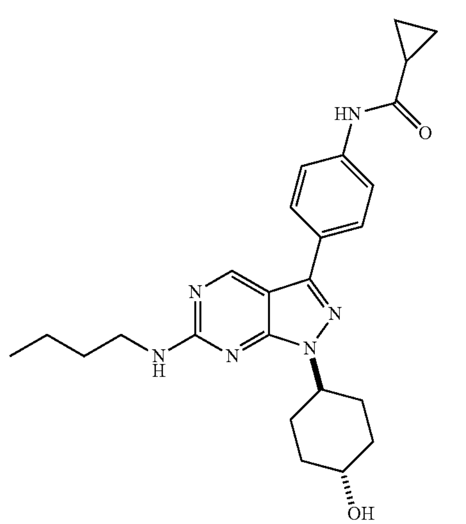 | UNC1311 A | ++++ | $^1$H NMR (400 MHz, CDCl$_3$) δ 8.77 (s, 1H), 7.79 (d, J = 8.6 Hz, 2H), 7.66 (d, J = 8.5 Hz, 2H), 7.56 (s, 1H), 4.65-4.55 (m, 1H), 3.87-3.77 (m, 1H), 3.56-3.49 (m, 2H), 2.27-2.13 (m, 4H), 2.09-2.01 (m, 2H), 1.68 (dt, J = 14.8, 7.4 Hz, 2H), 1.63-1.51 (m, 3H), 1.50-1.40 (m, 2H), 1.15-1.10 (m, 2H), 0.99 (t, J = 7.3 Hz, 3H), 0.92-0.85 (m, 2H); $^{13}$C NMR (100 MHz, CDCl$_3$) δ 155.11, 139.12, 127.51, 119.83, 110.22, 106.35, 77.29, 77.18, 76.97, 76.66, 69.55, 55.07, 41.36, 34.29, 31.05, 29.39, 20.07, 16.06, 13.76, 8 20; MS m/z 449.30 (M + 1). |

TABLE 5-continued
| | Structure | Compound_ID | Mer IC$_{50}$ | Physical Data MS m/z (M + 1) or/and $^1$H NMR (400 MHz) |
|---|---|---|---|---|
| 71 | 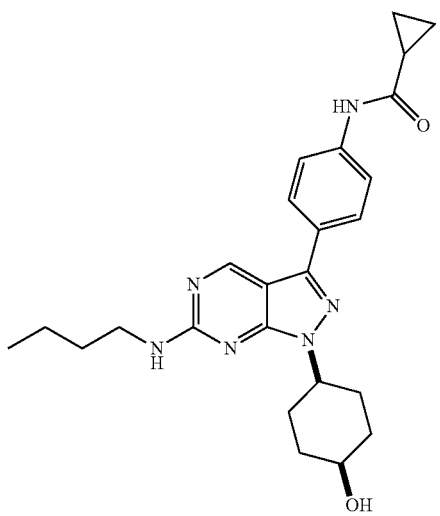 | UNC1312 A | ++++ | $^1$H NMR (400 MHz, CDCl$_3$) δ 8.74 (s, 1H), 7.77 (d, J = 8.6 Hz, 2H), 7.70 (s, 1H), 7.64 (d, J = 8.5 Hz, 2H), 4.66-4.57 (m, 1H), 4.16-4.11 (m, 1H), 3.50 (d, J = 7.2 Hz, 2H), 2.59-2.46 (m, 2H), 2.06-1.97 (m, 2H), 1.87-1.73 (m, 4H), 1.72-1.64 (m, 2H), 1.59-1.51 (m, 1H), 1.51-1.39 (m, 2H), 1.14-1.08 (m, 2H), 0.98 (t, J = 7.4 Hz, 3H), 0.91-0.85 (m, 2H); MS m/z 449.30 (M + 1). |
| 72 | 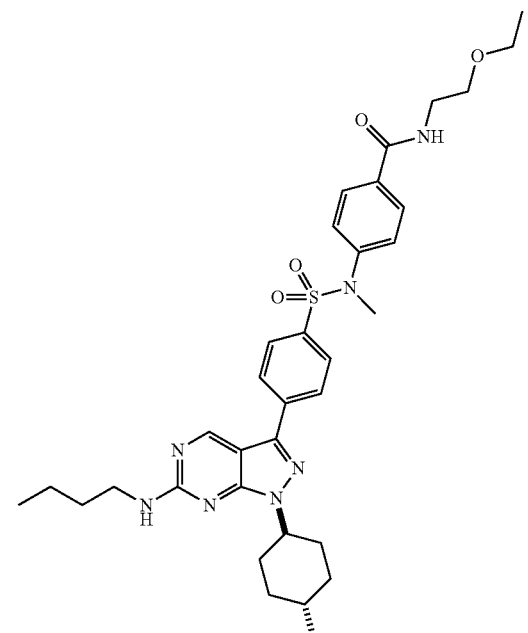 | UNC1313 A | ++++ | $^1$H NMR (400 MHz, CDCl$_3$) δ 8.87 (d, J = 6.3 Hz, 1H), 7.91 (d, J = 8.4 Hz, 2H), 7.69 (d, J = 8.6 Hz, 2H), 7.55 (d, J = 8.4 Hz, 2H), 7.15 (d, J = 8.6 Hz, 2H), 4.59-4.51 (m, 1H), 3.73-3.65 (m, 1H), 3.53 (s, 3H), 3.48-3.47 (t, m, 4H), 3.45-3.40 (m, 2H), 3.15 (s, 3H), 2.16-2.02 (m, 4H), 2.02-1.93 (m, 2H), 1.63-1.54 (m, 2H), 1.53-1.42 (m, 2H), 1.42-1.33 (m, 2H), 1.15 (t, J = 7.0 Hz, 3H), 0.91 (t, J = 7.3 Hz, 3H); MS m/z 650.35 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 73 | 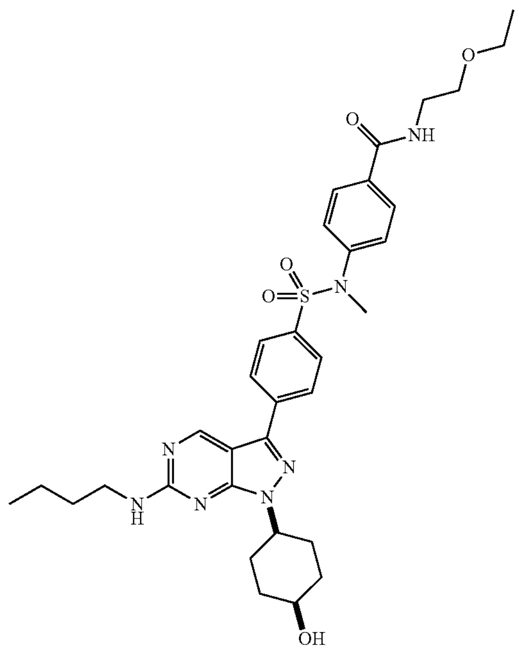 | UNC1314 A | ++++ | $^1$H NMR (400 MHz, CDCl$_3$) δ 9.02 (s, 1H), 8.09 (d, J = 8.4 Hz, 2H), 7.77 (d, J = 8.5 Hz, 2H), 7.62 (d, J = 8.3 Hz, 2H), 7.25 (d, J = 8.6 Hz, 2H), 4.71-4.65 (m, 1H), 4.06-3.99 (m, 1H), 3.61-3.56 (m, 2H), 3.56-3.51 (m, 3H), 3.51-3.43 (m, 3H), 3.24 (s, 3H), 2.55-2.45 (m, 2H), 2.03-1.93 (m, 3H), 1.82-1.74 (m, 4H), 1.68-1.60 (m, 2H), 1.44 (dd, J = 14.8, 7.5 Hz, 2H), 1.17 (t, J = 7.0 Hz, 3H), 0.97 (t, J = 7.4 Hz, 3H); MS m/z 650.30 (M + 1). |
| 74 | 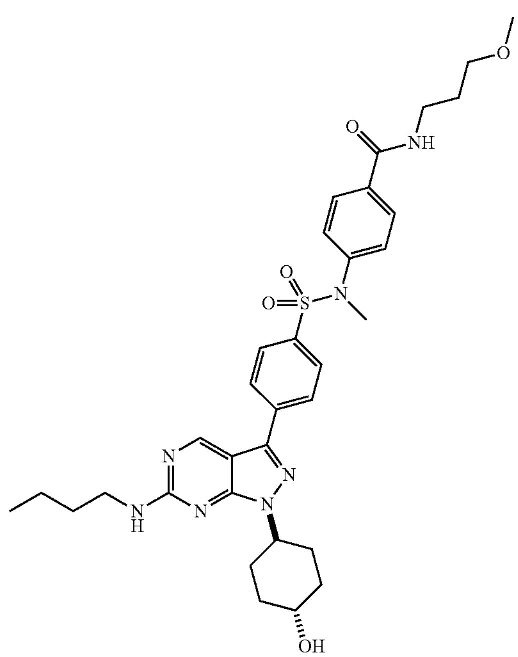 | UNC1315 A | ++++ | $^1$H NMR (400 MHz, CD$_3$OD + CDCl$_3$) δ 8.86 (s, 1H), 7.94-7.88 (m, 2H), 7.68-7.62 (m, 2H), 7.57-7.52 (m, 2H), 7.17-7.12 (m, 2H), 4.61-4.52 (m, 1H), 3.75-3.66 (m, 1H), 3.52-3.41 (m, 6H), 3.33-3.30 (m, 3H), 3.16 (s, 3H), 2.18-2.04 (m, 4H), 2.03-1.93 (m, 2H), 1.82 (dt, J = 11.9, 6.0 Hz, 2H), 1.60 (dq, J = 14.8, 7.4 Hz, 2H), 1.55-1.44 (m, 2H), 1.43-1.34 (m, 2H), 0.92 (t, J = 7.3 Hz, 3H); MS m/z 650.35 (M + 1). |

TABLE 5-continued

| Structure | Compound_ID | Mer IC$_{50}$ | Physical Data MS m/z (M + 1) or/and $^1$H NMR (400 MHz) |
|---|---|---|---|
| 75 | UNC1316 A | ++++ | $^1$H NMR (400 MHz, CD$_3$OD + CDCl$_3$) δ 8.82 (d, J = 6.5 Hz, 1H), 7.89-7.82 (m, 2H), 7.61-7.55 (m, 2H), 7.47 (d, J = 8.4 Hz, 2H), 7.09-7.03 (m, 2H), 4.56-4.45 (m, 1H), 3.94-3.88 (m, 1H), 3.40-3.28 (m, 6H), 3.21 (s, 3H), 3.18 (dt, J = 4.6, 1.5 Hz, 1H), 3.10-3.06 (m, 3H), 2.40-2.27 (m, 2H), 1.95-1.77 (m, 3H), 1.76-1.68 (m, 2H), 1.66-1.55 (m, 2H), 1.51 (dt, J = 14.8, 7.4 Hz, 2H), 1.34-1.24 (m, 2H), 0.82 (t, J = 7.3 Hz, 3H); MS m/z 650.30 (M + 1). |
| 76 | UNC1317 A | ++++ | $^1$H NMR (400 MHz, CD$_3$OD + CDCl$_3$) δ 8.85 (s, 1H), 7.95-7.86 (m, 2H), 7.70-7.63 (m, 2H), 7.58-7.50 (m, 2H), 7.17-7.10 (m, 2H), 4.59-4.50 (m, 1H), 3.74-3.63 (m, 1H), 3.57 (t, J = 6.8 Hz, 2H), 3.42 (t, J = 7.1 Hz, 2H), 3.28 (dt, J = 3.2, 1.6 Hz, 1H), 3.15 (s, 3H), 2.45-2.32 (m, 2H), 2.16-2.03 (m, 4H), 2.01-1.92 (m, 2H), 1.63-1.54 (m, 2H), 1.53-1.43 (m, 2H), 1.41-1.33 (m, 2H), 0.91 (t, J = 7.4 Hz, 3H); MS m/z 674.30 (M + 1). |

TABLE 5-continued
| | Structure | Compound_ID | Mer IC$_{50}$ | Physical Data MS m/z (M + 1) or/and $^1$H NMR (400 MHz) |
|---|---|---|---|---|
| 77 | 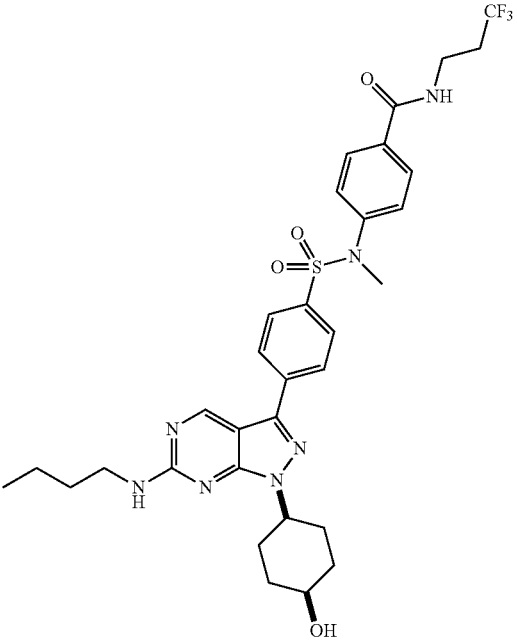 | UNC1318 A | +++ | $^1$H NMR (400 MHz, CD$_3$OD + CDCl$_3$) δ 8.81 (s, 1H), 7.89 (d, J = 8.5 Hz, 2H), 7.65 (d, J = 8.6 Hz, 2H), 7.50 (d, J = 8.5 Hz, 2H), 7.11 (d, J = 8.6 Hz, 2H), 4.60-4.51 (m, 1H), 3.99-3.94 (m, 1H), 3.52 (t, J = 6.9 Hz, 2H), 3.38 (t, J = 7.1 Hz, 2H), 3.24 (dt, J = 3.3, 1.6 Hz, 1H), 3.12 (s, 3H), 2.44-2.28 (m, 4H), 1.94-1.84 (m, 2H), 1.77-1.60 (m, 4H), 1.58-1.50 (m, 2H), 1.38-1.30 (m, 2H), 0.87 (t, J = 7.3 Hz, 3H); MS m/z 674.30 (M + 1). |
| 78 | 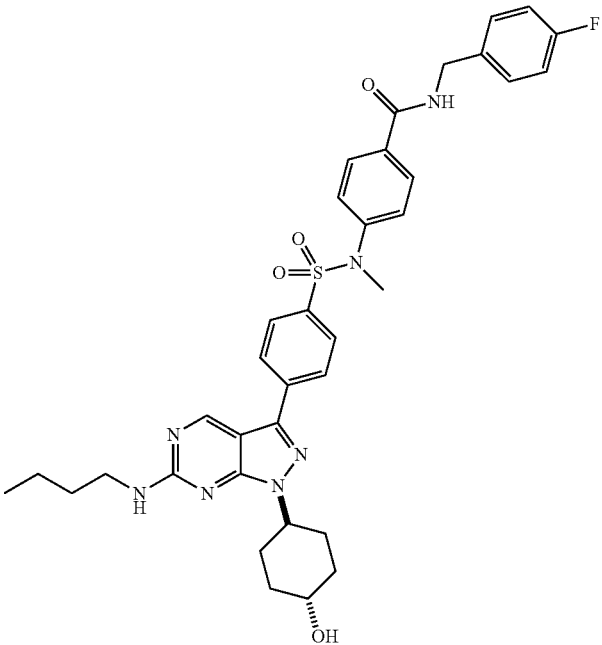 | UNC1319 A | +++ | $^1$H NMR (400 MHz, CD$_3$OD + CDCl$_3$) δ 8.84 (s 1H), 7.90 (d, J = 8.4 Hz, 2H), 7.72-7.67 (m, 2H), 7.53 (d, J = 8.4 Hz, 2H), 7.26-7.21 (m, 2H), 7.15-7.09 (m, 2H), 6.97-6.88 (m, 2H), 4.59-4.49 (m, 1H), 4.47 (s, 2H), 3.70-3.64 (m, 1H), 3.42 (t, J = 7.1 Hz, 2H), 3.27 (dt, J = 3.2, 1.6 Hz, 2H), 3.14 (s, 3H), 2.16-2.01 (m, 4H), 2.00-1.90 (m, 2H), 1.63-1.53 (m, 2H), 1.52-1.41 (m, 2H), 1.41-1.31 (m, 2H), 0.90 (t, J = 7.3 Hz, 3H); MS m/z 686.30 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 79 | 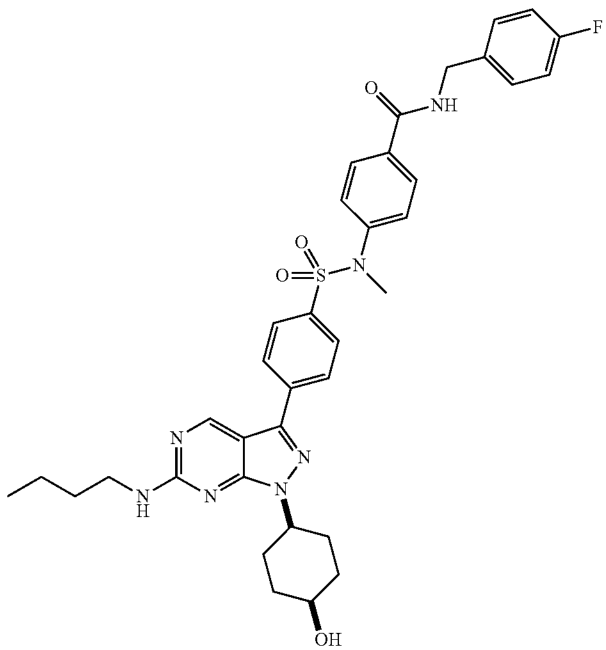 | UNC1320 A | + | $^1$H NMR (400 MHz, CD$_3$OD + CDCl$_3$) δ 8.81 (d, J = 5.6 Hz, 1H), 7.86 (dd, J = 8.3, 6.1 Hz, 2H), 7.69-7.61 (m, 2H), 7.48 (d, J = 8.4 Hz, 2H), 7.18 (dd, J = 8.6, 5.4 Hz, 2H), 7.12-7.04 (m, 2H), 6.91-6.80 (m, 2H), 4.57-4.48 (m, 1H), 4.40 (s, 2H), 3.93 (s, 1H), 3.68-3.59 (m, 1H), 3.39-3.32 (m, 2H), 3.20 (dt, J = 3.3, 1.6 Hz, 2H), 2.17-2.11 (m, 1H), 1.97-1.78 (m, 4H), 1.75-1.57 (m, 2H), 1.52 (dt, J = 14.9, 7.3 Hz, 2H), 1.39-1.25 (m, 3H), 0.84 (t, J = 7.3 Hz, 3H); MS m/z 686.30 (M + 1). |
| 80 | 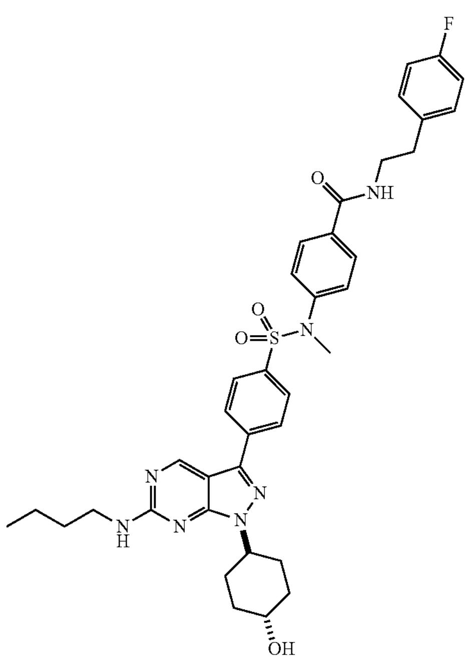 | UNC1321 A | +++ | $^1$H NMR (400 MHz, CD$_3$OD + CDCl$_3$) δ 8.82 (s, 1H), 7.91 (d, J = 8.5 Hz, 2H), 7.64-7.57 (m, 2H), 7.54 (d, J = 8.5 Hz, 2H), 7.21-7.06 (m, 4H), 6.94 (t, J = 8.7 Hz, 2H), 4.59-4.52 (m, 1H), 3.74-3.66 (m, 1H), 3.57 (t, J = 7.1 Hz, 2H), 3.43 (t, J = 7.1 Hz, 2H), 3.35 (s, 1H), 3.31 (dt, J = 3.3, 1.6 Hz, 3H), 3.18 (s, 2H), 2.84 (t, J = 7.1 Hz, 2H), 2.19-2.04 (m, 4H), 2.03-1.93 (m, 2H), 1.63-1.55 (m, 2H), 1.55-1.44 (m, 2H), 1.44-1.34 (m, 2H), 0.92 (t, J = 7.3 Hz, 3H); MS m/z 700.30 (M + 1). |

TABLE 5-continued
| | Structure | Compound_ID | Mer IC$_{50}$ | Physical Data MS m/z (M + 1) or/and $^1$H NMR (400 MHz) |
|---|---|---|---|---|
| 81 | 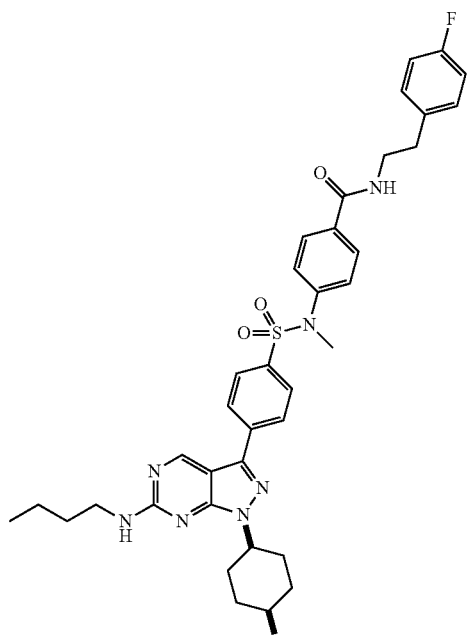 | UNC1322 A | +++ | $^1$H NMR (400 MHz, CD$_3$OD + CDCl$_3$) δ 8.85 (s, 1H), 7.97-7.89 (m, 2H), 7.66-7.58 (m, 2H), 7.58-7.52 (m, 2H), 7.19-7.09 (m, 4H), 6.99-6.90 (m, 2H), 4.66-4.57 (m, 1H), 4.05-4.00 (m, 1H), 3.80-3.72 (m, 1H), 3.57 (t, J = 7.2 Hz, 2H), 3.46-3.40 (m, 2H), 3.33-3.29 (m, 2H), 3.17 (d, J = 9.0 Hz, 3H), 2.84 (t, J = 7.2 Hz, 2H), 2.50-2.35 (m, 2H), 2.09-1.86 (m, 3H), 1.81-1.66 (m, 3H), 1.64-1.54 (m, 2H), 1.44-1.35 (m, 2H), 0.92 (t, J = 7.3 Hz, 3H); MS m/z 700.30 (M + 1). |
| 82 | 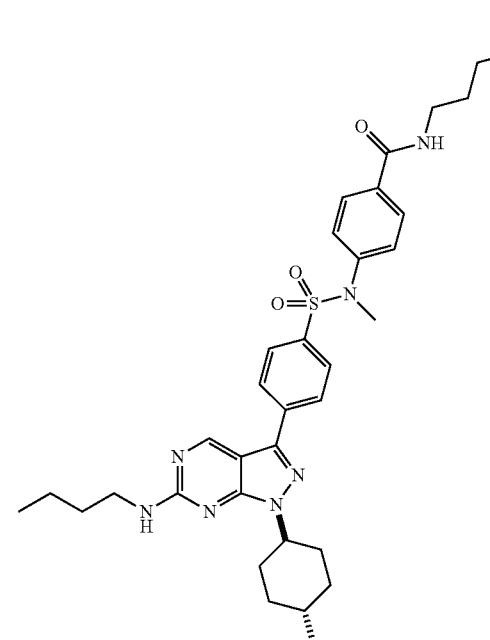 | UNC1323 A | +++ | $^1$H NMR (400 MHz, CD$_3$OD + CDCl$_3$) δ 8.86 (s, 1H), 7.90 (d, J = 8.3 Hz, 2H), 7.65 (d, J = 8.6 Hz, 2H), 7.53 (d, J = 8.4 Hz, 2H), 7.12 (d, J = 8.6 Hz, 2H), 4.60-4.48 (m, 1H), 3.82 (s, 1H), 3.72-3.65 (m, 1H), 3.42 (t, J = 7.1 Hz, 2H), 3.35-3.25 (m, 3H), 3.14 (s, 3H), 2.17-2.01 (m, 4H), 2.00-1.91 (m, 2H), 1.78-1.63 (m, 1H), 1.62-1.43 (m, 6H), 1.41-1.34 (m, 2H), 1.30-1.24 (m, 3H), 1.14 (d, J = 15.6 Hz, 1H), 0.94-0.86 (m, 3H), 0.82 (t, J = 6.8 Hz, 3H); MS m/z 648.30 (M + 1). |

TABLE 5-continued
| Structure | Compound_ID | Mer IC$_{50}$ | Physical Data MS m/z (M + 1) or/and $^1$H NMR (400 MHz) |
|---|---|---|---|
| 83 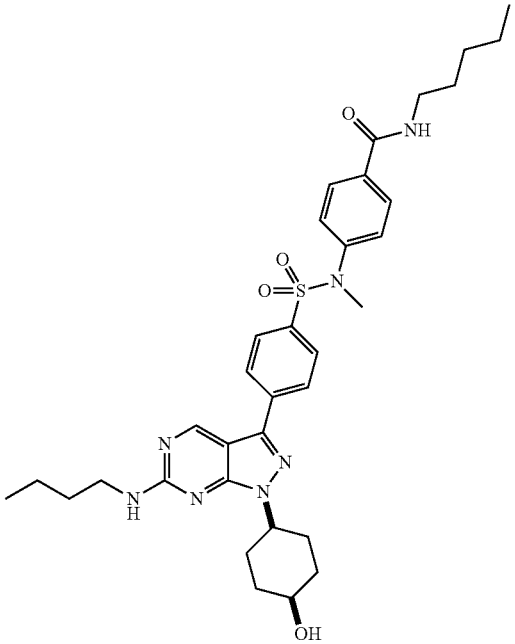 | UNC1324 A | +++ | $^1$H NMR (400 MHz, CD$_3$OD + CDCl$_3$) δ 8.78 (s, 1H), 7.92-7.82 (m, 2H), 7.65-7.57 (m, 2H), 7.52-7.44 (m, 2H), 7.11-7.02 (m, 2H), 4.60-4.47 (m, 1H), 3.73-3.61 (m, 1H), 3.43-3.29 (m, 2H), 3.29-3.16 (m, 3H), 3.10 (s, 3H), 2.44-2.28 (m, 1H), 2.25-2.10 (m, 1H), 2.02-1.77 (m, 4H), 1.76-1.58 (m, 2H), 1.58-1.42 (m, 4H), 1.42-1.28 (m, 2H), 1.28-1.16 (m, 4H), 0.85 (t, J = 7.3 Hz, 3H), 0.82-0.71 (m, 3H); MS m/z 648.30 (M + 1). |
| 84 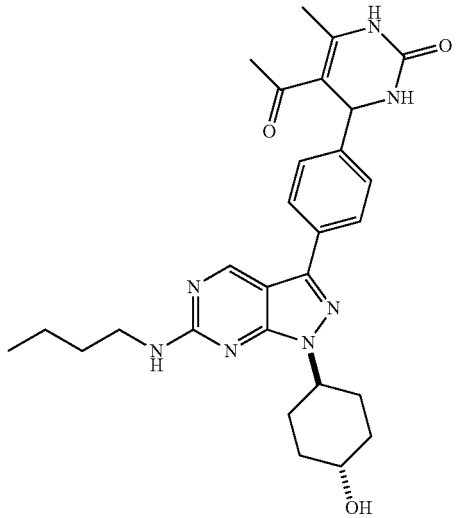 | UNC1325 A | +++ | $^1$H NMR (400 MHz, CD$_3$OD + CDCl$_3$) δ 8.86 (s, 1H), 7.74 (d, J = 8.3 Hz, 2H), 7.37 (d, J = 8.3 Hz, 2H), 5.42 (s, 1H), 4.58-4.46 (m, 1H), 3.72-3.64 (m, 1H), 3.46 (t, J = 7.2 Hz, 2H), 3.31 (dd, J = 3.2, 1.6 Hz, 1H), 2.31 (s, 3H), 2.20-2.02 (m, 7H), 2.02-1.93 (m, 2H), 1.62 (dt, J = 14.8, 7.5 Hz, 2H), 1.54-1.43 (m, 2H), 1.43-1.31 (m, 2H), 0.92 (t, J = 7.4 Hz, 3H); MS m/z 518.30 (M + 1). |

TABLE 5-continued
| | Structure | Compound_ID | Mer IC$_{50}$ | Physical Data MS m/z (M + 1) or/and $^1$H NMR (400 MHz) |
|---|---|---|---|---|
| 85 | 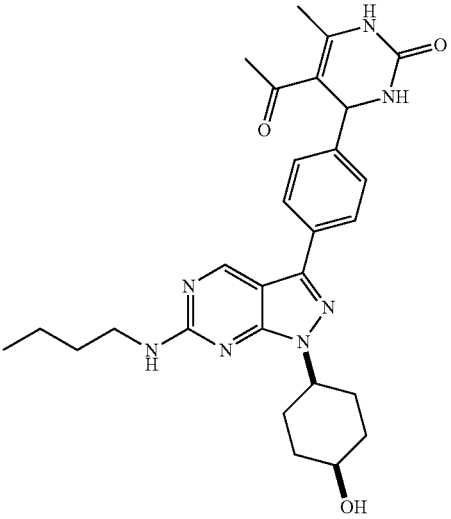 | UNC1326 A | ++++ | $^1$H NMR (400 MHz, CD$_3$OD + CDCl$_3$) δ 9.37 (s, 1H), 8.80 (t, J = 8.9 Hz, 1H), 8.51 (s, 1H), 7.71-7.60 (m, 2H), 7.39-7.25 (m, 2H), 6.83 (s, 1H), 5.43 (s, 1H), 5.38(s, 1H), 4.62 (dt, J = 14.7, 11.9 Hz, 1H), 4.13 (s, 1H), 3.88-3.80 (m, 1H), 3.56-3.44 (m, 2H), 2.55-2.33 (m, 2H), 2.29 (d, J = 10.9 Hz, 3H), 2.15-1.89 (m, 6H), 1.78 (d, J = 10.5 Hz, 2H), 1.68 (dt, J = 14.9, 7.4 Hz, 2H), 1.43 (dq, J = 14.5, 7.3 Hz, 2H), 0.96 (t, J = 7.4 Hz, 3H); MS m/z 518.30 (M + 1). |
| 86 | 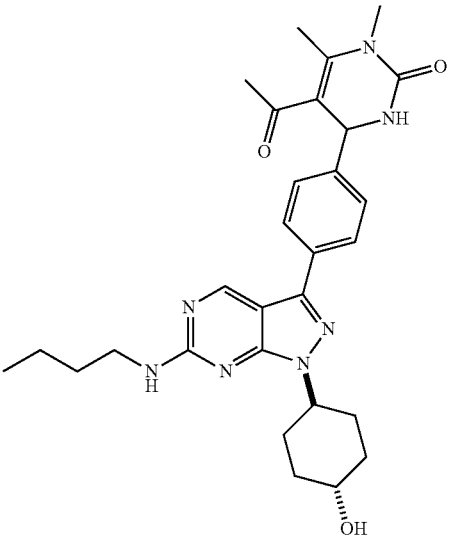 | UNC1343 A | ++++ | $^1$H NMR (400 MHz, CDCl$_3$) δ 9.43 (brs, 1H), 8.74 (s, 1H), 7.75 (d, J = 8.2 Hz, 2H), 7.36 (d, J = 8.3 Hz, 2H), 6.08 (d, J = 3.2 Hz, 1H), 5.42 (d, J = 3.3 Hz, 1H), 4.63-4.54 (m, 1H), 3.84-3.74 (m, 1H), 3.55-3.46 (m, 2H), 3.23 (s, 3H), 2.48 (s, 3H), 2.24-2.09 (m, 7H), 2.09-1.98 (m, 2H), 1.73-1.65 (m, 2H), 1.61-1.50 (m, 2H), 1.47-1.39 (m, 2H), 0.97 (t, J = 7.4 Hz, 3H); MS m/z 532.40 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 87 | 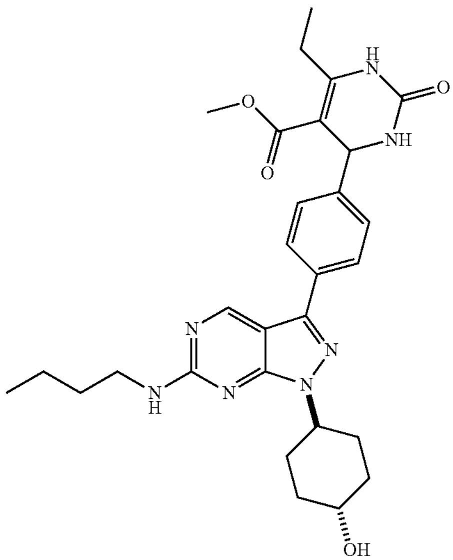 | UNC1344 A | ++++ | $^1$H NMR (400 MHz, CDCl$_3$) δ 9.50 (s, 1H), 8.93 (s, 1H), 7.89 (d, J = 8.2 Hz, 2H), 7.83-7.68 (m, 1H), 7.56 (d, J = 8.2 Hz, 2H), 6.21 (s, 1H), 5.58 (d, J = 2.3 Hz, 1H), 4.79-4.68 (m, 1H), 3.99-3.91 (m, 1H), 3.67 (t, J = 6.7 Hz, 2H), 2.95-2.83 (m, 2H), 2.39-2.12 (m, 6H), 1.89-1.80 (m, 2H), 1.76-1.65 (m, 2H), 1.63-1.53 (m, 2H), 1.35 (t, J = 7.5 Hz, 3H), 1.13 (t, J = 7.4 Hz, 3H); MS m/z 548.30 (M + 1). |
| 88 | 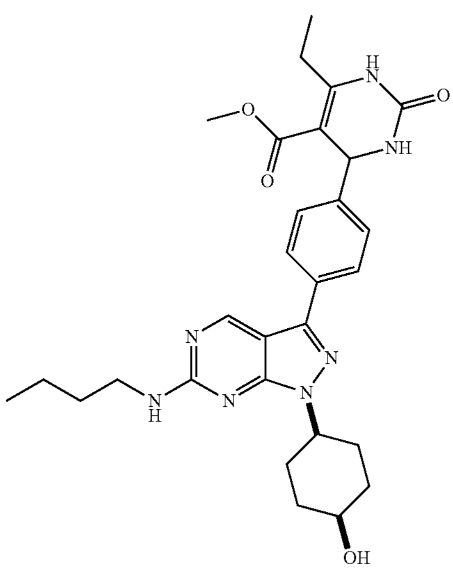 | UNC1345 A | ++++ | $^1$H NMR (400 MHz, CDCl$_3$) δ 8.86 (s, 1H), 7.73 (d, J = 8.3 Hz, 2H), 7.35 (d, J = 8.3 Hz, 2H), 5.32 (s, 1H), 4.60-4.49 (m, 1H), 4.02-3.96 (m, 1H), 3.54 (s, 3H), 3.44 (t, J = 7.2 Hz, 2H), 2.73-2.58 (m, 2H), 2.47-2.33 (m, 2H), 1.99-1.87 (m, 2H), 1.77-1.63 (m, 4H), 1.63-1.54 (m, 2H), 1.41-1.30 (m, 2H), 1.15 (t, J = 7.5 Hz, 3H), 0.89 (dd, J = 8.0, 6.7 Hz, 3H); MS m/z 548.30 (M + 1). |

TABLE 5-continued
| Structure | Compound_ID | Mer IC$_{50}$ | Physical Data MS m/z (M + 1) or/and $^1$H NMR (400 MHz) |
|---|---|---|---|
| 89 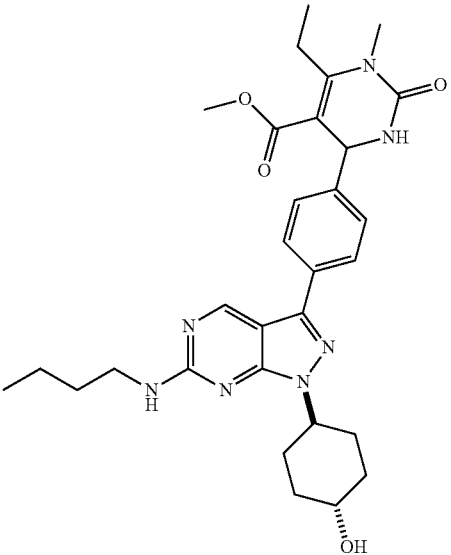 | UNC1346 A | ++++ | $^1$H NMR (400 MHz, CDCl$_3$) δ 8.78 (s, 1H), 7.77 (d, J = 8.2 Hz, 2H), 7.37 (d, J = 8.3 Hz, 2H), 5.76 (s, 1H), 5.41 (d, J = 3.1 Hz, 1H), 4.64-4.56 (m, 1H), 3.86-3.76 (m, 1H), 3.67 (s, 3H), 3.56-3.47 (m, 2H), 3.29 (s, 3H), 2.99 (q, J = 7.4 Hz, 2H), 2.25-2.11 (m, 4H), 2.09-2.01 (m, 2H), 1.73-1.64 (m, 2H), 1.63-1.51 (m, 2H), 1.49-1.41 (m, 2H), 1.24 (t, J = 7.4 Hz, 3H), 0.99 (t, J = 7.4 Hz, 3H); MS m/z 562.30 (M + 1). |
| 90 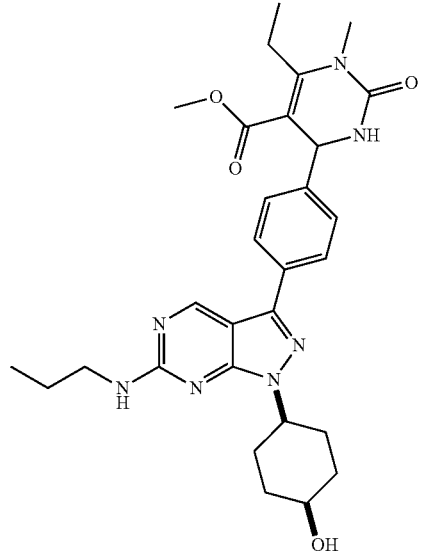 | UNC1347 A | ++++ | $^1$H NMR (400 MHz, CDCl$_3$ + CD$_3$OD) δ 8.76 (s, 1H), 7.75 (d, J = 8.0 Hz, 2H), 7.35 (d, J = 8.0 Hz, 2H), 5.91 (s, 1H), 5.38 (s, 1H), 4.65-4.55 (m, 1H), 4.12 (s, 1H), 3.65 (s, 3H), 3.50 (s, 2H), 3.26 (s, 3H), 2.97 (q, J = 7.3 Hz, 2H), 2.57-2.41 (m, 2H), 2.05-1.94 (m, 2H), 1.88-1.72 (m, 4H), 1.71-1.62 (m, 2H), 1.49-1.39 (m, 2H), 1.21 (t, J = 7.3 Hz, 3H), 0.96 (t, J = 7.3 Hz, 3H); MS m/z 562.30 (M + 1). |

| Structure | Compound_ID | Mer IC$_{50}$ | Physical Data MS m/z (M + 1) or/and $^1$H NMR (400 MHz) |
|---|---|---|---|
| 91 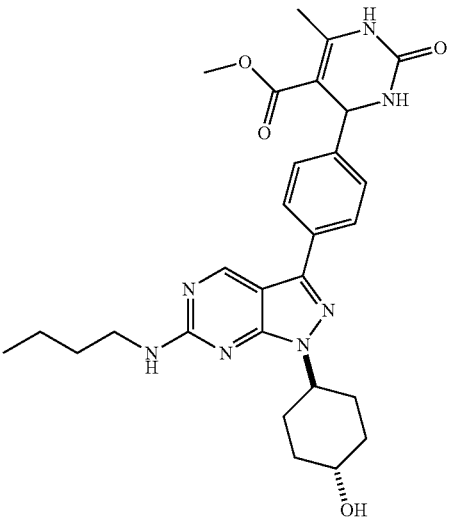 | UNC1348A | ++++ | $^1$H NMR (400 MHz, CDCl$_3$ + CD$_3$OD) δ 9.40 (s, 1H), 8.79 (s, 1H), 7.88 (s, 1H), 7.73 (d, J = 8.2 Hz, 2H), 7.40 (d, J = 8.1 Hz, 2H), 6.12 (s, 1H), 5.42 (s, 1H), 4.62-4.54 (m, 1H), 3.83-3.75 (m, 1H), 3.60 (s, 3H), 3.51 (t, J = 6.8 Hz, 2H), 2.32 (s, 3H), 2.21-2.10 (m, 4H), 2.07-2.00 (m, 2H), 1.73-1.65 (m, 2H), 1.61-1.50 (m, 2H), 1.48-1.37 (m, 2H), 0.97 (t, J = 7.4 Hz, 3H); MS m/z 534.30 (M + 1). |
| 92 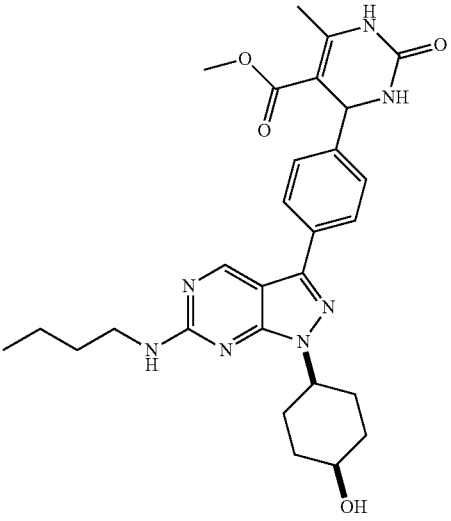 | UNC1349A | ++++ | $^1$H NMR (400 MHz, CDCl$_3$ + CD$_3$OD) δ 9.35 (s, 1H), 8.85 (s, 1H), 8.45 (s, 1H), 7.68 (d, J = 7.9 Hz, 2H), 7.31 (d, J = 7.7 Hz, 2H), 6.63 (s, 1H), 5.36 (s, 1H), 4.66-4.56 (m, 1H), 4.14 (s, 1H), 3.64-3.58 (m, 1H), 3.56 (s, 2H), 3.55-3.47 (m, 2H), 2.53-2.36 (m, 2H), 2.28 (s, 2H), 2.05-1.96 (m, 2H), 1.83-1.74 (m, 3H), 1.72-1.61 (m, 2H), 1.43 (dq, J = 14.6, 7.3 Hz, 2H), 0.96 (t, J = 7.4 Hz, 3H); MS m/z 534.30 (M + 1). |

| Structure | Compound_ID | Mer IC$_{50}$ | Physical Data MS m/z (M + 1) or/and $^1$H NMR (400 MHz) |
|---|---|---|---|
| 93 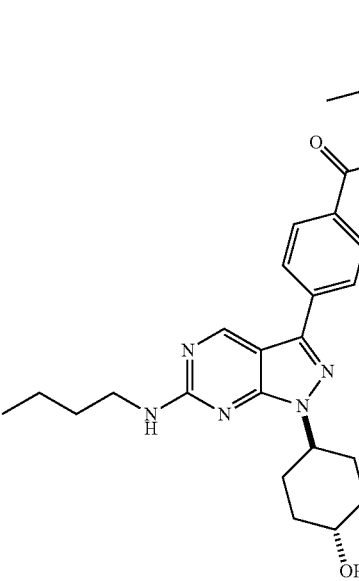 | UNC1350 A | ++++ | $^1$H NMR (400 MHz, CDCl$_3$ + CD$_3$OD) δ 9.38 (s, 1H), 8.91 (s, 1H), 7.97-7.90 (m, 4H), 7.57-7.50 (m, 2H), 7.46 (d, J = 9.1 Hz, 1H), 7.04-6.96 (m, 2H), 4.67-4.56 (m, 1H), 4.49-4.43 (m, 1H), 3.83-3.75 (m, 1H), 3.50 (t, J = 7.1 Hz, 2H), 2.26-2.11 (m, 5H), 2.09-2.01 (m, 2H), 1.70-1.62 (m, 2H), 1.60-1.50 (m, 2H), 1.48-1.40 (m, 2H), 1.06 (dd, J = 6.7, 4.2 Hz, 6H), 0.97 (t, J = 7.3 Hz, 3H); MS m/z 602.30 (M + 1). |
| 94 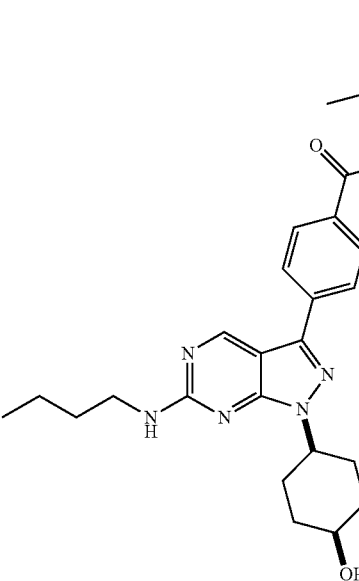 | UNC1351 A | ++++ | $^1$H NMR (400 MHz, CDCl$_3$) δ 9.22 (s, 1H), 8.85 (s, 1H), 7.86 (d, J = 4.3 Hz, 4H), 7.54 (dd, J = 8.3, 4.5 Hz, 2H), 7.44 (d, J = 7.8 Hz, 1H), 6.96 (t, J = 8.5 Hz, 2H), 4.74 (t, J = 7.9 Hz, 1H), 4.64 (t, J = 10.5 Hz, 1H), 4.15 (s, 1H), 3.57-3.44 (m, 2H), 2.60-2.45 (m, 2H), 2.40-2.25 (m, 1H), 2.03 (d, J = 11.8 Hz, 2H), 1.91-1.73 (m, 4H), 1.73-1.61 (m, 2H), 1.50-1.39 (m, 2H), 1.09 (d, J = 4.4 Hz, 6H), 0.98 (t, J = 7.3 Hz, 3H); MS m/z 602.30 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 95 | 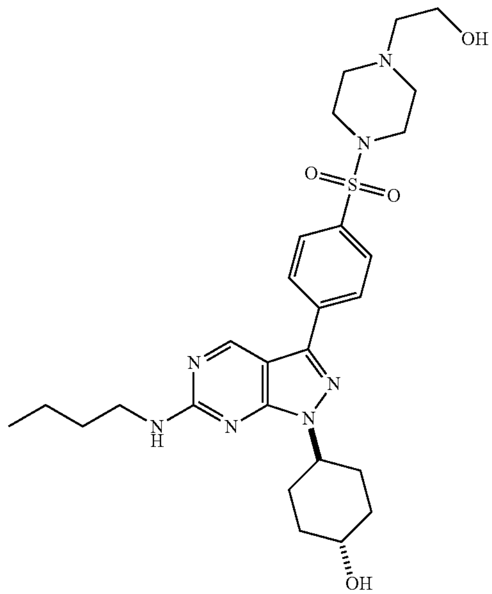 | UNC1288 A | ++++ | $^1$H NMR (400 MHz, CDCl$_3$) δ 9.09 (bs, 1H), 8.84 (s, 1H), 8.04 (d, J = 8.4 Hz, 2H), 7.85 (d, J = 8.5 Hz, 2H), 4.72-4.60 (m, 2H), 3.97 (s, 2H), 3.89-3.79 (m, 1H), 3.59-3.50 (m, 3H), 3.38 (bs, 5H), 3.20-3.09 (m, 3H), 2.26-2.16 (m, 3H), 2.13-2.04 (m, 2H), 1.72 (dt, J = 14.9, 7.4 Hz, 2H), 1.58 (dt, J = 16.4, 11.3 Hz, 2H), 1.47 (dq, J = 14.5, 7.4 Hz, 2H), 1.00 (t, J = 7.4 Hz, 3H); MS m/z 558.30 (M + 1). |
| 96 | 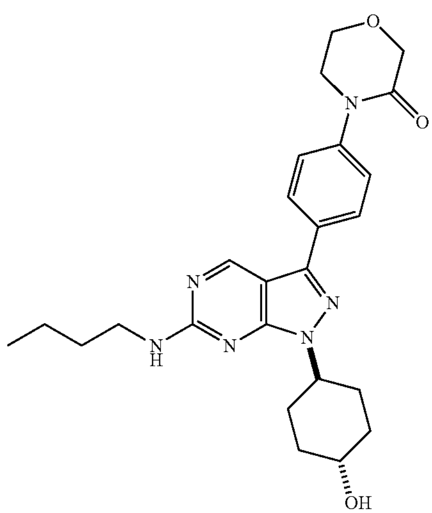 | UNC1352 A | ND | $^1$H NMR (400 MHz, CD$_3$OD) δ 9.11 (s, 1H), 8.04-7.98 (m, 2H), 7.58-7.52 (m, 2H), 4.65 (tt, J = 11.6, 3.9 Hz, 1H), 4.32 (s, 2H), 4.07 (dd, J = 5.8, 4.3 Hz, 2H), 3.85 (dd, J = 5.8, 4.3 Hz, 2H), 3.76-3.67 (m, 1H), 3.54 (t, J = 7.1 Hz, 2H), 2.27-2.00 (m, 6H), 1.75-1.65 (m, 2H), 1.60-1.43 (m, 4H), 1.02 (t, J = 7.4 Hz, 3H); MS m/z 465.30 (M + 1). |
| 97 | 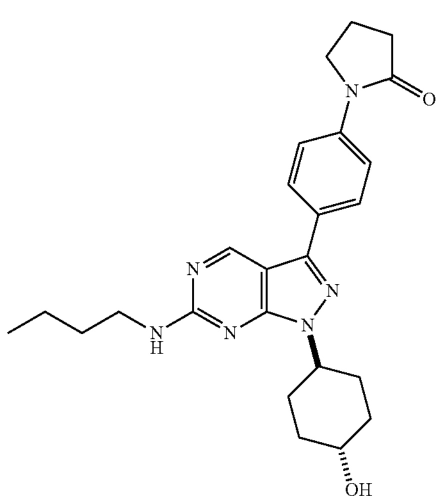 | UNC1355 A | ND | $^1$H NMR (400 MHz, CD$_3$OD) δ 9.07 (s, 1H), 7.95 (d, J = 8.8 Hz, 2H), 7.79 (d, J = 8.8 Hz, 2H), 4.70-4.59 (m, 1H), 3.99 (t, J = 7.1 Hz, 2H), 3.73 (ddd, J = 14.8, 9.5, 4.0 Hz, 1H), 3.53 (t, J = 7.1 Hz, 2H), 2.64 (t, J = 8.1 Hz, 2H), 2.29-2.10 (m, 6H), 2.05 (d, J = 12.3 Hz, 2H), 1.70 (dt, J = 14.8, 7.3 Hz, 2H), 1.61-1.42 (m, 4H), 1.01 (t, J = 7.4 Hz, 3H); MS m/z 449.30 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 98 | 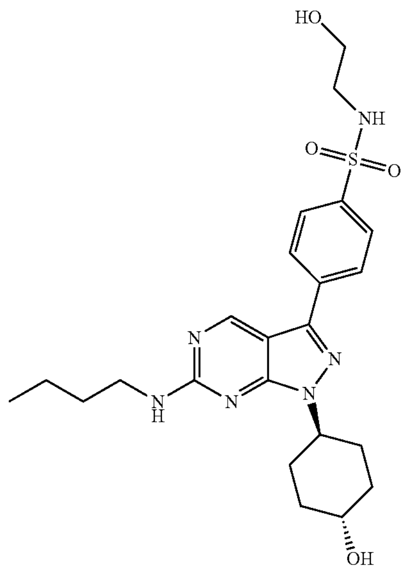 [SMILES: CCCCNc1ncc2c(-c3ccc(S(=O)(=O)NCCO)cc3)nn([C@H]3CC[C@H](O)CC3)c2n1] | UNC1227 A | ++++ | $^1$H NMR (400 MHz, CD$_3$OD + CDCl$_3$) δ 8.94 (s, 1H), 8.01 (d, J = 8.4 Hz, 2H), 7.93 (d, J = 8.4 Hz, 2H), 4.70-4.50 (m, 1H), 3.78-3.65 (m, 1H), 3.57 (t, J = 5.3 Hz, 2H), 3.48 (t, J = 7.1 Hz, 2H), 3.01 (t, J = 5.3 Hz, 2H), 2.24-2.07 (m, 4H), 2.02 (d, J = 11.1 Hz, 2H), 1.70-1.59 (m, 2H), 1.59-1.48 (m, 2H), 1.42 (dt, J = 14.5, 7.4 Hz, 2H), 0.96 (t, J = 7.3 Hz, 3H); MS m/z 489.2 (M + 1). |
| 99 | 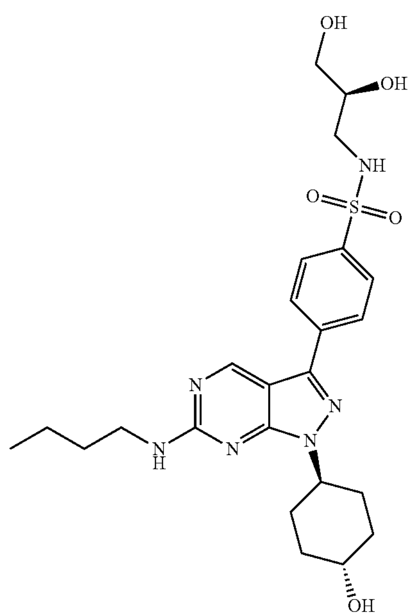 [SMILES: CCCCNc1ncc2c(-c3ccc(S(=O)(=O)NC[C@H](O)CO)cc3)nn([C@H]3CC[C@H](O)CC3)c2n1] | UNC1228 A | ++++ | $^1$H NMR (400 MHz, CD$_3$OD + CDCl$_3$) δ 8.92 (s, 1H), 8.03 (d, J = 8.7 Hz, 2H), 7.93 (d, J = 8.6 Hz, 2H), 4.69-4.54 (m, 1H), 3.78-3.62 (m, 2H), 3.56-3.42 (m, 4H), 3.04 (dd, J = 13.1, 4.6 Hz, 1H), 2.89 (dd, J = 13.1, 6.9 Hz, 1H), 2.24-1.95 (m, 6H), 1.69-1.58 (m, 2H), 1.53 (dd, J = 17.4, 6.6 Hz, 2H), 1.44 (dq, J = 14.4, 7.3 Hz, 2H), 0.96 (t, J = 7.4 Hz, 3H); MS m/z 519.2 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 100 | 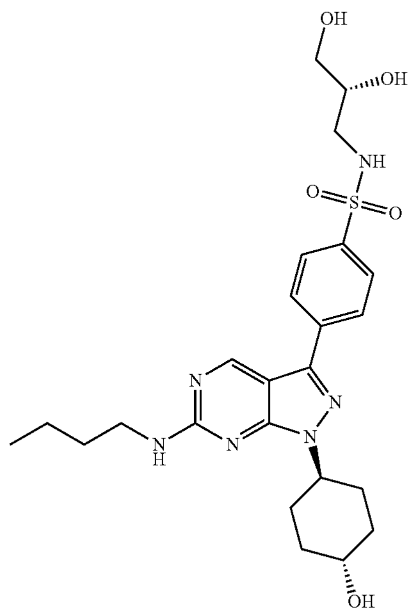 [SMILES: CCCCNc1ncc2c(-c3ccc(S(=O)(=O)NC[C@@H](O)CO)cc3)nn([C@H]3CC[C@H](O)CC3)c2n1] | UNC1229A | ++++ | $^1$H NMR (400 MHz, CD$_3$OD + CDCl$_3$) δ 8.92 (s, 1H), 8.03 (d, J = 8.7 Hz, 2H), 7.93 (d, J = 8.6 Hz, 2H), 4.69-4.54 (m, 1H), 3.78-3.62 (m, 2H), 3.56-3.42 (m, 4H), 3.04 (dd, J = 13.1, 4.6 Hz, 1H), 2.89 (dd, J = 13.1, 6.9 Hz, 1H), 2.24-1.95 (m, 6H), 1.69-1.58 (m, 2H), 1.53 (dd, J = 17.4, 6.6 Hz, 2H), 1.44 (dq, J = 14.4, 7.3 Hz, 2H), 0.96 (t, J = 7.4 Hz, 3H); MS m/z 519.2 (M + 1). |
| 101 | 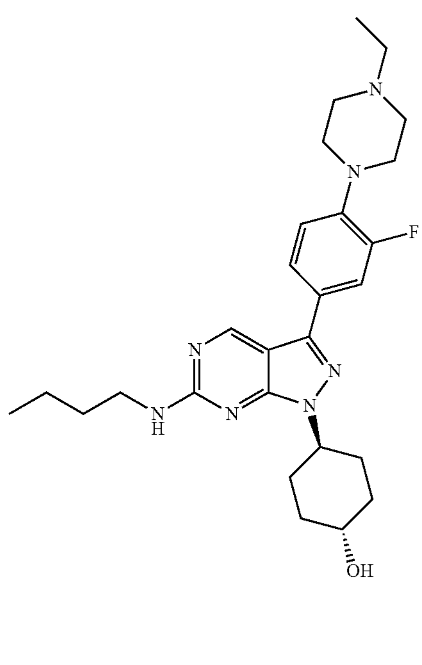 [SMILES: CCCCNc1ncc2c(-c3ccc(N4CCN(CC)CC4)c(F)c3)nn([C@H]3CC[C@H](O)CC3)c2n1] | UNC1285A | ++++ | $^1$H NMR(400 MHz, CD$_3$OD) δ 9.16 (s, 1H), 7.80-7.69 (m, 2H), 7.26 (t, J = 8.6 Hz, 1H), 4.71-4.60 (m, 1H), 3.80-3.66 (m, 5H), 3.56 (t, J = 7.1 Hz, 2H), 3.36-3.18 (m, 4H), 2.26-2.00 (m, 6H), 1.75-1.66 (m, 2H), 1.60-1.45 (m, 4H), 1.42 (t, J = 7.3 Hz, 3H), 1.02 (t, J = 7.4 Hz, 3H); MS m/z 496.4 (M + 1). |

TABLE 5-continued

| | Structure | Compound_ID | Mer IC$_{50}$ | Physical Data MS m/z (M + 1) or/and $^1$H NMR (400 MHz) |
|---|---|---|---|---|
| 102 | 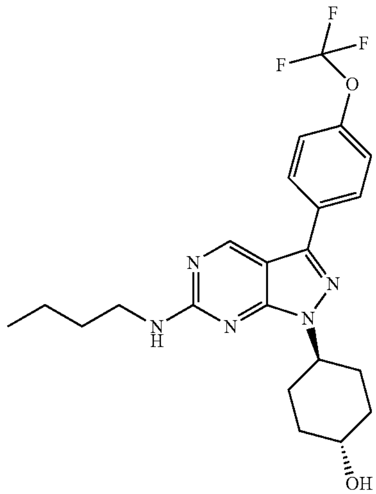 [SMILES: CCCCNc1ncc2c(-c3ccc(OC(F)(F)F)cc3)nn([C@H]3CC[C@H](O)CC3)c2n1] | UNC1286 A | +++ | $^1$H NMR (400 MHz, CDCl$_3$) δ 8.89 (s, 1H), 7.95-7.87 (m, 2H), 7.32 (dd, J = 8.8, 0.9 Hz, 2H), 5.29 (bs, 1H), 4.68-4.57 (m, 1H), 3.89-3.77 (m, 1H), 3.51 (dd, J = 12.9, 7.0 Hz, 2H), 2.29-2.12 (m, 4H), 2.06 (d, 2H), 1.70-1.60 (m, 2H), 1.56-1.51 (m, 2H), 1.50-1.40 (m, 2H), 0.99 (t, J = 7.3 Hz, 3H); MS m/z 450.2 (M + 1). |
| 103 | 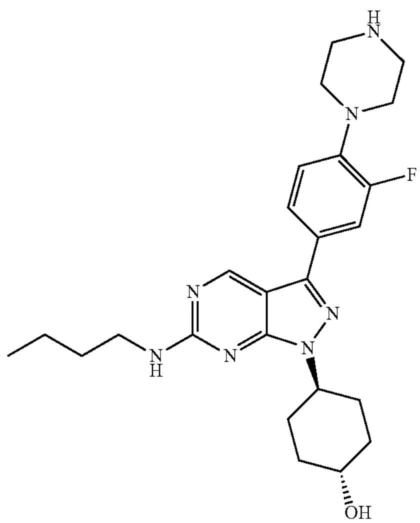 [SMILES: CCCCNc1ncc2c(-c3ccc(N4CCNCC4)c(F)c3)nn([C@H]3CC[C@H](O)CC3)c2n1] | UNC1287 A | ++++ | $^1$H NMR (400 MHz, CD$_3$OD) δ 8.97-8.86 (m, 1H), 7.73-7.60 (m, 2H), 7.24-7.13 (m, 1H), 4.68-4.55 (m, 1H), 3.75-3.66 (m, 1H), 3.47 (t, J = 7.1 Hz, 2H), 3.35-3.32 (bs, 8H), 2.28-2.08 (m, 4H), 2.05-1.96 (m, 2H), 1.71-1.60 (m, 2H), 1.58-1.40 (m, 4H), 1.04-0.97 (m, 3H); MS m/z 468.3 (M + 1). |

Compounds made as mixtures in the tables above are made as pure isomers by use of an isomerically pure starting material in accordance with known techniques.

The foregoing is illustrative of the present invention, and is not to be construed as limiting thereof. The invention is defined by the following claims, with equivalents of the claims to be included therein.

That which is claimed is:

1. A compound of Formula I:

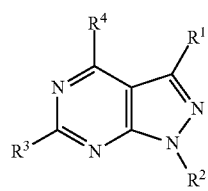

(I)

wherein:
R$^1$ is aryl, wherein the aryl is unsubstituted or substituted from 1 to 3 times with halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocylooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1, 2 or 3;

or R$^1$ is heteroaryl, wherein the heteroaryl is unsubstituted or substituted from 1 to 3 times with halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3;

$R^2$ is —$R^5R^6$, where $R^5$ is a covalent bond or C1 to C3 alkyl and $R^6$ is cycloalkyl, wherein $R^6$ is optionally substituted from one to two times with independently selected polar groups;

$R^3$ is —$NR^7R^8$, where $R^7$ and $R^8$ are each independently selected from H, alkyl, arylalkyl, and alkoxyalkyl; wherein the alkyl, arylalkyl, or alkoxyalkyl is unsubstituted or substituted from 1 to 3 times with alkyl, cycloalkyl, cycloalkylalkyl, heterocycloalkyl, aryl, or heteroaryl; and $R^4$ is H, loweralkyl, halo, or loweralkoxy;

or a pharmaceutically acceptable salt thereof.

2. The compound of claim 1, wherein $R^5$ is C1 to C3 alkyl.

3. The compound of claim 2, wherein $R^5$ is —CH$_2$—.

4. The compound of claim 1, wherein $R^1$ is phenyl, or pyridyl, which phenyl or pyridyl is unsubstituted or substituted from 1 to 3 times with halo, amino, nitro, alkyl, alkoxyl, haloalkyl, cycloalkyl, heterocycloalkyl, aryl, or heteroaryl.

5. The compound of claim 1, wherein $R^8$ is C1-C8 alkyl or C1-C8 arylalkyl; wherein the alkyl or arylalkyl is unsubstituted or substituted from 1 to 3 times with alkyl, cycloalkyl, cycloalkylalkyl, heterocycloalkyl, aryl, or heteroaryl.

6. The compound of claim 1, wherein $R^6$ is cyclohexyl.

7. The compound of claim 1, wherein $R^6$ is substituted once with hydroxyl.

8. The compound of claim 1, wherein $R^7$ is H.

9. The compound of claim 1, wherein $R^8$ is loweralkyl.

10. The compound of claim 1, wherein $R^4$ is H.

11. The compound of claim 1, wherein said compound has the structure:

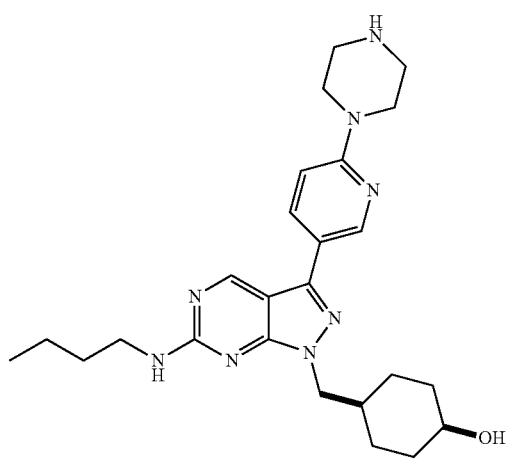

or a pharmaceutically acceptable salt thereof.

12. A composition comprising a compound of claim 1 in a pharmaceutically acceptable carrier.

13. A compound of Formula I:

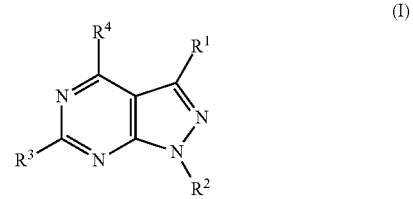

wherein:

$R^1$ is phenyl, which phenyl is unsubstituted or substituted from 1 to 3 times with halo, amino, nitro, alkyl, alkoxyl, haloalkyl, cycloalkyl, cycloalkylalkyl, heterocycloalkyl, aryl, or heteroaryl, $R^2$ is —$R^5R^6$, where $R^5$ is a covalent bond or C1 to C3 alkyl and $R^6$ is cycloalkyl, wherein $R^6$ is optionally substituted from one to two times with independently selected polar groups;

$R^3$ is —$NR^7R^8$, where $R^7$ and $R^8$ are each independently selected from H, alkyl, arylalkyl, and alkoxyalkyl; wherein the alkyl, arylalkyl, or alkoxyalkyl is unsubstituted or substituted from 1 to 3 times with alkyl, cycloalkyl, cycloalkylalkyl, heterocycloalkyl, aryl, or heteroaryl; and $R^4$ is H, loweralkyl, halo, or loweralkoxy;

or a pharmaceutically acceptable salt thereof.

14. The compound of claim 13, wherein $R^6$ is cyclohexyl substituted once with hydroxyl.

15. The compound of claim 13, wherein $R^7$ is H.

16. The compound of claim 14, wherein $R^8$ is loweralkyl.

17. The compound of claim 15, wherein $R^4$ is H.

18. The compound of claim 1, wherein the compound has the structure:

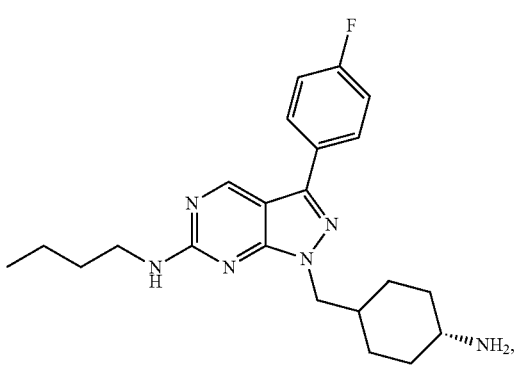

or a pharmaceutically acceptable salt thereof.

19. The compound of claim 1, wherein the compound has the structure:

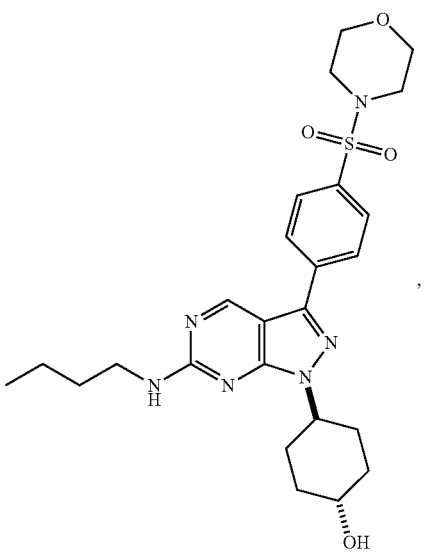

or a pharmaceutically acceptable salt thereof.

20. A compound of Formula I,

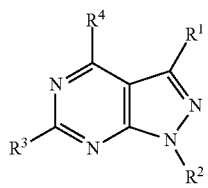

(I)

wherein:

R¹ is aryl or heteroaryl; wherein the aryl or heteroaryl is unsubstituted or substituted from 1 to 3 times with halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3;

R² is —R⁵R⁶, where R⁵ is a covalent bond or C1 to C3 alkyl and R⁶ is cycloalkyl, wherein R⁶ is optionally substituted from one to two times with independently selected polar groups;

R³ is —NR⁷R⁸, where R⁷ is selected from H, alkyl, arylalkyl, and alkoxyalkyl; and R⁸ is C3-C8 cycloalkyl, wherein the cycloalkyl is unsubstituted or substituted from 1 to 3 times with alkyl, cycloalkyl, cycloalkylalkyl, heterocycloalkyl, aryl, or heteroaryl; and R⁴ is H, loweralkyl, halo, or loweralkoxy;

or a pharmaceutically acceptable salt thereof.

21. A composition comprising a compound of claim 13 in a pharmaceutically acceptable carrier.

22. A composition comprising a compound of claim 20 in a pharmaceutically acceptable carrier.

\* \* \* \* \*